US007150974B1

(12) United States Patent
Segre et al.

(10) Patent No.: US 7,150,974 B1
(45) Date of Patent: Dec. 19, 2006

(54) PARATHYROID HORMONE RECEPTOR BINDING METHOD

(75) Inventors: Gino V. Segre, Wayland, MA (US); Henry M. Kronenberg, Belmont, MA (US); Abdul-Badi Abou-Samra, Plainville, MA (US); Harald Juppner, Boston, MA (US); John T. Potts, Jr., West Newton, MA (US); Ernestina Schipani, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/199,874

(22) Filed: Nov. 24, 1998

Related U.S. Application Data

(60) Division of application No. 08/471,494, filed on Jun. 6, 1995, now Pat. No. 5,840,853, which is a continuation of application No. 08/468,249, filed on Jun. 6, 1995, now Pat. No. 5,886,148, which is a division of application No. 07/864,475, filed on Apr. 6, 1992, now Pat. No. 5,494,806, which is a continuation-in-part of application No. 07/681,702, filed on Apr. 5, 1991, now abandoned.

(51) Int. Cl.
*G01N 33/53* (2006.01)

(52) U.S. Cl. .................. 435/7.2; 435/7.1; 435/69.1; 436/501

(58) Field of Classification Search ............. 435/7.2, 435/7.1; 436/501
See application file for complete search history.

(56) References Cited

U.S. PATENT DOCUMENTS

| 4,508,828 A | * | 4/1985 | Lindall et al. |
| 4,736,866 A | | 4/1988 | Leder et al. |
| 4,740,463 A | | 4/1988 | Weinberg et al. |
| 5,001,223 A | | 3/1991 | Rosenblatt et al. |
| 5,217,896 A | | 6/1993 | Kramer et al. |
| 5,652,110 A | | 7/1997 | Kim et al. |
| 5,660,826 A | | 8/1997 | Grumfield et al. |

FOREIGN PATENT DOCUMENTS

JP    64-13100    1/1989

OTHER PUBLICATIONS

Luden et al., "Molecular cloning of candidate sequences for the mouse osteoblast parathyroid hormone receptor," *Calcium regulation and bone metabolism. Basic and clinical aspects* 10:39–44, 1990.
Abou–Samra et al., *Endocrinology*, 124:1107–1113, 1989.
Abou–Samra et al., *Endocrinology*, 125:2215–2217, 1989.
Abou–Samra et al., *Endocrinology*, 125:2594–2599, 1989.
Abou–Samra et al., *J. of Biological Chemistry*, 265:58–62, 1990.
Abou–Samra et al., *Endocrinology*, 129:2547–2554, 1991.
Abou–Samra et al., *Proc. Natl. Acad. Sci. USA*, 89:2732–2736, 1992.
Bonventre et al., *J. of Biological Chemistry*, 265:4934–4938, 1990.
Caufield et al., American Society of Bone and Mineral Research Abstract #317, Jun. 1988.
Chan et al., *Molecular Endocrinology*, 4:638–646, 1990.
Chaung et al., *J. Biol. Chem.*, 262:10,760–10,766, 1987.
Chaung et al., American Society for Bone and Mineral Research Abstract #282, Jun. 1987.
Gearing et al., *EMBO J.*, 8:3667–3676, 1989.
Horiuchi et al., *J. of Biological Chemistry*, 266:4700–4705, 1991.
Hrucka et al., *J. Clin. Invest.*, 79:230–239, 1987.
Ishihara et al., *The EMBO Journal*, 10:1635–1641, 1991.
Juppner et al., *J. of Biological Chemistry*, 263:8557–8560, 1988.
Juppner et al., *Biochemistry*, 29:6941–6946, 1990.
Juppner et al., *Peptides*, 11:1139–1142, 1990.
Juppner et al., *Science*, 254:1–24–1026, 1991.
Karpf et al., American Society for Bone and Mineral Research Abstract #218, Jun. 1988.
Lee et al., *J. Bacteriol.*, 16:385–391, 1986.
Lim et al., *J. Biol. Chem.*, 263:11493–11497, 1988.
Lin et al., *Science*, 254:1022–1024, 1991.
Luben et al., *Abstracts of Paper Presented at the Twenty-seventh Annual Meeting of The American Society for Cell Biology*, 72 St. Louis, MO, 1987.
Luben et al., American Society for Bone and Mineral Research Abstract #319, Jun. 1988.
Luben et al., Twelfth Annual Meeting of the American Society for Bone and Mineral Research presented Abstract #272, Aug. 29, 1990.
Masu et al., *Nature*, 329:836–838, 1987.
Orloff et al., *J. of Biological Chemistry*, 264:6097–6103, 1989.
Rosenblatt et al., *Endocrinology*, 107:545–550, 1980.
Rosenblatt et al., *Proceedings of the Sixth American Peptide Symposium*, Ed. by E. Groos and M. Meienhofer, pp. 1025–1028, 1979.
Sambrook et al., *Molecular Cloning*, 2nd ed., Cold Spring Harbor (NY); ch. 11 (selected pages).
Segre et al., *J. of Biological Chemistry*, 254:6980–6986, 1979.
Segre et al., *Endocrinology*, 116:1024–1029, 1985.
Shigeno et al., *J. of Biological Chemistry*, 263:3864–3871, 1988.

(Continued)

*Primary Examiner*—Michael Pak
(74) *Attorney, Agent, or Firm*—Fish & Richardson P.C.

(57) ABSTRACT

DNA encoding a parathyroid hormone receptor; production and isolation of recombinant and synthetic parathyroid hormone receptor polypeptides and fragments; antibodies to parathyroid hormone receptors and receptor fragments; methods for screening candidate compounds for antagonistic or agonistic effects on parathyroid hormone receptor action; and diagnostic and therapeutic methods of these compounds are disclosed.

55 Claims, 36 Drawing Sheets

OTHER PUBLICATIONS

Shigeno et al., *J. of Biological Chemistry*, 263:3872–3878, 1988.
Shigeno et al., *Analytical Biochemistry*, 254:6980–6986, 1979.
Sims et al., *Science*, 241:585–589, 1988.
Wright et al., *Proc. Soc. Natl. Acad. Sci. USA*, 84:26–30, 1987.
Yamamoto et al., *J. Clin Invest.*, 71:404–407, 1983.
Yamamoto et al., *J. Bone and Mineral Research*, 3:289–295, 1988.
Yamamoto et al., *J. Bone and Mineral Research*, 3:707–712, 1988.
Yamamoto et al., *J. Bone and Mineral Research*, 122:1208–1217, 1988.
Weinshank et al., "Identification of a monoclonal antibody which interacts with the parathyroid hormone receptor–adenylate cyclase system in murine bone", Molecular and Cellular Endocrinology, vol. 41, pages 237–246 (1985).

* cited by examiner

```
TGGGCACAGC CACCCTGTTG GTAGTCCAGG GGCCAGCCCA CTGAGCTGTG        60
GTGGCCCCGT TGGACTCGGC CCTAGGGAAC GGCGGCG ATG GGA GCG CCC CGG ATC   115
                                    Met Gly Ala Pro Arg Ile
                                     1                   5

TCG CAC AGC CTT GCC TTG CTC CTC TGC TGC TCC GTG CTC AGC TCC GTC    163
Ser His Ser Leu Ala Leu Leu Leu Cys Cys Ser Val Leu Ser Ser Val
             10                      15                  20

TAC GCA CTG GAT GAT GCC GAT GTC ATA ACG AAG GAG GAG CAG ATC        211
Tyr Ala Leu Asp Asp Ala Asp Val Ile Thr Lys Glu Glu Gln Ile
         25                      30                  35

ATT CTT CGC AAT GCC CAG GCC CAG TGT GAG CAG CGC CTG AAA GAG        259
Ile Leu Arg Asn Ala Gln Ala Gln Cys Glu Gln Arg Leu Lys Glu
 40                      45                  50

GTC CTC AGG GTC CCT GAA CTT GCT GAA TCT GCC AAA GAC TGG ATG TCA    307
Val Leu Arg Val Pro Glu Leu Ala Glu Ser Ala Lys Asp Trp Met Ser
 55                      60                  65                  70

AGG TCT GCA AAG ACA AAG AAG GAA AAG CTT TAT CCC                    355
Arg Ser Ala Lys Thr Lys Lys Glu Lys Leu Tyr Pro
         75                      80                  85

CAG GCA GAG GAG TCC AGG GAA GTT TCT GAC AGG AGC CGG CTG CAG GAT    403
Gln Ala Glu Glu Ser Arg Glu Val Ser Asp Arg Ser Arg Leu Gln Asp
         90                      95                 100

GGC TTC TGC CTA CCT GAG TGG GAC AAC ATT GTG TGC TGG CCT GCT GGA    451
Gly Phe Cys Leu Pro Glu Trp Asp Asn Ile Val Cys Trp Pro Ala Gly
        105                     110                 115
```

FIG. 1A

```
GTG CCC GGC AAG GTG GTG GCC GTG CCC TGC CCC GAC TAC TTC TAC GAC       499
Val Pro Gly Lys Val Val Ala Val Pro Cys Pro Asp Tyr Phe Tyr Asp
        120                 125                 130

TTC AAC CAC AAA GGC CGA GCC TAT CGG CGC TGT GAC AGC AAT GGC AGC       547
Phe Asn His Lys Gly Arg Ala Tyr Arg Arg Cys Asp Ser Asn Gly Ser
        135                 140                 145                 150

TGG GAG CTG GTG CCT GGG AAC AAC CGG ACA TGG GCG AAT TAC AGC GAA       595
Trp Glu Leu Val Pro Gly Asn Asn Arg Thr Trp Ala Asn Tyr Ser Glu
        155                 160                 165

TGT GTC AAG TTT CTG ACC AAC GAG ACC CGG GAA GTC TTT GAT               643
Cys Val Lys Phe Leu Thr Asn Glu Thr Arg Glu Val Phe Asp
        170                 175                 180

CGC CTC GGA ATG ATC TAC ACT GTG GGC TAC TCC ATC TCT CTG GGC TCC       691
Arg Leu Gly Met Ile Tyr Thr Val Gly Tyr Ser Ile Ser Leu Gly Ser
        185                 190                 195

CTC ACT GTG GCT GTG CTG ATT CTG GGT TAC TTT AGG AGG TTA CAT TGC       739
Leu Thr Val Ala Val Leu Ile Leu Gly Tyr Phe Arg Arg Leu His Cys
        200                 205                 210

ACC CGA AAC TAC ATT CAC ATG CAT CTC TTC GTG TCC TTT ATG CTC CGG       787
Thr Arg Asn Tyr Ile His Met His Leu Phe Val Ser Phe Met Leu Arg
        215                 220                 225                 230

GCT GTA AGC ATC TTC ATC AAG GAT GCT GTG CTC TAC TCG GGG GTT TCC       835
Ala Val Ser Ile Phe Ile Lys Asp Ala Val Leu Tyr Ser Gly Val Ser
        235                 240                 245
```

FIG. 1B

```
ACA GAT GAA ATC GAG CGC ATC ACC GAG GAG CTG AGG GCC TTC ACA      883
Thr Asp Glu Ile Glu Arg Ile Thr Glu Glu Leu Arg Ala Phe Thr
            250                 255                 260

GAG CCT CCC GCT GAC AAG GCG GGT TTT GTG GGC TGC AGA GTG GCG      931
Glu Pro Pro Ala Asp Lys Ala Gly Phe Val Gly Cys Arg Val Ala
            265                 270                 275

GTA ACC GTC TTC CTT TAC TTC CTG ACC AAC TAC TGG ATC CTG          979
Val Thr Val Phe Leu Tyr Phe Leu Thr Asn Tyr Trp Ile Leu
            280                 285                 290

GTG GAA GGC CTC TAC CTT CAC AGC CTC ATC TTC ATG GCT TTC TCT     1027
Val Glu Gly Leu Tyr Leu His Ser Leu Ile Phe Met Ala Phe Ser
            295                 300                 305                 310

GAA AAG TAT CTC TGG GGT TTC ACA TTA TTT GGC TGG CTC CCT         1075
Glu Lys Tyr Leu Trp Gly Phe Thr Leu Phe Gly Trp Leu Pro
            315                 320                 325

GCC GTG TTT GTC GCT GTG TGG GTG ACC GTG AGG GCT ACA CTG GCC AAC 1123
Ala Val Phe Val Ala Val Trp Val Thr Val Arg Ala Thr Leu Ala Asn
            330                 335                 340

ACT GAG TGC TGG GAC CTG AGT TCG GGG AAT AAG AAA TGG ATC ATA CAG 1171
Thr Glu Cys Trp Asp Leu Ser Ser Gly Asn Lys Lys Trp Ile Ile Gln
            345                 350                 355

GTG CCC ATC CTG GCA GCT ATT GTG AAC TTT CTT TTT ATC AAT         1219
Val Pro Ile Leu Ala Ala Ile Val Val Asn Phe Leu Phe Ile Asn
            360                 365                 370
```

FIG. 1C

```
ATA ATC AGA GTC CTG GCT ACT AAA CTC CGG GAG ACC AAT GCA GGG AGA       1267
Ile Ile Arg Val Leu Ala Thr Lys Leu Arg Glu Thr Asn Ala Gly Arg
375                 380                 385                 390

TGT GAC ACG AGG CAA CAG TAT AGA AAG CTG CTG AAG TCC ACG CTA GTC       1315
Cys Asp Thr Arg Gln Gln Tyr Arg Lys Leu Leu Lys Ser Thr Leu Val
        395                 400                 405

CTC ATG CCG CTA TTT GGG GTG CAC TAC ATC GTC TTC ATG GCC ACG CCG       1363
Leu Met Pro Leu Phe Gly Val His Tyr Ile Val Phe Met Ala Thr Pro
410                 415                 420

TAC ACA GAA GTA TCA GGG ATT CTT TGG CAA GTC CAA ATG CAC TAT GAA       1411
Tyr Thr Glu Val Ser Gly Ile Leu Trp Gln Val Gln Met His Tyr Glu
425                 430                 435

ATG CTC TTC AAT TCA TTC CAG GGA TTT TTC GTT GCC ATT ATA TAC TGT       1459
Met Leu Phe Asn Ser Phe Gln Gly Phe Phe Val Ala Ile Ile Tyr Cys
        440                 445                 450

TTC TGC AAT GGA GAG GTA CAA GCA GAG ATC AAG CTG TCA TGG AGC CGA       1507
Phe Cys Asn Gly Glu Val Gln Ala Glu Ile Lys Leu Ser Trp Ser Arg
455                 460                 465                 470

TGG ACC CTG GCC TTG GAC TTC AAG CGG AAG CGG AGT GGC AGC AGT           1555
Trp Thr Leu Ala Leu Asp Phe Lys Arg Lys Arg Ser Gly Ser Ser
        475                 480                 485

ACC TAC AGC TAT GGC CCC ATG GTG TCA CAT ACA AGT GTC ACC AAT GTG       1603
Thr Tyr Ser Tyr Gly Pro Met Val Ser His Thr Ser Val Thr Asn Val
490                 495                 500
```

FIG. 1D

```
GGA CCT CGA GGG GGC TGG CCT TGT CCC TCA GCC CTC GAC TAGCTCCCTGG    1652
Gly Pro Arg Gly Gly Trp Pro Cys Pro Ser Ala Leu Asp
505                          510                    515

GGCTGGAGCC AGTGCCAATG GCCATCACCA GTTGCCTGGC TATGTGAAGC ATGGTTCCAT  1712
TTCTGAGAAC TCATTGCCTT CATCTGGCCC AGAGCCTGGC ACCAAAGATG ACGGGTATCT  1772
CAATGGCTCT GGACTTTATG AGCCAATGGT TGGGGAACAG CCCCCTCCAC TCCTGGAGGA  1832
GGAGAGAGAG ACAGTCATGT GACCCATATC                                   1862
```

FIG. 1E

```
TGGCACAGC CACCCTGTTG GTAGTCCAGG GGCCAGCCCA CTGAGCTGGC ATATCAGCTG         60

GTGGCCCCGT TGGACTCGGC CCTAGGGAAC GGCGGCG ATG GGA GCG CCC CGG ATC        115
                                          Met Gly Ala Pro Arg Ile
                                           1                       5

TCG CAC AGC CTT GCC TTG CTC CTC TGC TGC CTC GTG CTC AGC TCC GTC         163
Ser His Ser Leu Ala Leu Leu Leu Cys Cys Leu Val Leu Ser Ser Val
                     10                      15                      20

TAC GCA CTG GTG GAT GCC GAT GAT GTC ATA ACG AAG GAG GAG CAG ATC         211
Tyr Ala Leu Val Asp Ala Asp Asp Val Ile Thr Lys Glu Glu Gln Ile
             25                      30                      35

ATT CTT CGC AAT GCC CAG GCC CAG TGT GAG CAG CGC CTG AAA GAG             259
Ile Leu Arg Asn Ala Gln Ala Gln Cys Glu Gln Arg Leu Lys Glu
         40                      45                      50

GTC CTC AGG GTC CCT GAA CTT GCT CTA GAA TCT GCC AAA GAC TGG ATG TCA     307
Val Leu Arg Val Pro Glu Leu Ala Leu Glu Ser Ala Lys Asp Trp Met Ser
     55                      60                      65                  70

AGG TCT GCA AAG ACA AAG AAG GAG AAA CCT GCA GAA AAG CTT TAT CCC         355
Arg Ser Ala Lys Thr Lys Lys Glu Lys Pro Ala Glu Lys Leu Tyr Pro
                     75                      80                      85

CAG GCA GAG GAG TCC AGG GAA GTT TCT GAC AGG AGC CGG GAT CAG GAT         403
Gln Ala Glu Glu Ser Arg Glu Val Ser Asp Arg Ser Arg Asp Gln Asp
             90                      95                     100

GGC TTC TGC CTA CCT GAG CCT GAG TGG GAC TGG AAC ATT GTG TGC TGG CCT GGA 451
Gly Phe Cys Leu Pro Glu Pro Glu Trp Asp Trp Asn Ile Val Cys Trp Pro Gly
         105                     110                     115

GTG CCC GGC AAG GTG GTG GCC GTG CCC TGC CCC GAC TAC TTC TAC GAC         499
Val Pro Gly Lys Val Val Ala Val Pro Cys Pro Asp Tyr Phe Tyr Asp
                     120                     125                     130
```

FIG. 2A

```
TTC AAC CAC AAA GGC CGA GCC TAT CGG CGC TGT GAC AGC AAT GGC AGC    547
Phe Asn His Lys Gly Arg Ala Tyr Arg Arg Cys Asp Ser Asn Gly Ser
135                 140                 145                 150

TGG GAG CTG GTG CCT GGG AAC AAC CGG ACA TGG GCG AAT TAC AGC GAA    595
Trp Glu Leu Val Pro Gly Asn Asn Arg Thr Trp Ala Asn Tyr Ser Glu
        155                 160                 165

TGT GTC AAG TTT CTG ACC AAC GAG ACC CGG GAA CGG GAA GTC TTT GAT    643
Cys Val Lys Phe Leu Thr Asn Glu Thr Arg Glu Arg Glu Val Phe Asp
    170                 175                 180

CGC CTC GGA ATG ATC TAC ACT GTG ACT TAC TCC ATC TCT CTG GGC TCC    691
Arg Leu Gly Met Ile Tyr Thr Val Thr Tyr Ser Ile Ser Leu Gly Ser
185                 190                 195

CTC ACT GTG GCT GTG CTG ATT CTG GGT TAC TTT AGG AGG TTA CAT TGC    739
Leu Thr Val Ala Val Leu Ile Leu Gly Tyr Phe Arg Arg Leu His Cys
        200                 205                 210

ACC CGA AAC TAC ATT CAC ATG CAT CTC TTC GTG TCC TTT ATG CTC CGG    787
Thr Arg Asn Tyr Ile His Met His Leu Phe Val Ser Phe Met Leu Arg
    215                 220                 225                 230

GCT GTA AGC ATC TTC ATC AAG GAT GCT GTG CTC TAC TCG GGG GTT TCC    835
Ala Val Ser Ile Phe Ile Lys Asp Ala Val Leu Tyr Ser Gly Val Ser
235                 240                 245
```

FIG. 2B

```
ACA GAT GAA ATC GAG CGC ATC ACC GAG GAG CTG AGG GCC TTC ACA    883
Thr Asp Glu Ile Glu Arg Ile Thr Glu Glu Leu Arg Ala Phe Thr
        250                 255                 260

GAG CCT CCC CCT GCT GAC AAG GCG GGT TTT GTG GGC TGC AGA GTG GCG    931
Glu Pro Pro Pro Ala Asp Lys Ala Gly Phe Val Gly Cys Arg Val Ala
            265                 270                 275

GTA ACC GTC TTC CTT TAC TTC CTG ACC AAC TAC TAC TGG ATC CTG    979
Val Thr Val Phe Leu Tyr Phe Leu Thr Asn Tyr Tyr Trp Ile Leu
        280                 285                 290

GTG GAA GGC CTC TAC CTT CAC AGC CTC ATC TTC ATG GCT TTT TCT   1027
Val Glu Gly Leu Tyr Leu His Ser Leu Ile Phe Met Ala Phe Ser
        295                 300                 305             310

GAG AAA AAG TAT CTC TGG GGT TTC ACA TTA TTT GGC CTC CCT   1075
Glu Lys Lys Tyr Leu Trp Gly Phe Thr Leu Phe Gly Leu Pro
        315                 320                 325

GCC GTG TTT GTC GCT GCT GTG TGG GTG ACC GTG AGG GCT ACA CTG GCC AAC   1123
Ala Val Phe Val Ala Val Trp Val Thr Val Arg Ala Thr Leu Ala Asn
    330                 335                 340

ACT GAG TGC TGG GAC CTG AGT TCG GGG AAT AAG AAA TGG ATC ATA CAG   1171
Thr Glu Cys Trp Asp Leu Ser Ser Gly Asn Lys Lys Trp Ile Ile Gln
    345                 350                 355

GTG CCC ATC CTG GCA GCT ATT GTG GTG AAC TTT ATT CTT TTT ATC AAT   1219
Val Pro Ile Leu Ala Ala Ile Val Val Asn Phe Ile Leu Phe Ile Asn
    360                 365                 370

ATA ATC AGA GTC CTG GCT ACT AAA CTC CGG GAG ACC AAT GCA GGG AGA   1267
Ile Ile Arg Val Leu Ala Thr Lys Leu Arg Glu Thr Asn Ala Gly Arg
375                 380                 385                 390
```

FIG. 2C

```
TGT GAC ACG AGG CAA CAG TAT AGA AAG CTG AAG TCC ACG CTA GTC    1315
Cys Asp Thr Arg Gln Gln Tyr Arg Lys Leu Lys Ser Thr Leu Val
            395                 400                 405

CTC ATG CCG CTA TTT GGG GTG CAC TAC ATC GTC TTC ATG GCC ACG CCG    1363
Leu Met Pro Leu Phe Gly Val His Tyr Ile Val Phe Met Ala Thr Pro
        410                 415                 420

TAC ACA GAA GTA TCA GGG ATT CTT TGG CAA GTC CAA ATG CAC TAT GAA    1411
Tyr Thr Glu Val Ser Gly Ile Leu Trp Gln Val Gln Met His Tyr Glu
        425                 430                 435

ATG CTC TTC AAT TCA TTC CAG GGA TTT TTC GTT GCC ATT ATA TAC TGT    1459
Met Leu Phe Asn Ser Phe Gln Gly Phe Phe Val Ala Ile Ile Tyr Cys
        440                 445                 450

TTC TGC AAT GGA GAG GTA CAA GCA GAG ATC AAG AAG TCA TGG AGC CGA    1507
Phe Cys Asn Gly Glu Val Gln Ala Glu Ile Lys Lys Ser Trp Ser Arg
        455                 460                 465                 470

TGG ACC CTG GCC TTG GAC TTC AAG CGG AAG GCC CGG AGT GGC AGT AGT    1555
Trp Thr Leu Ala Leu Asp Phe Lys Arg Lys Ala Arg Ser Gly Ser Ser
        475                 480                 485

ACC TAC AGC TAT GGC CCC ATG GTG TCA CAT ACA AGT GTC ACC AAT GTG    1603
Thr Tyr Ser Tyr Gly Pro Met Val Ser His Thr Ser Val Thr Asn Val
        490                 495                 500
```

FIG. 2D

```
GGA CCT CGA GGG GGG CTG GCC TTG TCC CTC AGC CCT CGA CTA GCT CCT    1651
Gly Pro Arg Gly Gly Leu Ala Leu Ser Leu Ser Pro Arg Leu Ala Pro
        505             510             515

GGG GCT GGA GCC AGT GCC AAT GGC CAT CAC CAG TTG CCT GGC TAT GTG    1699
Gly Ala Gly Ala Ser Ala Asn Gly His His Gln Leu Pro Gly Tyr Val
        520             525             530

AAG CAT GGT TCC ATT TCT GAG AAC TCA TTG CCT TCA TCT GGC CCA GAG    1747
Lys His Gly Ser Ile Ser Glu Asn Ser Leu Pro Ser Ser Gly Pro Glu
        535             540             545             550

CCT GGC ACC AAA GAT GAC GGG TAT CTC AAT GGC TCT GGA CTT TAT GAG    1795
Pro Gly Thr Lys Asp Asp Gly Tyr Leu Asn Gly Ser Gly Leu Tyr Glu
        555             560             565

CCA ATG GTT GGG GAA CAG CCC CCT CCA CTC CTG GAG GAG AGA GAG        1843
Pro Met Val Gly Glu Gln Pro Pro Pro Leu Leu Glu Glu Arg Glu
        570             575             580

ACA GTC ATG TGACCCATAT C                                           1863
Thr Val Met
        585
```

FIG. 2E

```
GGCGGGGGCC GCGGCGGCGA GCTCGGAGGC CGGCGGGGGC TGCCCCGAGG GACGCGGCCC    60

TAGGCGGTGG CG ATG GGG GCC GCC CGG ATC GCA CCC AGC CTG GCG CTC       108
              Met Gly Ala Ala Arg Ile Ala Pro Ser Leu Ala Leu
               1               5                          10

CTA CTC TGC TGC CCA GTG CTC TCC GCA TAT CTG GTG GCG GAT GCG         156
Leu Leu Cys Cys Pro Val Leu Ser Ala Tyr Leu Val Ala Asp Ala
             15                  20                  25

GAC GAT GTC TTT ACC AAA GAG GAA CAG ATT TTC CTG CAC CGT GCC         204
Asp Asp Val Phe Thr Lys Glu Glu Gln Ile Phe Leu His Arg Ala
        30                  35                  40

CAG GCG CAA TGT GAC AAG CTG CTC AAG GAA GTT CTG CAC ACA GCA GCC     252
Gln Ala Gln Cys Asp Lys Leu Leu Lys Glu Val Leu His Thr Ala Ala
45                  50                  55                  60

AAC ATA ATG GAG TCA GAC AAG GGC TGG ACA CCA GCA TCT ACG TCA GGG     300
Asn Ile Met Glu Ser Asp Lys Gly Trp Thr Pro Ala Ser Thr Ser Gly
                65                  70                  75

AAG CCC AGG AAA GAG AAG AAG TAC CCC ACC TAC CCT GAG TCT AAA         348
Lys Pro Arg Lys Glu Lys Lys Tyr Pro Thr Tyr Pro Glu Ser Lys
        80                  85                  90

GAG AAC AAG GAC GTG AAC ATC GTT TGC TGG GGA AGG CGC CGT TGT         396
Glu Asn Lys Asp Val Asn Ile Val Cys Trp Gly Arg Arg Arg Cys
            95                 100                 105

CTG CCC GAG TGG GAC AAC ATC GTT TGC TGG CCA TTA GGG GCA CCA GGT     444
Leu Pro Glu Trp Asp Asn Ile Val Cys Trp Pro Leu Gly Ala Pro Gly
110                 115                 120

GAA GTG GTG GCA GTA CCT TGT CCC TGT CCC GAT TAC ATT TAT GAC TTC AAT CAC    492
Glu Val Val Ala Val Pro Cys Pro Cys Pro Asp Tyr Ile Tyr Asp Phe Asn His
125                 130                 135                         140

FIG. 3A
```

| | | | | | | | | | |
|---|---|---|---|---|---|---|---|---|---|
| AAA | GGC | CAT | GCC | TAC | AGA | CGC | TGT | GAC | CGC | AAT | GGC | AGC | TGG | GAG | GTG | 540 |
| Lys | Gly | His | Ala | Tyr | Arg | Arg | Cys | Asp | Arg | Asn | Gly | Ser | Trp | Glu | Val | |
| | | | 145 | | | | | 150 | | | | | 155 | | | |

```
AAA GGC CAT GCC TAC AGA CGC TGT GAC CGC AAT GGC AGC TGG GAG GTG   540
Lys Gly His Ala Tyr Arg Arg Cys Asp Arg Asn Gly Ser Trp Glu Val
            145             150             155

GTT CCA GGG CAC AAC CGG ACG TGG GCC AAC TAC AGC GAG TGC CTC AAG   588
Val Pro Gly His Asn Arg Thr Trp Ala Asn Tyr Ser Glu Cys Leu Lys
            160             165             170

TTC ATG ACC AAT GAG ACG CGG GAA ACG CGG GAG GTA TTT GAC CGC CTA GGC   636
Phe Met Thr Asn Glu Thr Arg Glu Thr Arg Glu Val Phe Asp Arg Leu Gly
            175             180             185

ATG ATC TAC ACC GTG GGA TAC TAT TCC ATG TCT CTC GCC TCC CTC ACG GTG   684
Met Ile Tyr Thr Val Gly Tyr Tyr Ser Met Ser Leu Ala Ser Leu Thr Val
            190             195             200

GCT GTG CTC ATC CTG GCC ATG TTC CTG TCG TTT ATG CTG CGC AAC   732
Ala Val Leu Ile Leu Ala Met Phe Leu Ser Phe Met Leu Arg Asn
    205             210             215             220

TAC ATC CAC ATG CAC ATG TTC CTG TCG TTT ATG CTG CGC GCC GCG AGC   780
Tyr Ile His Met His Met Phe Leu Ser Phe Met Leu Arg Ala Ala Ser
            225             230             235

ATC TTC GTG AAG GAC GCT GTG CTC TAC ATC TCT GGC TTC ACG CTG GAT GAG   828
Ile Phe Val Lys Asp Ala Val Leu Tyr Ile Ser Gly Phe Thr Leu Asp Glu
            240             245             250
```

FIG. 3B

| | | | | | | | | | | | | | | | |
|---|---|---|---|---|---|---|---|---|---|---|---|---|---|---|---|
| GCC | GAG | CGC | CTC | ACA | GAG | GAA | GAG | TTG | CAC | ATC | ATC | GCG | CAG | GTG | CCA | 876 |
| Ala | Glu | Arg | Leu | Thr | Glu | Glu | Glu | Leu | His | Ile | Ile | Ala | Gln | Val | Pro |
| 255 | | | | | 260 | | | | | | 265 | | | | |
| CCT | CCG | CCG | GCC | GCT | GCC | GTA | GGC | TAC | GCT | GGC | TAC | GCT | GGC | GTG | GCG |  924 |
| Pro | Pro | Pro | Ala | Ala | Ala | Val | Gly | Tyr | Ala | Gly | Tyr | Ala | Gly | Val | Ala |
| 270 | | | | 275 | | | | | 280 | | | | | | |
| GTG | ACC | TTC | TTC | CTC | TAC | TTC | CTG | GCT | ACC | AAC | TAC | TAC | TGG | ATT | CTG |  972 |
| Val | Thr | Phe | Phe | Leu | Tyr | Phe | Leu | Ala | Thr | Asn | Tyr | Tyr | Trp | Ile | Leu |
| 285 | | | | | 290 | | | | | 295 | | | | | 300 |
| GTG | GAG | GGG | CTG | TAC | TTG | CAC | AGC | CTC | ATC | TTC | ATG | GCC | TTT | TTC | TCA | 1020 |
| Val | Glu | Gly | Leu | Tyr | Leu | His | Ser | Leu | Ile | Phe | Met | Ala | Phe | Phe | Ser |
| 305 | | | | | | 310 | | | | | | | | | 315 |
| GAG | AAG | TAC | CTG | TAC | CTG | TGG | GGC | TTC | ACC | ATC | TTT | GGT | GGT | CTA | CCG | 1068 |
| Glu | Lys | Tyr | Leu | Tyr | Leu | Trp | Gly | Phe | Thr | Ile | Phe | Gly | Trp | Gly | Leu | Pro |
| | 320 | | | | | | | | 325 | | | | | 330 | |
| GCT | GTC | TTC | GTG | GTG | GCT | GTG | TGG | GTC | GGT | GTC | AGA | GCA | ACC | TTG | GCC | AAC | 1116 |
| Ala | Val | Phe | Val | Val | Ala | Val | Trp | Val | Gly | Val | Arg | Ala | Thr | Leu | Ala | Asn |
| 335 | | | | | | 340 | | | | | | | 345 | | | |
| ACT | GGG | TGC | TGG | GAT | CTG | AGC | AGC | TCC | GGG | CAC | AAG | AAG | ATC | ATC | CAG | 1164 |
| Thr | Gly | Cys | Trp | Asp | Leu | Ser | Ser | Ser | Gly | His | Lys | Lys | Ile | Ile | Gln |
| 350 | | | | | 355 | | | | | | | 360 | | | |
| GTG | CCC | ATC | CTG | GCA | TCT | GTT | GTG | CTC | AAC | TTC | ATC | CTT | TTT | ATC | AAC | 1212 |
| Val | Pro | Ile | Leu | Ala | Ser | Val | Val | Leu | Asn | Phe | Ile | Leu | Phe | Ile | Asn |
| 365 | | | | | 370 | | | | | 375 | | | | | 380 |
| ATC | ATC | CGG | GTG | CTT | GCC | ACT | AAG | CTT | CGG | GAG | ACC | AAT | GCG | GGC | CGG | 1260 |
| Ile | Ile | Arg | Val | Leu | Ala | Thr | Lys | Leu | Arg | Glu | Thr | Asn | Ala | Gly | Arg |
| | | | | 385 | | | | | 390 | | | | | 395 | |

FIG. 3C

```
TGT GAC ACC AGG CAG TAC CGG AAG CTG CTC AGG TCC ACG TTG GTG    1308
Cys Asp Thr Arg Gln Tyr Arg Lys Leu Leu Arg Ser Thr Leu Val
            400                 405                 410

CTC GTG CCG CTC TTT GGT GTC CAC TAC ACC GTC TTC ATG GCC TTG CCG    1356
Leu Val Pro Leu Phe Gly Val His Tyr Thr Val Phe Met Ala Leu Pro
        415                 420                 425

TAC ACC GAG GTC TCA GGG ACA TTG CAG ATC CAG ATG CAT TAT GAG    1404
Tyr Thr Glu Val Ser Gly Thr Leu Trp Gln Ile Gln Met His Tyr Glu
    430                 435                 440

ATG CTC TTC AAC TCC TTC CAG GGA TTT GTT GCC ATC ATA TAC TGT    1452
Met Leu Phe Asn Ser Phe Gln Gly Phe Phe Val Ala Ile Ile Tyr Cys
445                 450                 455                 460

TTC TGC AAT GGT GAG GTG CAG GCA GAG ATT AGG AAG TCA TGG AGC CGC    1500
Phe Cys Asn Gly Glu Val Gln Ala Glu Ile Arg Lys Ser Trp Ser Arg
        465                 470                 475

TGG ACA CTG GCG TTG GAC TTC AAG CGC AAA GCA CGA AGT GGG AGT AGC    1548
Trp Thr Leu Ala Leu Asp Phe Lys Arg Lys Ala Arg Ser Gly Ser Ser
    480                 485                 490

AGC TAC AGC TAT GGC CCA ATG GTG TCT CAC ACG AGT ACC AAT GTG    1596
Ser Tyr Ser Tyr Gly Pro Met Val Ser His Thr Ser Thr Asn Val
495                 500                 505
```

FIG. 3D

```
GGC CCC CGT GCA GGA CTC CTC AGC CTC CCC CGC CTG CCT CCT   1644
Gly Pro Arg Ala Gly Leu Leu Ser Leu Pro Arg Leu Pro Pro
        510                 515                 520

GCC ACT ACC AAT GGC CAC TCC CAG CTG CCT GGC CAT GCC AAG CCA GGG   1692
Ala Thr Thr Asn Gly His Ser Gln Leu Pro Gly His Ala Lys Pro Gly
        525                 530                 535             540

GCT CCA GCC ACT GAG ACT GAA ACC CTA CCA GTC ACT ATG GCG GTT CCC   1740
Ala Pro Ala Thr Glu Thr Glu Thr Leu Pro Val Thr Met Ala Val Pro
                545                 550                 555

AAG GAC GAT GGA TTC CTT AAC GGC TCC TGC TCA GGC CTG GAT GAG GAG   1788
Lys Asp Asp Gly Phe Leu Asn Gly Ser Cys Ser Gly Leu Asp Glu Glu
                560                 565                 570

GCC TCC GGG TCT GCG CGG CCG CCT CCA TTG TTG CAG GAA GGA TGG GAA   1836
Ala Ser Gly Ser Ala Arg Pro Pro Pro Leu Leu Gln Glu Gly Trp Glu
        575                 580                 585

ACA GTC ATG TGACTGGGCA CTAGGGGGCT AGACTGCTGG CCTGGGCACA   1885
Thr Val Met
        590

TGGACAGATG GACCAAGAAG CCAGTGTTTG GCTGGTTGTC TATTCGGGAT CTGGACCAGG   1945
AAGATAACAA AAGGAAAATG GAAGTGGACG AAGCAGAGAA GAAGGAAGAG GTTTTGCAGG   2005
AATTAAATAT GTTTCCTCAG AGGACACAAG TGGATGATG GAAGGC   2051
```

FIG. 3E

```
  1 MGAARIAPSLALLLCCPVLSSAYALVDADDVFTKEEQIFLLHRAQAQCDK   50
    |||:||..|||||||||.||||.||||||||||:||||||:||:.|||||:.
  1 MGAPRISHSLALLLCCSVLSSVYALVDADDVITKEEQIILLRNAQAQCEQ   50

51 LLKEVLHTAANIMESDKGWTPASTSGKPRKEKASGKFYPESKENKDVPTG  100
    |||||:  .:::  ||.|:|    |  |:|.:|||:..:|:||:...|.::|..
 51 RLKEVLR.VPELAESAKDW..MSRSAKTKKEKPAEKLYPQAEESREVSDR   97

101 SRRRGRPCLPEWDNIVCWPLGAPGEVVAVPCPDYIYDFNHKGHAYRRCDR  150
    ||  ..:   ||||||||||||  |.||.|||||||||:||||||:||||||.
 98 SRLQDGFCLPEWDNIVCWPAGVPGKVVAVPCPDYFYDFNHKGRAYRRCDS  147

151 NGSWEVVPGHNRTWANYSECLKFMTNETREREVFDRLGMIYTVGYSMSLA  200
    |||||:|||:|||||||||||:|||||||||||||||||||||||||||:||:
148 NGSWELVPGNNRTWANYSECVKFLTNETREREVFDRLGMIYTVGYSISLG  197

201 SLTVAVLILAYFRRLHCTRNYIHMHMFLSFMLRAASIFVKDAVLYSGFTL  250
    ||||||||:||||||||||||||||||:|:|||||.|||:||||||||..
198 SLTVAVLILGYFRRLHCTRNYIHMHLFVSFMLRAVSIFIKDAVLYSGVST  247

251 DEAERLTEEELHIIAQVPPPPAAAAVGYAGCRVAVTFFLYFLATNYYWIL  300
    ||  ||:|||||: :..:    ||:|. .|:.|||||||.|||||.|||||||
248 DEIERITEEELRAFTE...PPPADKAGFVGCRVAVTVFLYFLTTNYYWIL  294

301 VEGLYLHSLIFMAFFSEKKYLWGFTIFGWGLPAVFVAVWVGVRATLANTG  350
    ||||||||||||||||||||||||||:||||||||||||||.||||||||:
295 VEGLYLHSLIFMAFFSEKKYLWGFTLFGWGLPAVFVAVWVTVRATLANTE  344

351 CWDLSSGHKKWIIQVPILASVVLNFILFINIIRVLATKLRETNAGRCDTR  400
    |||||||:||||||||||.:|:|||||||||||||||||||||||||||
345 CWDLSSGNKKWIIQVPILAAIVVNFILFINIIRVLATKLRETNAGRCDTR  394

401 QQYRKLLRSTLVLVPLFGVHYTVFMALPYTEVSGTLWQIQMHYEMLFNSF  450
    |||||||:||||||:|||||||.||||  |||||||.|||:|||||||||||
395 QQYRKLLKSTLVLMPLFGVHYIVFMATPYTEVSGILWQVQMHYEMLFNSF  444

451 QGFFVAIIYCFCNGEVQAEIRKSWSRWTLALDFKRKARSGSSSYSYGPMV  500
    |||||||||||||||||||:|||||||||||||||||||||||.|||||||
445 QGFFVAIIYCFCNGEVQAEIKKSWSRWTLALDFKRKARSGSSTYSYGPMV  494

501 SHTSVTNVGPRAGLSLPLSPRLPP...ATTNGHSQLPGHAKPGAPATETE  547
    ||||||||||||:||.|.||||||:|   |..|||  ||||..|.|.  ..:.
495 SHTSVTNVGPRGGLALSLSPRLAPGAGASANGMHQLPGYVKHGSISENSL  544

548 TLPVTMAVPKDDGFLNGSCSGLDEEASGSARPPPLLQEGWETVM  591
    . ... :..||||:|||  |||  |.   |  ..|||||:|::||||
545 PSSGPEPGTKDDGYLNG..SGLYEPMVG.EQPPPLLEEERETVM  585
```

| Gap Weight: | 3.000 | Average Match: | 0.540 |
|---|---|---|---|
| Length Weight: | 0.100 | Average Mismatch: | -0.396 |
| Quality: | 712.2 | Length: | 594 |
| Ratio: | 1.215 | Gaps: | 6 |
| Percent Similarity: | 87.113 | Percent Identity: | 77.835 |

FIG. 4

```
                                                              *
R15   MGAARIAPSL ALLLCCPVLS SAYALVDADD VFTKEEQIFL LHRAQAQCDK  50
Oko   MGAPRISHSL ALLLCCSVLS SVYALVDADD VITKEEQIIL LRNAQAQCEQ  50
Okh   MGAPRISHSL ALLLCCSVLS SVYALVDADD VITKEEQIIL LRNAQAQCEQ  50
                 --------- A ---------

R15   LLKEVLHTAA NIMESDKGWT PASTSGKPRK EKASGKFYPE SKENKDVPTC 100
Oko   RLKEVLR.VP ELAESAKDW. .MSRSAKTKK EKPAEKLYPQ AEESREVSDR  97
Okh   RLKEVLR.VP ELAESAKDW. .MSRSAKTKK EKPAEKLYPQ AEESREVSDR  97

*           *              *            *
R15   SRRRGRPCLP EWDNIVCWPL GAPGEVVAVP CPDYIYDFNH KGHAYRRCDR 150
Oko   SRLQDGFCLP EWDINVCWPA GVPGKVVAVP CPDYFYDFNH KGRAYRRCDS 147
Okh   SRLQDGFCLP EWDNIVCWPA GVPGKVVAVP CPDYFYDFNH KGRAYRRCDS 147
                          --------- B ---------

N          N  N    *           N
R15   NGSWEVVPGH NRTWANYSEC LKFMTNETRE REVFDRLGMI YTVGYSMSLA 200
Oko   NGSWELVPGN NRTWANYSEC VKFLTNETRE REVFDRLGMI YTVGYSISLG 197
Okh   NGSWELVPGN NRTWANYSEC VKFLTNETRE REVFDRLGMI YTVGYSISLG 197
                                                 ----------

R15   SLTVAVLILA YFRRLHCTRN YIHMHMFLSF MLRAASIFVK DAVLYSGFTL 250
Oko   SLTVAVLILG YFRRLHCTRN HIHMHLFVSF MLRAVSIFIK DAVLYSGVST 247
Okh   SLTVAVLILG YFRRLHCTRN YIHMHLFVSF MLRAVSIFIK DAVLYSGVST 247
      -- C ---------                  ---------- D ----------

*
R15   DEAERLTEEE LHIIAQVPPP PAAAAVGYAG CRVAVTFFLY FLATNYYWIL 300
Oko   DEIERITEEE LRAFTE...P PPADKAGFVG CRVAVTVFLY FLTTNYYWIL 294
Okh   DEIERITEEE LRAFLT...P PPADKAGFVG CRVAVTVFLY FLTTNYYWIL 294
                                  --------- E ---------   ---

R15   VEGLYLHSLI FMAFFSEKKY LWGFTLFGWG LPAVFVAVWV GVRATLANTG 350
Oko   VEGLYLHSLI FMAFFSEKKY LWGFTLFGWG LPAVFVAVWV TVRATLANTE 344
Okh   VEGLYLHSLI FMAFFSEKKY LWGFTLFGWG LPAVFVAVWV TVRATLANTE 344
      ---- F ----------            -------- G ---------
      *
R15   CWDLSSGHKK WIIQVPILAS VVLNFILFIN IIRVLATKLR ETNAGRCDTR 400
Oko   CWDLSSGNKK WIIQVPILAA IVVNFILFIN IIRVLATKLR ETNAGRCDTR 394
Okh   CWDLSSGNKK WIIQVPILAA IVVNFILFIN IIRVLATKLR ETNAGRCDTR 394
                     --------- H ---------

R15   QQYRKLLRST LVLVPLFGVH YTVFMALPYT EVSGTGWQIQ MHYEMLFNSF 450
Oko   QQYRKLLKST LVLMPLFGVH YIVFMATPYT EVSGILWQVQ MHYEMLFNSF 444
Okh   QQYRKLLKST LVLMPLFGVH YIVFMATPYT EVSGILWQVQ MHYEMLFNSF 444
                 --------- I ---------                   ------

R15   QGFFVAIIYC FCNGEVQAEI RKSWSRWTLA LDFKRKARSG SSSYSYGPMV 500
Oko   QGFFVAIIYC FCNGEVQAEI KKSWSRWTLA LDFKRKARSG SSTYSYGPMV 494
Okh   QGFFVAIIYC FCNGEVQAEI KKSWSRWTLA LDFKRKARSG SSTYSYGPMV 494
      -- J ---------

R15   SHTSVTNVGP RAGLSLPLSP RLPP...ATT NGHSQLPGHA KPGAPATETE 547
Oko   SHTSVTNVGP RGGLALSLSP RLAPGAGASA NGHHQLPGYV KHGSISENSL 544
Okh   SHTSVTNVGP RGG....... ....WPCPSA LD                   515

R15   TLPVTMAVPK DDGFLNGSCS GLDEEASGSA RPPPLLQEGW ETVM        591
Oko   PSSGPEPGTK DDGYLNG..S GLYEPMVG.E QPPPLLEEER ETVM        585
```

FIG. 5

With I enzymes: SACI

```
     GGGATCCCGCGGGCCCTAGGCGGTGGCGatgggGAccGCcccgatcgcaccggcctggcg
2    ||||||||||||||||||||||||||||||||||||||||||||||||||||||||||||  61
     CCCTAGGGGCGCCCGGGATCCGCCACCGCtaccCTggCGggcctagcgtgggccgaccgc
                                M  G  T  A  R  I  A  P  G  L  A ctcctgctctgtgcccgtgctcagctccgcgtacgcgctggtgatgcagatgacgtc
62   ||||||||||||||||||||||||||||||||||||||||||||||||||||||||||||  121
     gaggacgagacgacgggacacgagtcgaggcgcatgcgcgaccacctacgtctactgcag
     L  L  L  C  C  P  V  L  S  S  A  Y  A  L  V  D  A  D  D  V atgactaaagaggaacagatcttcctgctgcaccgtgctcaggcccagtgcgaaaaacgg
122  ||||||||||||||||||||||||||||||||||||||||||||||||||||||||||||  181
     tactgattctccttgtctagaaggacgacctttcacgagtccgggtcacgcttttgcc
     M  T  K  E  E  Q  I  F  L  L  H  R  A  Q  A  Q  C  E  K  R ctcaaggagtcctgcagagccagcatatgaatcagacaaggatggacatct
182  ||||||||||||||||||||||||||||||||||||||||||||||||||||||||||||  241
     gagttcctccaggacgtctccgtcgcgtattacttagtctgttccctacctgtaga
     L  K  E  V  L  Q  R  P  A  S  I  M  E  S  D  K  G  W  T  S gcgtccacatcaggaggaagcccaggaagataaggcatctgggaagctctaccctgagtct
242  ||||||||||||||||||||||||||||||||||||||||||||||||||||||||||||  301
     cgcaggtgtagtccccttaggtcccttcctattccgtagaccttcgagatggagactcaga
     A  S  T  S  G  K  P  R  K  D  K  A  S  G  K  L  Y  P  E  S
```

FIG. 6A

```
302  gaggaggacaaggaggaggcaccactggcagcaggagggcgccctgtctgccgaa  361
     ||||||||||||||||||||||||||||||||||||||||||||||||||||||
     ctcctcctgttcctccgtggtgaccctcctccatgctcccgcggggacagacgcctt

E   E   D   K   E   A   P   T   G   S   -  .  R   G   R   P   C   L   P   E 362  tgggaccacatcctgtgctggccgctggggggcactggtgagtgtggctgtgccctgt  421
     ||||||||||||||||||||||||||||||||||||||||||||||||||||||
     accctggtgtaggacacgacggcgaccggcgaccccgtggtccactccaccacggaca

W   D   H   I   L   C   W   P   L   G   A   P   G   E   V   V   A   V   P   C 422  ccggactacatttatgacttcaatcacaaaggccatgctaccgacgctgtgaccgcaat  481
     ||||||||||||||||||||||||||||||||||||||||||||||||||||||
     ggcctgatgtaaatactgaagttagtgttccggtacgatgctgcgacactggcgtta

P   D   Y   I   Y   D   F   N   H   K   G   H   A   Y   R   R   C   D   R   N 482  ggcagctgggagctggtgcctgggcacaacagacgtgggccaactacagcgagtgtc  541
     ||||||||||||||||||||||||||||||||||||||||||||||||||||||
     ccgtcgacccctcgaccacgaccacccgtgttgtcctgcaccccgtttgatgtcgctcacacag
```

FIG. 6B

```
     G  S  W  E  L  V  P  G  H  N  R  T  W  A  N  Y  S  E  C  V
     aaattctcaccaacgagactcgtgaacggagtgtttgaccgcctgggcatcatttac
542  ------------------------------------------------------------  601
     tttaagagtggttactctgagcacttgccctccacaaactggcggaccctactaaatg K  F  L  T  N  E  T  R  E  R  E  V  F  D  R  L  G  M  I  Y
     accgtgggctactccgtgtccctggcgtccctcaccgtgtgctcatcctggcctac
602  ------------------------------------------------------------  661
     tggcacccgatgaggcacaggagcaggagtggcatcgacacgagtaggaccggatg T  V  G  Y  S  V  S  L  A  S  L  T  V  A  V  L  I  L  A  Y
     tttaggcggctgcactgcacgcgcaactacatccacatgcacctgttcctgtccttcatg
662  ------------------------------------------------------------  721
     aaatccgccgactgacgtgcgcgttgatgtaggtgtgtacgtggacaaggacaggaagtac F  R  R  L  H  C  T  R  N  Y  I  H  M  H  L  F  L  S  F  M
     ctgcgcgccgtgagcatcttcgtcaaggacgctgtgctctactctggccacgcttgat
722  ------------------------------------------------------------  781
     gacgcggcgcactcgtagaagcagttcctgcgacacgagatgagaccgcggtgcgaacta

```
782  gaggctgagcgcctcaccgagaggagagctgcgcgccatcgccgcccaggcgccccgccgcct   841
     ctccgactcgcggagtggctcctcgacgcgcgcgtagcggtccgcggggcggcgga         —
     E   A   E   R   L   T   E   E   E   L   R   A   I   A   Q   A   P   P   P   P 842  gccaccgcgccgctgccgcggctacgcgcggctccaggtgctgtgacctcttccttacttc   901
     cggtggcggcgacggcgacgccgatgcgcccgacgtcccaccgactggaagaaggaaatgaag  —
     A   T   A   A   A   G   Y   A   G   C   R   V   A   V   T   F   F   L   Y   F 902  ctggccaccaactactactgattctggtggagggctgtacctgcacagcctcatcttc     961
     gaccggtggttgatgatgactaagacctcccgacatgacgtgttggagtagaag          —
     L   A   T   N   Y   Y   W   I   L   V   E   G   L   Y   L   H   G   L   I   F 962  atggcttcttcttcagagagaagtctgtggggcttcacagtcttcggctggggtctg     1021
     taccgaagagagtctcttcttcatggacacccgaagtgtcagaagccgaccccagac       —
     M   A   F   F   S   E   K   K   Y   L   W   G   F   T   V   F   G   W   G   L 1022 cccgctgtcttcgtggctgtgtgggtcagtgtcagagctaccctggccaacaccggggtgc   1081
     gggcgacagaagcaccgacacacccagtcacagtcagatcgatggaccgttgtggccacg    —
                                                                     s
                                                                     a
                                                                     c
     P   A   V   F   V   A   V   W   V   S   Y   R   A   T   L   A   N   T   G   C

FIG. 6D
```

```
1082  tggacttgagctccgggaacaaaagtggatcatccaggtgcccatcctgcctccatt  1141
      ||||||||||||||||||||||||||||||||||||||||||||||||||||||||||
      acctgaactcgaggccctgttttcactagcaggtccacggtaggaccggaggtaa
       W  D  L  S  G  G  N  K  K  W  I  I  Q  V  P  I  L  A  S  I 1142  gtgctcaacttcatctcttcatcaatatcgtccgggtgctcgccaccaagcagcgggag  1201
      ||||||||||||||||||||||||||||||||||||||||||||||||||||||||||
      cacgagttgaagtaggagaagtagtatagcaggcccacgagcggttcgtcgccctc
       V  L  N  F  I  L  F  I  N  I  V  R  V  L  A  T  K  Q  R  E 1202  accaacgccggcggtgtgacacacggcagcagtaccggaagctgctcaaatccacgctg  1261
      ||||||||||||||||||||||||||||||||||||||||||||||||||||||||||
      tggttgcggccggccacactgtgtgccgtcgtcatggccttcgacgagttaggtgcgac
       T  N  A  G  R  C  D  T  R  Q  Q  Y  R  K  L  L  K  S  T  L 1262  gtgctcatgcccctcttttggcgtccactacattgtcttcatggccacaccatacaccgag  1321
      ||||||||||||||||||||||||||||||||||||||||||||||||||||||||||
      cacgagtacggggagaaaccggcagtgatgtaacagagtaccggtgtgtatgtggctc
       V  L  M  P  L  F  G  V  H  Y  I  V  F  M  A  T  P  Y  T  E 1322  gtctcaggacgctctgcaagtccagatgcactatgagatgctcttcaactccttccag  1381
      ||||||||||||||||||||||||||||||||||||||||||||||||||||||||||
      cagagtccctgcgagaccgttcaggtcatactctacgagaagttgaggaaggtc
       V  S  G  T  L  W  Q  V  Q  M  H  Y  E  M  L  F  N  S  F  Q
```

FIG. 6E

```
1382  ggattttttgtcgcaatcatatactgtttctgcaatggcgaggtacaagctgagatcaag  1441
      ||||||||||||||||||||||||||||||||||||||||||||||||||||||||||||
      cctaaaaacagcgttagtatatgacaaagacgttaccgctccatgttcgactctagttc

G   F   F   V   A   I   I   Y   C   F   C   N   G   E   V   Q   A   E   I   K 1442  aaatcttggagccgctggacactggacttcaagcgaaaggcacgcagcggggagc  1501
      ||||||||||||||||||||||||||||||||||||||||||||||||||||||
      tttagaacctcggacctgtgaccgtgacctgaagttcgctttccgagcgtcgccctcg

K   S   W   S   R   W   T   L   A   L   I   F   K   R   K   A   R   S   G   S 1502  agcagctatagctacggcccccatgtgtcccacacaagtgtgaccaatgtcggcccccgt  1561
      ||||||||||||||||||||||||||||||||||||||||||||||||||||||||||||
      tcgtcgatatcgatgccgggggtaccacaggggtgttgttcacactggttacagccggggca

S   S   Y   S   Y   G   P   M   V   S   H   P   S   V   T   N   V   G   P   R 1562  gtgggactcggcctgccctcagccccgcctactgccactgccaccaacggccac  1621
      |||||||||||||||||||||||||||||||||||||||||||||||||||||||
      caccctgagccggacggagtcggggcggatgacggtgacggtggtggttgccggtg

V   G   L   G   L   P   L   S   P   R   L   L   P   T   A   T   T   N   G   H 1622  cctcagctgcctggccatgccaagccaggaccccagcccctgagacccctcgagaccaca  1681
      ||||||||||||||||||||||||||||||||||||||||||||||||||||||||||||
      ggagtcgacggactggccatgccaagccaggaccccagcccctgagacccctcgagaccaca
      ggagtcgacggactggccgttcggttcgtccctgggtcgggaccctctgggagctctggtgt P   Q   L   P   G   H   A   K   P   G   T   P   A   L   E   T   L   E   T   T
```

FIG. 6F

```
1682  ccacctgttatggctgctcctccaaggacgatgggttcctcaacggctcctgctcaggcctg  1741
      ggtggacggtaccgaccaggttcctgctaccaaggagttgccgaggacgagtccggac
       P  P  A  M  A  A  P  K  D  D  G  F  L  N  G  S  C  S  G  L 1742  gacgaggaggcctctgggcctgagcggccacctgccctgctacaggaagagtgggagaca  1801
      ctgctcctccggagaccccgactcgccggtggacggacgatgtcctttctcaccctctgt
       D  E  E  A  S  F  P  E  R  R  P  P  A  L  L  Q  E  E  W  E  T 1802  gtcatgtgaccaggcgctggggctggacctgctgacatagtggacagatggacca  1861
      cagtacactgtccgcgaccccgacctgactgtatcacctacctgtctacctggt
       V  M 1862  aaagatgggtggttgaatgattcccactcagggcctggggcctgaggaaaacaggg  1921
      tttctacccaccaacttactaagggtgagtcccgaccccggttctccttttgtccc 1922  gaaaaagaaaaaaaaaagaaaaaaaggaaaaaaaaaaaaaaaaaaaaaaaaaaaaaa  1981
      cttttcttttttttttctttttttccttttttttttttttttttttttttttttt 1982  aaaaaaaaaaaaaaaaaaaaaaaaaa  2011
      tttttttttttttttttttttttttt
```

Enzymes that do cut:

SacI

FIG. 6G

PARATHYROID HORMONE RECEPTOR BINDING METHOD

This application is a divisional of U.S. application Ser. No. 08/471,494, filed Jun. 6, 1995 now U.S. Pat. No. 5,840,853, and a continuation of U.S. application Ser. No. 08/468,249, filed Jun. 6, 1995, now U.S. Pat. No. 5,886,148, both of which are divisionals of U.S. application Ser. No. 07/864,475, filed Apr. 6, 1992, now U.S. Pat. No. 5,494,806, which is a continuation-in-part of U.S. application Ser. No. 07/681,702, filed Apr. 5, 1991, and now abandoned.

BACKGROUND OF THE INVENTION

Partial funding of the work described herein was provided by the U.S. Government, which has certain rights to the invention.

The invention relates to endocrine receptors.

A crucial step in the expression of hormonal action is the interaction of hormones with receptors on the plasma membrane surface of target cells. The formation of hormone-receptor complexes allows the transduction of extracellular signals into the cell to elicit a variety of biological responses. For example, binding of a hormone such as follicle stimulating hormone (FSH), luteinizing hormone (LH), thyroid stimulating hormone (TSH), and chorionic gonadotropin (CG), to its cell surface receptor induces a conformational change in the receptor, resulting in the association of the receptor with a transductor molecule, the stimulatory guanine nucleotide (GTP) binding protein, a component of which is ($G_s$). This association stimulates adenylate cyclase activity which in turn triggers other cellular processes such as protein phosphorylation, steroid synthesis and secretion, and the modulation of ion flux. Binding of other hormones, including arginine vasopressin (VP), angiotensin II, and norepinephrine, to their cell surface receptors results in the activation of other types of GTP binding proteins components such as ($G_p$), which in turn stimulates the activity or the enzyme phospholipase C. The products of phospholipase C hydrolysis initiate a complex cascade of cellular events, including the mobilization of intracellular calcium and protein phosphorylation.

Parathyroid hormone (PTH) is a major regulator of calcium homeostasis whose principal target cells occur in bone and kidney. Regulation of calcium concentration is necessary for the normal function of the gastrointestinal, skeletal, neurologic, neuromuscular, and cardiovascular systems. PTH synthesis and release are controlled principally by the serum calcium level: a low level stimulates and a high level suppresses both the hormone synthesis and release. PTH, in turn, maintains the serum calcium level by directly or indirectly promoting calcium entry into the blood at three sites of calcium exchange: gut, bone and kidney. PTH contributes to net gastrointestinal absorption of calcium by favoring the renal synthesis of the active form of vitamin D. PTH promotes calcium resorption from bone by inhibiting osteoblasts and, indirectly, by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH exerts these effects primarily through receptor-mediated activation of adenylate cyclase, although receptor-mediated activation of phospholipase C by PTH has also been reported (Hruska et al., J. Clin. Invest. 79:230, 1987).

Disruption of calcium homeostasis may produce many clinical disorders (e.g., severe bone disease, anemia, renal impairment, ulcers, myopathy, and neuropathy) and usually results from conditions which produce an alteration in the level of parathyroid hormone. Hypercalcemia is a condition which is characterized by an elevation in the serum calcium level. It is often associated with primary hyperparathyroidism in which an excess of PTH production occurs as a result of a lesion (e.g., adenoma, hyperplasia or carcinoma) of the parathyroid glands. Another type of hypercalcemia, humoral hypercalcemia of malignancy (HHM), is the most common paraneoplastic syndrome. It appears to result in most instances from the production by tumors (e.g., squamous, renal, ovarian or bladder carcinomas) of a novel class of protein hormone which shares amino acid homology with PTH. These PTH-related proteins (PTHrP) appear to mimic certain of the renal and skeletal actions of PTH and are believed to interact with the PTH receptor in these tissues. PTHrP is normally found at low levels in many tissues, including keratinocytes, brain, pituitary, parathyroid, adrenal cortex, medulla, fetal liver, osteoblast-like cells and lactating mammary tissues. In many HHM malignancies, PTHrP is found in the circulatory system at high levels, thereby producing the elevated calcium levels associated with HHM.

SUMMARY OF THE INVENTION

The invention features isolated DNA comprising a DNA sequence encoding a cell receptor, preferably a parathyroid hormone receptor, of a vertebrate animal, which receptor has an amino acid sequence with at least 30% (preferably at least 50%, even more preferably at least 60%, and most preferably at least 75%) identity to the amino acid sequence shown in FIGS. 3A–E (SEQ ID NO.: 20): i.e., when the closest match is made between the two amino acid sequences (using standard methods), at least 30% of the amino acid residues of the former sequence are identical to the amino acid residues of the latter sequence. By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA, cDNA, recombinant hybrid DNA, or synthetic DNA. It may be identical to a naturally-occurring, cell receptor- (e.g. PTH receptor) encoding DNA sequence, or may differ from such sequence by the deletion, addition, or substitution of one or more nucleotides. Single-stranded DNAs of the invention are generally at least 8 nucleotides long, (preferably at least 18 nucleotides long, and more preferably at least 30 nucleotides long) ranging up to full length of the gene or cDNA; they preferably are detectably labelled for use as hybridization probes, and may be antisense. Preferably, the isolated DNA hybridizes under conditions of high stringency to all or part of the DNA sequence show in FIGS. 1A–E (SEQ ID NO.:1), FIGS. 2A–E (SEQ ID NO.:2), FIGS. 3A–E (SEQ ID NO.:3), or FIGS. 6A–G (SEQ ID NO.:4). By "high stringency" is meant, for example, conditions such as those described herein below for the isolation of human kidney PTH receptor cDNA (also see Current Protocols in Molecular Biology, John Wiley & Sons, New York, 1989, hereby incorporated by reference). Most preferably, the animal is a mammal (such as an opossum, a rat, or a human), and the DNA sequence encodes substantially all of the amino acid sequence shown in FIGS. 1A–E (SEQ ID NO.:1), FIGS. 2A–E (SEQ ID NO.:2), FIGS. 3A–E (SEQ ID NO.:3) or FIGS. 6A–G (SEQ ID NO.:4); or is encoded by the coding sequence of one of the plasmids deposited with the American Type Culture Collection (ATCC) and designated ATCC Accession No. 68570 or 68571. The DNA of the invention may be incorporated into a vector [which may be provided as a purified preparation (e.g., a vector separated from the mixture of vectors which make up a library)] containing a DNA sequence encoding a cell receptor of the invention (e.g. parathyroid hormone receptor) or fragment of the receptor, and a cell or essentially homogenous population of cells (e.g., prokaryotic cells, or eukaryotic cells such as mammalian cells) which contain the vector (or the isolated DNA described above). By "essentially homogenous" is meant that at least 99% of the cells contain the vector of the invention (or the isolated DNA, as the case may be). Preferably, this vector (e.g., R15B) is capable of directing expression of a parathyroid hormone receptor (for example, in a cell transfected or transformed with the vector).

In another aspect, the invention features a cell receptor, preferably parathyroid hormone receptor, (or an essentially purified preparation thereof) produced by expression of a recombinant DNA molecule encoding the cell receptor. An "essentially purified preparation" is one which is substantially free of the proteins and lipids with which it is naturally associated.

In a related aspect, the invention features a polypeptide which includes a fragment of a naturally-occurring cell receptor of the invention. Preferably, the polypeptide includes a fragment of a naturally-occurring parathyroid hormone receptor which is capable of binding parathyroid hormone or parathyroid hormone-related protein. In preferred embodiments, this fragment is at least six amino acids long, and has a sequence selected from the group including:

(a) TNETREREVFDRLGMIYTVG; (SEQ ID NO.: 5)
(b) YLYSGFTLDEAERLTEEEL; (SEQ ID NO.: 6)
(c) VTFFLYFLATNYYWILVEG; (SEQ ID NO.: 7)
(d) Y-RATLANTGCWDLSSGHKKWIIQVP; (SEQ. ID NO.: 8)
(e) PYTEYSGTLWQIQMHYEM; (SEQ ID NO.: 9)
(f) DDVFTKEEQIFLLHRAQA; (SEQ ID NO.: 10)
(g) FFRLHCTRNY; (SEQ ID NO.: 11)
(h) EKKYLWGFTL; (SEQ ID NO.: 12)
(i) VLATKLRETNAGRCDTRQQYRKLLK; or (SEQ ID NO. 13)
(j) a fragment (i.e., a portion at least six residues long, but less than all) or analog of (a)–(i) which is capable of binding parathyroid hormone or parathyroid hormone-related protein [wherein "analog" denotes a peptide having a sequence at least 50% (and preferably at least 70%) identical to the peptide of which it is an analog]. Preferably, the polypeptide of the invention is produced by expression of a recombinant DNA molecule or is synthetic (i.e., assembled by chemical rather than biological means). The invention provides a method for producing such a polypeptide, which method includes providing a cell containing isolated DNA encoding a cell receptor of the invention or receptor fragment and culturing this cell under conditions which permit expression of a polypeptide from the isolated DNA.

The invention also features an antibody (monoclonal or polygonal), and a purified preparation of an antibody, which is capable of forming an immune complex with a cell receptor of the invention (preferably a parathyroid hormone receptor such as a human PTH receptor) such antibody being generated by using as antigen either (1) a polypeptide that includes a fragment of the cell receptor of the invention, or (2) a cell receptor of the invention which is on the surface of a cell. This antibody is preferably capable of neutralizing (i.e., partially or completely inhibiting) a biological activity of the cell receptor of the invention (i.e., a component of one of the cascades naturally triggered by the receptor when its ligand binds to it). In preferred embodiments, the antibody of the invention is capable of forming an immune complex with parathyroid hormone receptor and is capable of neutralizing a biological activity of the PTH receptor (i.e. adenylate cyclase activation or phospholipase C stimulation)

Also within the invention is a therapeutic composition including, in a pharmaceutically-acceptable carrier, (a) a cell receptor of the invention, (b) a polypeptide containing a fragment of the cell receptor of the invention, or (c) an antibody to a cell receptor of the invention. These therapeutic compositions provide a means for treating various disorders characterized by overstimulation of the cell receptors of the invention by their ligand. In preferred embodiments, the polypeptides of the invention include the PTH receptor, fragments of the PTH receptor and antibodies which form immune complexes with the PTH receptor. These polypeptides and antibodies are useful as diagnostics, for distinguishing those cases of hypercalcemia related to PTH or PTHrP from those which are not.

The nucleic acid probes of the invention enable one of ordinary skill in the art of genetic engineering to identify and clone cell receptor homologs or cell receptors from any species which are related to the cell receptors of the invention, expanding the usefulness of the sequences of the invention.

Other features and advantages of the invention will be apparent from the following description of the preferred embodiments and from the claims.

DETAILED DESCRIPTION

The drawings will first be briefly described.

DRAWINGS

FIGS. 1A–E, inclusive, are is a representation of the nucleic acid (SEQ ID NO:1) and amino acid (SEQ ID NO:18) sequence encoding the opossum kidney PTH/PTHrP receptor clone, OK-H.

FIGS. 2A–E, inclusive, are a representation of the nucleic acid (SEQ ID NO:2) and amino acid (SEQ ID NO:19) sequences for the opossum kidney PTH/PTHrp receptor clone, OK-O.

FIGS. 3A–E, inclusive, are a representation of the nucleic acid (SEQ ID NO:3) and amino acid (SEQ ID NO:20) sequences for the rat bone PTH/PTHrP receptor clone, R15B.

FIG. 4 is a comparison of the deduced amino acid sequences of R15B (SEQ ID NO:20) (top line) and OK-O (SEQ ID NO:19) (bottom line) encoded by cDNAs from clones OK-O (SEQ ID NO:2) and R15B (SEQ ID NO:3).

FIG. 5 is a comparison of the deduced amino acid sequences of OK-O (SEQ ID NO:19), OK-H (SEQ ID NO:18) and R15B (SEQ ID NO:20), lined up according to sequence homology.

FIGS. 6A–E, inclusive, are a representation of the nucleic acid (SEQ ID NO:4) and amino acid (SEQ ID NO:21) sequences for the human PTH/PTHrP receptor.

Figure 7:
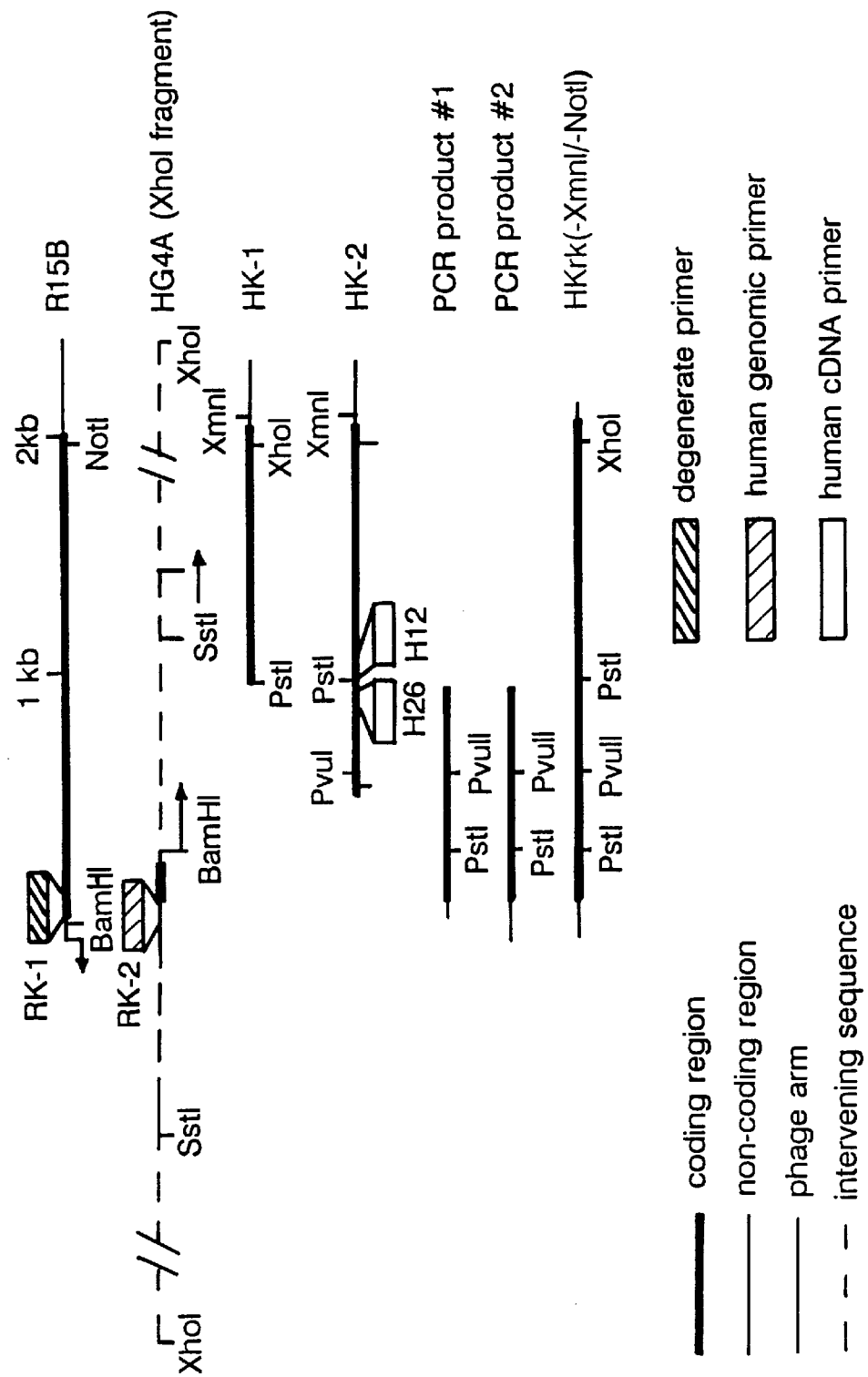

FIG. 7 is a schematic representation of the rat bone PTH/PTHrP receptor cDNA, the human genomic DNA clone HPG1 and two cDNA clones encoding the human PTH/PTHrP receptor.

Figure 8:
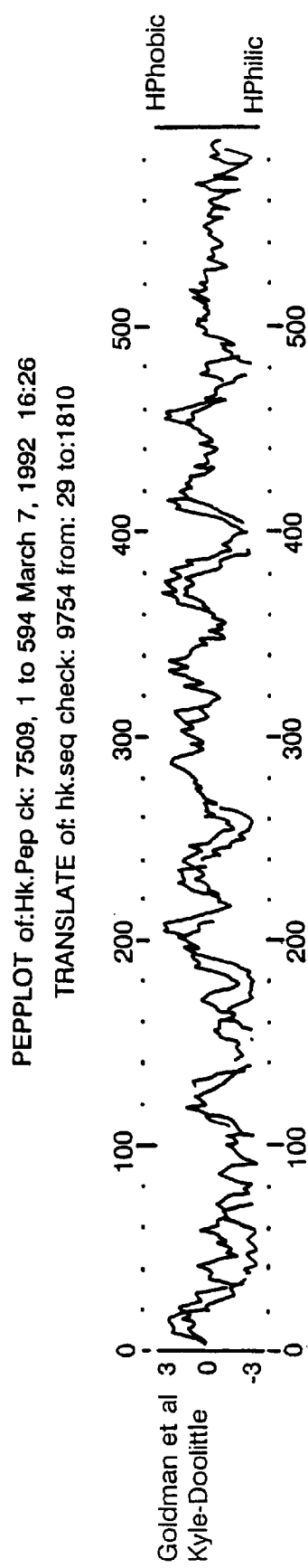

FIG. 8 is a hydrophobicity plot of the deduced amino acid sequence of the human kidney PTH/PTHrP receptor. Predicted membrane-spanning domains I through VII are indicated; A, B and C indicate additional hydrophobic regions.

Figure 9:
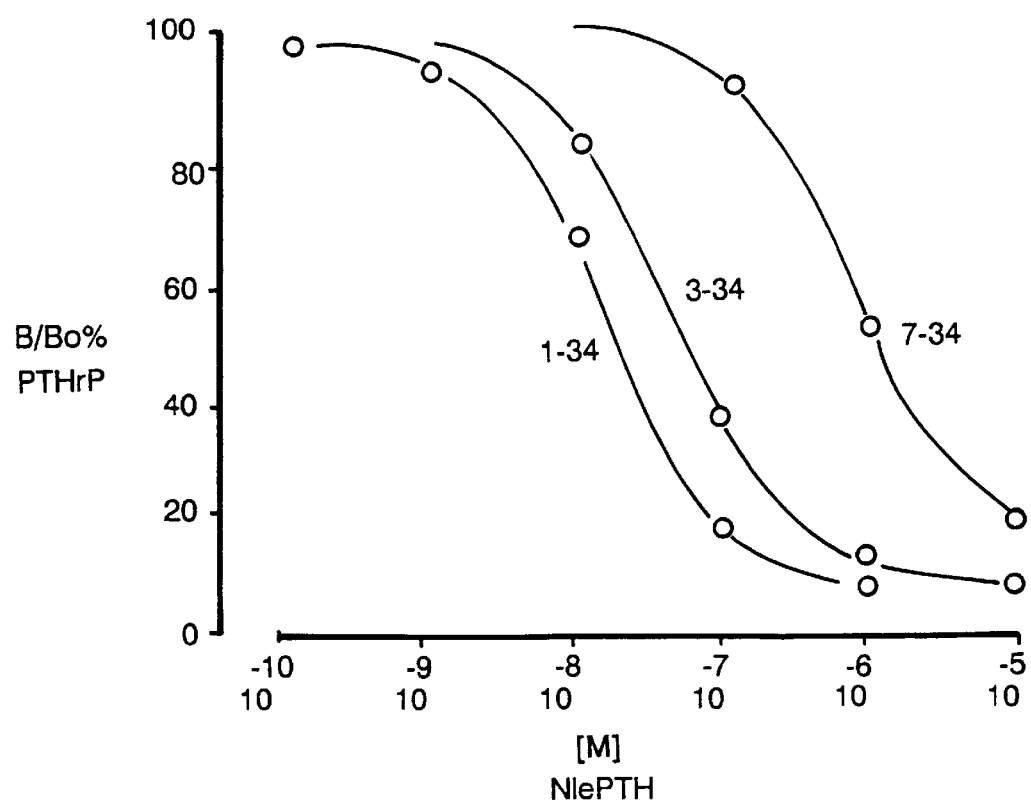

FIG. 9 is a graph illustrating binding of PTHrP to COS cells transfected with OK-H.

Figure 10:
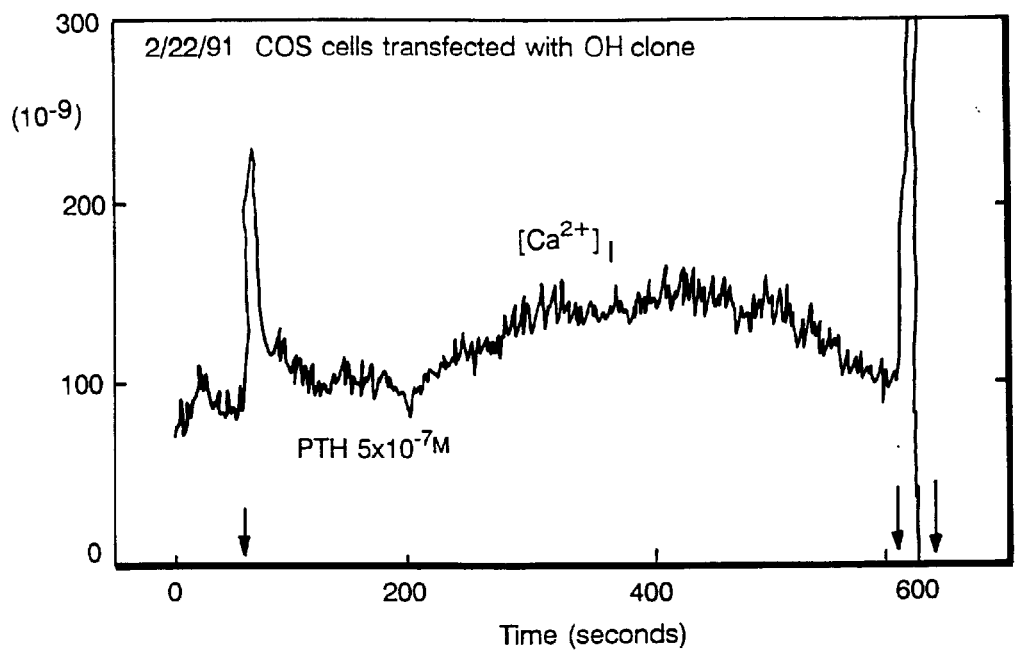

FIG. 10 is a graph illustrating stimulation of intracellular free calcium by NlePTH in COS cells transfected with OK-H.

Figure 11:
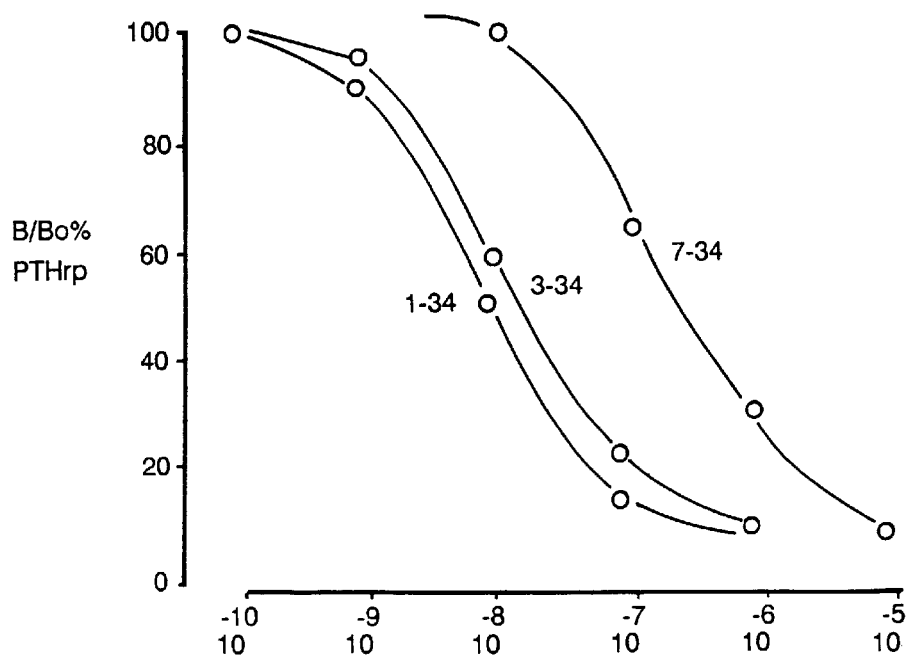

FIG. 11 is a graph illustrating binding of PTHrP to COS cells transfected with OK-O.

Figure 12:
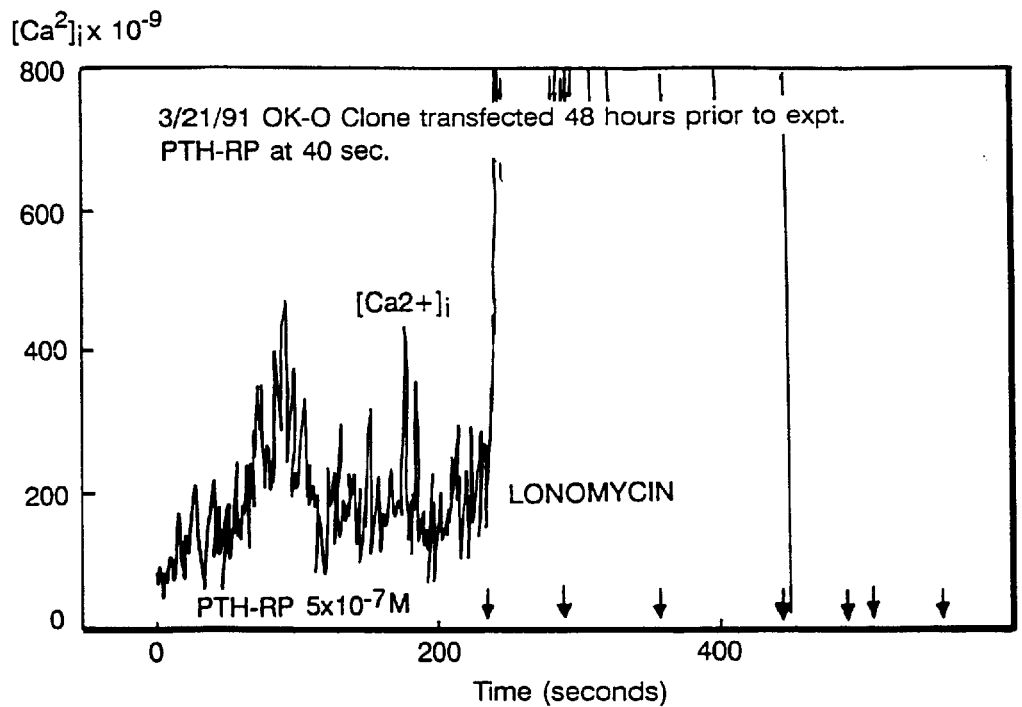

FIG. 12 is a graph illustrating stimulation of intracellular free calcium by NlePTH in COS cells transfected with OK-O.

Figure 13:
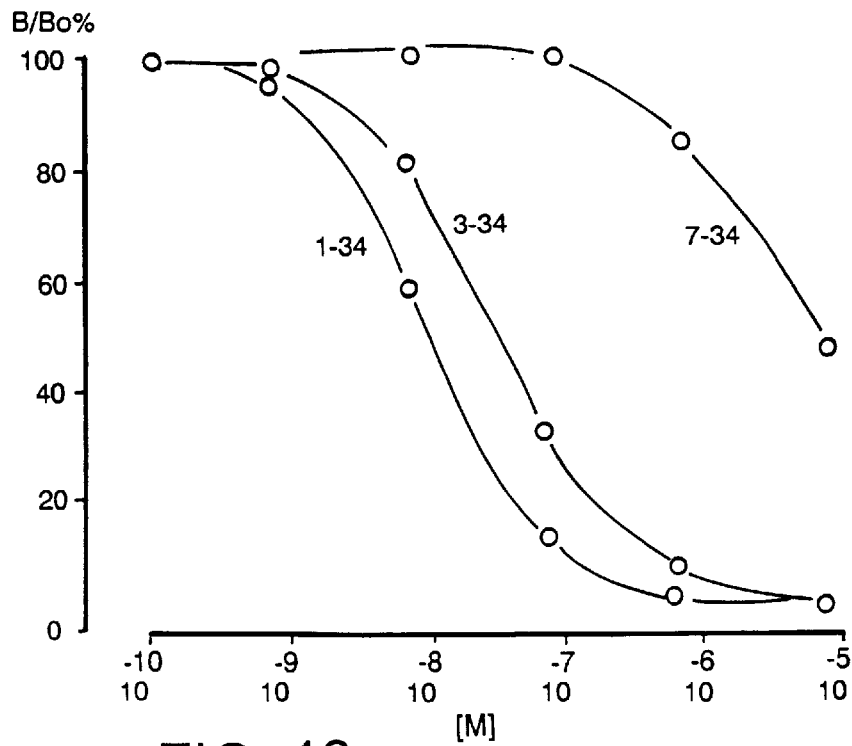

FIG. 13 is a graph illustrating binding of PTHrP to COS cells transfected with R15B.

Figure 14:
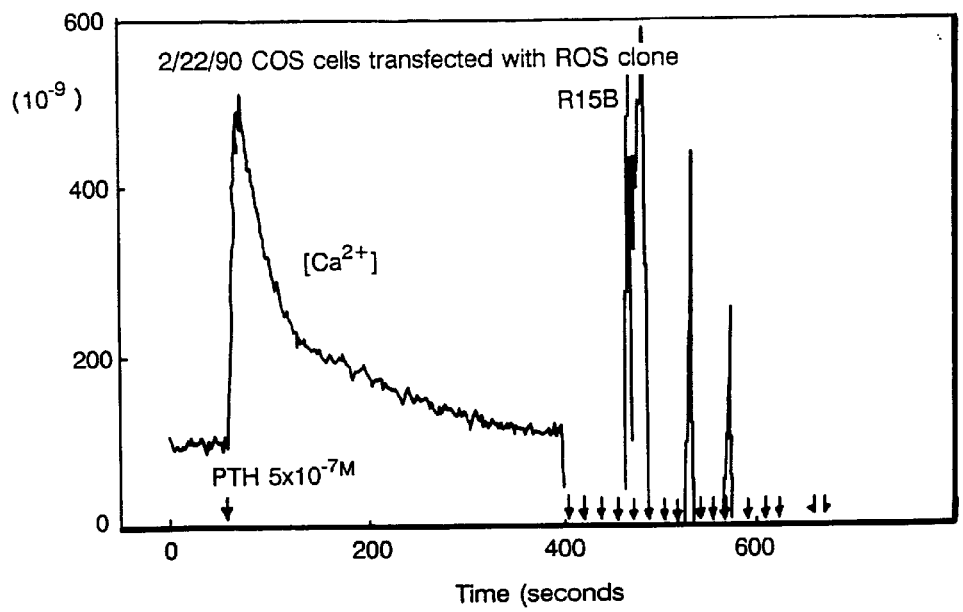

FIG. 14 is a graph illustrating stimulation of intracellular free calcium by NlePTH in COS cells transfected with R15B.

Figure 15A:
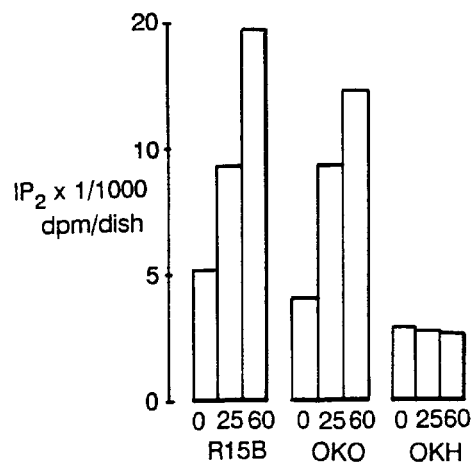

FIG. 15A is a graph illustrating accumulation of inositol bisphosphate metabolism ($IP_2$) after NlePTH stimulation of COS cells transfected with OK-H, OK-O, or R15B.

Figure 15B:
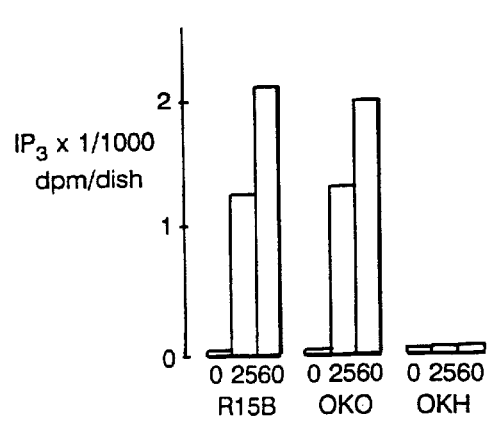

FIG. 15B is a graph illustrating accumulation of inositol triphosphate ($IP_3$) after NlePTH stimulation of COS cells transfected with OK-H, OK-O, or R15B.

Figure 16:
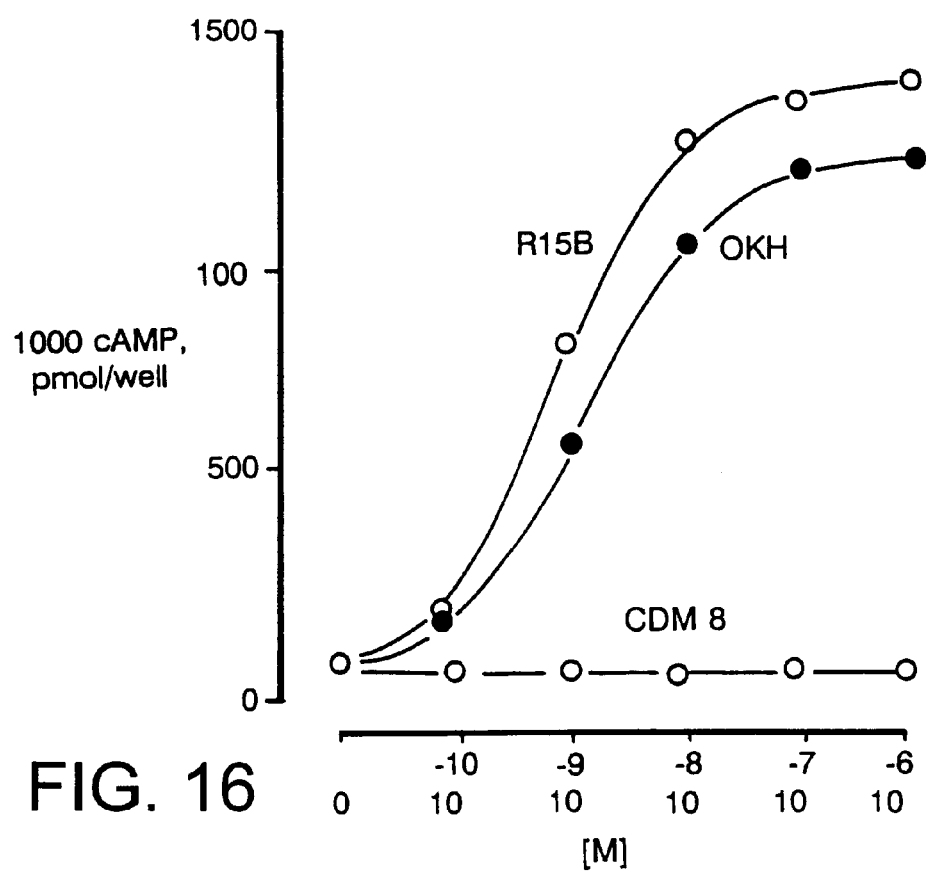

FIG. 16 is a graph illustrating cyclic AMP accumulation in COS cells transfected with CDM-8, OK-H, R15B by NlePTH.

Figure 17A:
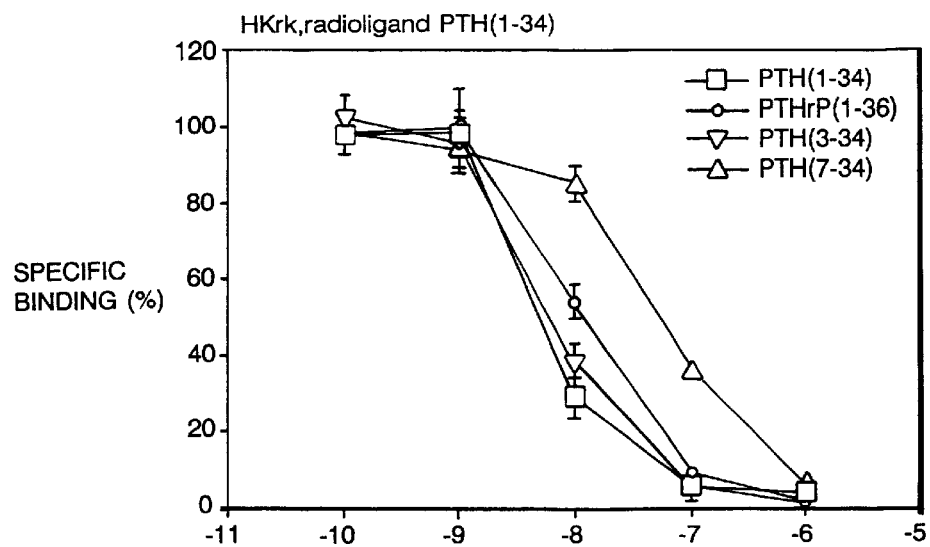

FIG. 17A is a graphs illustrating binding of $^{125}$I-labelled PTH(1–34) to COS-7 cells transiently expressing the human kidney PTH/PTHrP receptor; competing ligands included PTH( 1–34) (—□—), PTHrP(1–36) (—O—), PTH(3–34) (—▽—), and PTH(7–34) (—△—). Data are given as % specific binding and represent the mean± SD of at least three independent experiments.

Figure 17B:
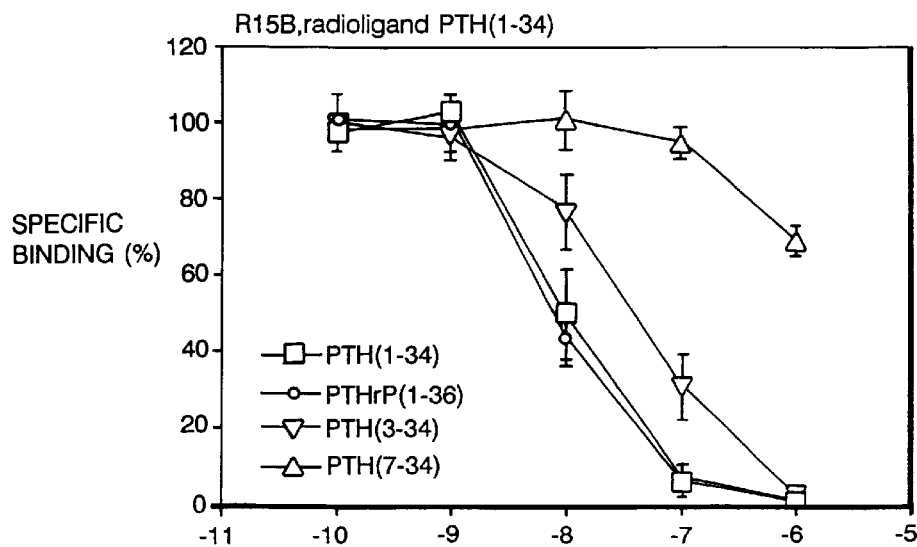

FIG. 17B is graph illustrating binding of $^{125}$I-labelled PTH(1–34) to COS7 cells transiently expressing the rat bone PTH/PTHrP receptor, competing ligands included PTH (1–34) (—□—), PTHrP(1–36) (-O-), PTH(3–34) (—▽—), and PTH(7–34) (—△—). Data are given as % specific binding adn represent the mean ± SD of at least three independent experiments.

Figure 17C:
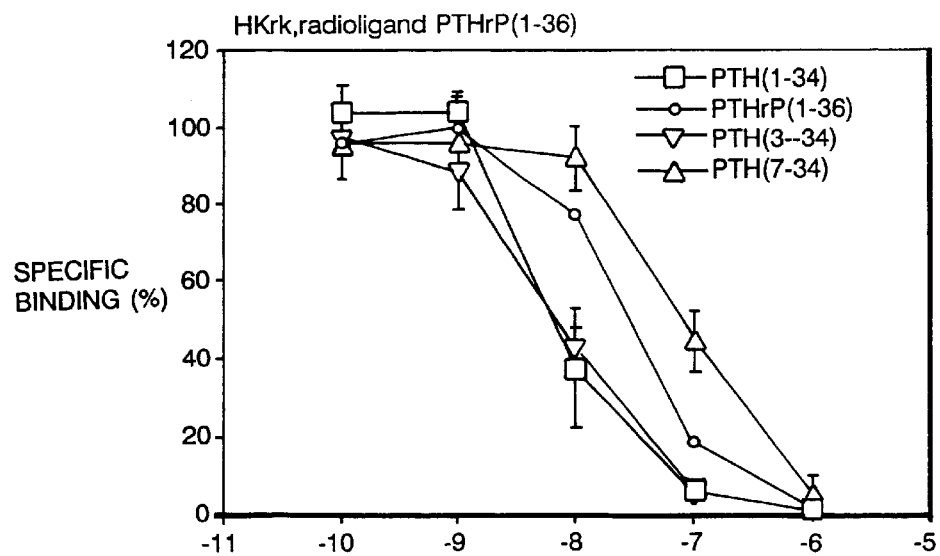

FIG. 17C is a graph illustrating binding of $^{125}$I-labelled PTHrP(1–36) to COS-7 cells transiently expressing with the human kidney PTH/PTHrP receptor; competing ligands included PTH(1–34) (—□—), PTHrP(1–36) (—O—), PTH (3–34) (—▽—), and PTH(7–34) (—△—). Data are given as % specific binding and represent the mean ± SD of at least three independent experiments.

Figure 17D:
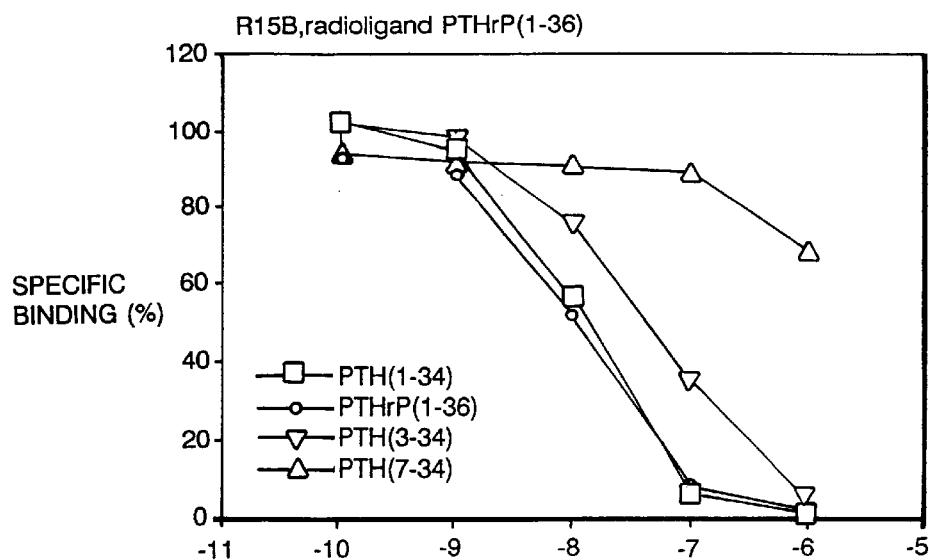

FIG. 17D is a graph illustrating binding of $^{125}$I-labelled PTHrP(1–36) to COS7 cells transiently expressing the rat bone PTH/PTHrP receptor competing ligands included PTH (1–34) (—□—), PTHrP(1–36) (—O—), PTH(3–34) (—▽—), and PTH(7–34) (—△—). Data are given as % specific binding and represent the mean ± SD of at least three independent experiments.

Figure 18:
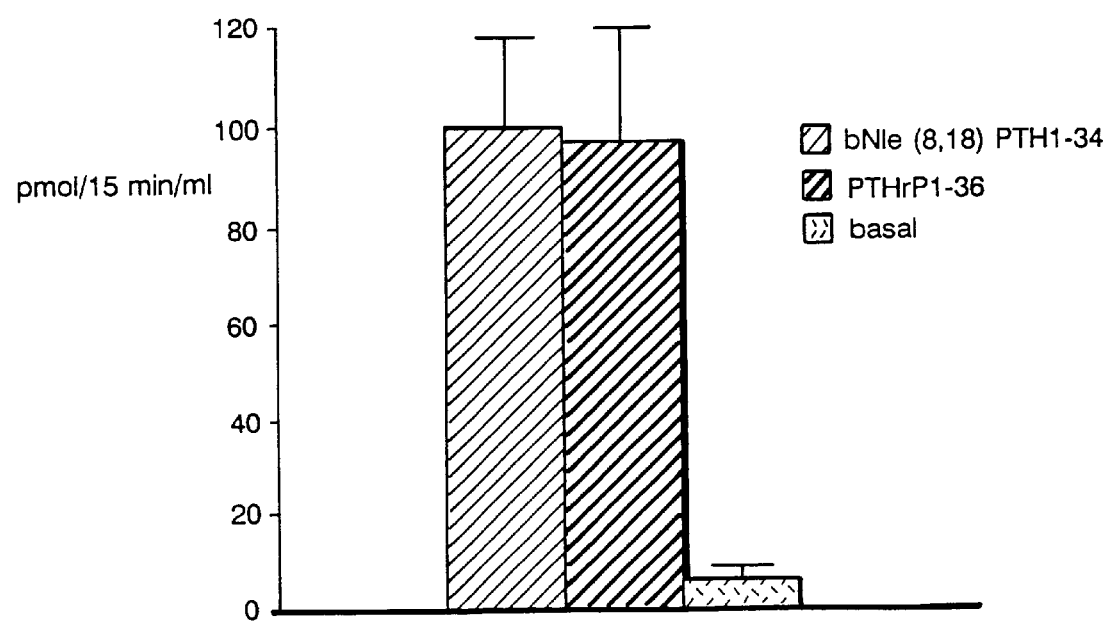

FIG. 18 is a bar graph illustrating stimulated accumulation of intracellular cAMP in COS-7 cells transiently expressing the human kidney receptor. Data show the mean±SD, and are representative of at least three independent experiments.

Figure 19:
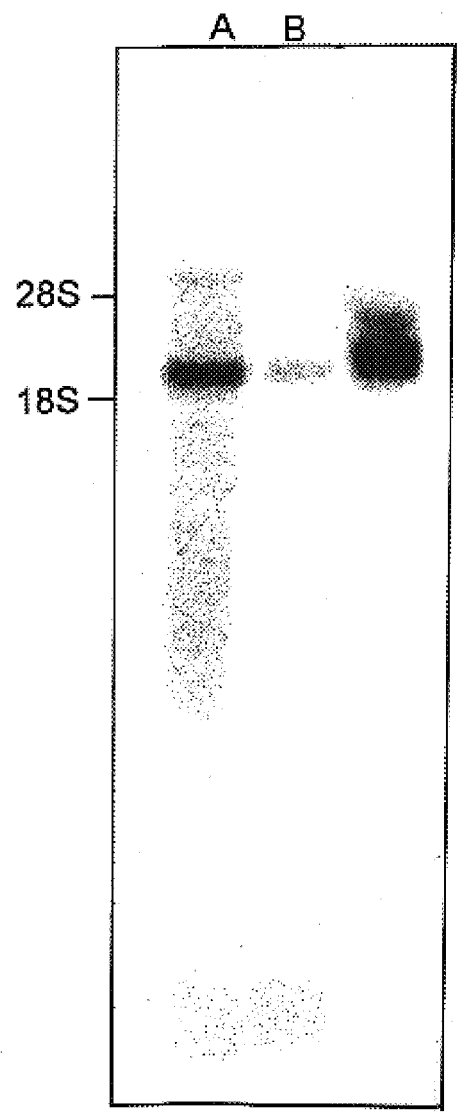

FIG. 19 represents a Northern blot analysis of total RNA (~10 μg/lane) prepared from human kidney (A) and SaOS-2 cells (B). The blot was hybridized with the full length cDNA encoding the human kidney PTH/PTHrP receptor; positions of 28S and 18S ribosomal RNA bands are indicated.

Figure 20:
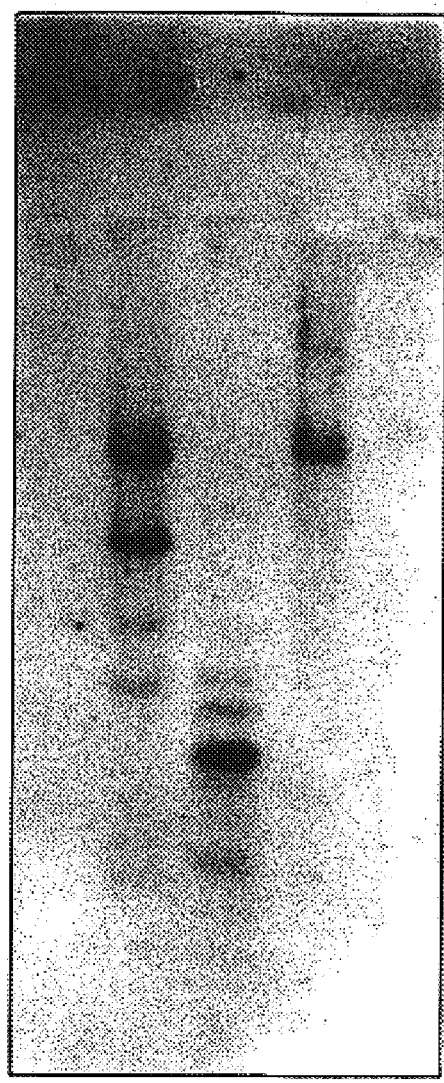

FIG. 20 represents a Southern blot analysis of human genomic DNA digested with SstI, HindIII, and XhoI (~10 μg/lane. The blot was hybridized with the full length cDNA encoding the human kidney PTH/PTHrP receptor.

Figure 21:
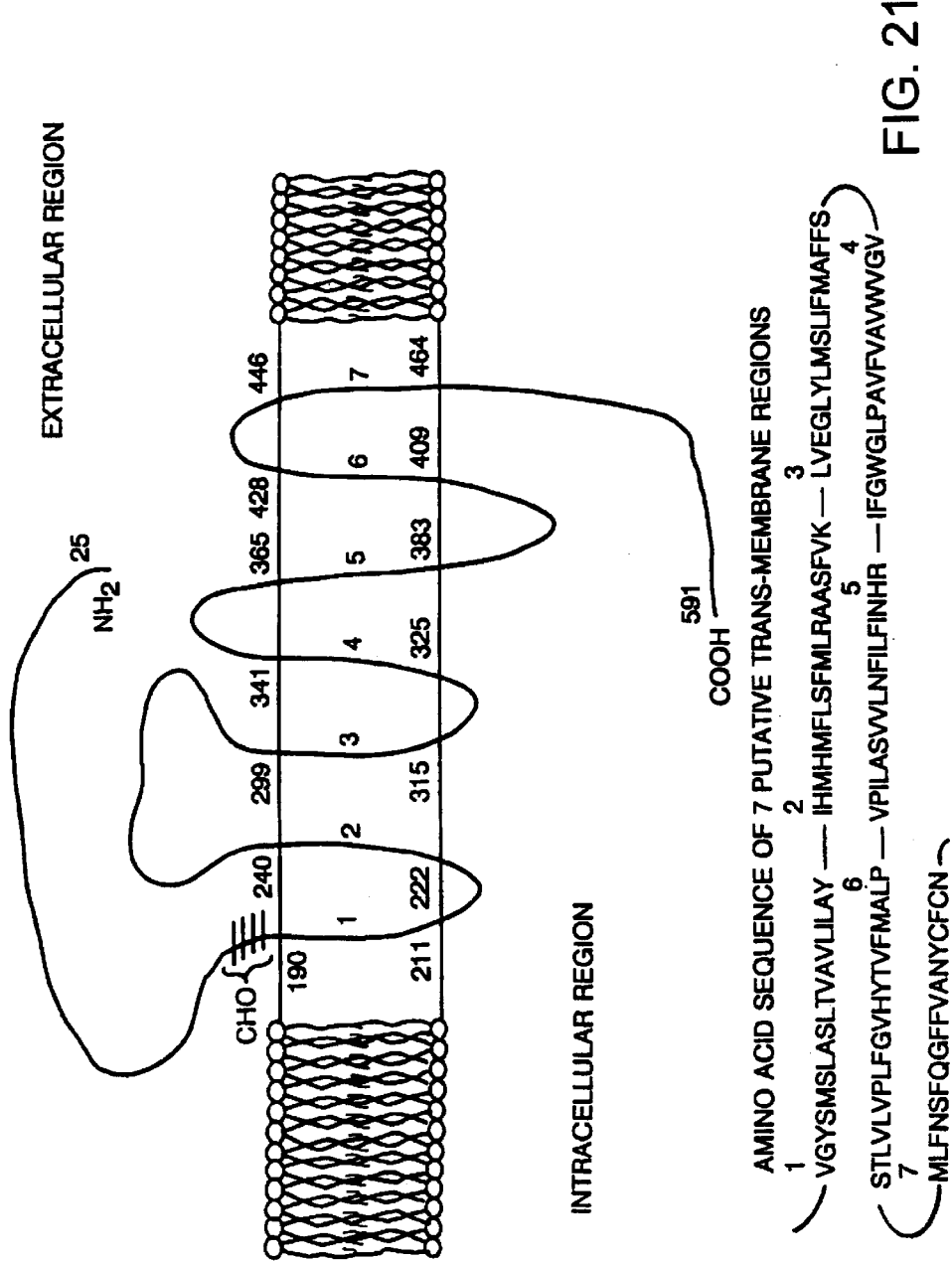

FIG. 21 is a schematic diagram of the proposed arrangement, in a cellular membrane, of PTH/PTHrP rat bone receptor encoded by R15B. The amino acid sequences of the seven transmembrane regions are provided, from N-terminal to C-terminal, as SEQ ID NOs:22–28, respectively.

MATERIALS AND METHODS

GENERAL: [$Nle^{8,18}$, $Tyr^{34}$]bPTH(1–34)amide (PTH (1–34)), [$Nle^{8,18}$, $Tyr^{34}$]bPTH(3–34)amide (PTH(3–34)), and [$Nle^{8,18}$, $Tyr^{34}$]bPTH(7–34)amide (PTH(7–34)) were obtained from Bachem Fine Chemicals, Torrance, Calif.; [Tyr 36]PTHrP(1–36)amide (PTHrP(1–36)) was synthesized as described (Keutman et al., Endocrinology 117:1230, 1985) using an Applied Biosystems Synthesizer 420A. Dulbecco's modified Eagles medium (DMEM), EDTA/trypsin, and gentamycin were from GIBCO (Grand Island, N.Y.); fetal bovine serum (FBS) was from Hiclone Laboratory, Logan, Utah. Total RNA from human kidney was provided by Per Hellman, University Hospital, Uppsala, Sweden.

Oligonucleotide primers were synthesized using an Applied Biosystems 380B DNA Synthesizer. Restriction enzymes, Klenow enzyme, T4 polynucleotide Kinase and T4 DNA ligase were from New England Biolabs, Beverly, Mass. Calf alkaline phosphatase was from Boehringer Mannheim, Germany. All other reagents were of highest purity available.

Cells

Cell lines used include COS cells, OK cells, SaOS-2 cells, CHO cells, AtT20 cells, LLC-PK1 cells, and UMR-106 cells, which are available from a variety of sources including the American Type Culture Collection (Rockland, Md.), Accession Nos. CRL1650, CRL6551, HTB85, CCL61, CCL89, CL101, and CRL1161, respectively. ROS 17/2 and ROS 17/2.8 are available from a number of sources including Dr. Gideon Rodan (Merck Laboratories, West Point, Pa.). MC-3T3 cells are derived from mouse bone cells and are also available from a number of sources including Dr. Chohei Shigeno (Dept. of Biochem. Medicine, Hyoto Univ., Kyoto, Japan).

All cells were grown in a humidified 95% air, 5% $CO_2$ atmosphere and maintained in monolayer culture with Ham's F-12 or DMEM medium (Grand Island Biological Co.), supplemented with 5% or 10% fetal calf serum (M.A. Bioproducts, Walkersville, Md.). The medium was changed every 3 or 4 days, and the cells were subcultured every 2 or 3 weeks by trypsinization using standard methods.

Cloning

Isolation of cDNA clones encoding the rat and opossum PTH/PTHrP receptors: Total RNA was initially isolated from rat osteosarcoma (ROS) cells (ROS 17/2.8) and opossum kidney (OK) cells, by standard methods using guanidium isothiocyanate (Ullrich et al., Science 196: 1313, 1977; Chirgwin et al. Biochemistry 24: 5294, 1979), and centrifugation through cesium chloride (Gilsen et al., Biochemistry 13: 2633, 1974). Poly A+ RNAs (mRNAs) were then recovered after passage of the total RNAs over oligo dT columns (Pharmacia, Piscataway, N.J.) by the method of Aviv and Leder (Proc. Natl. Acad Sci. USA 69: 14087, 1972). The cDNA library from the ROS 17/2.3 mRNA was prepared from poly A+ RNA using the method of Gubler and Hoffman (Gene (Amst.) 25: 263, 1983). Oligo dT-primed and random-primed cDNAs were synthesized from poly A+ ROS 17/2.8 and OK cell mRNA, respectively (Aviv and Leder, supra). The cDNAs were ligated to BstX1 linkers (Invitrogen, San Diego, Calif.) and size-selected by centrifugation (3 h, 55,000×g) in a 5–20% potassium acetate gradient. The size-selected cDNA was then inserted into the plasmid vector, pcDNA I (Invitrogen), using the non-self annealing BstX1 restriction sites. The resultant plasmid libraries were then used to transform E. coli (MC1061/P3, Invitrogen) containing a larger helper plasmid, p3. The p3 plasmid possesses amber mutations in two genes which code for ampicillin and tetracycline resistance. Using ampicillin and tetracycline selection, only those cells containing both the p3 and a tRNA suppressor gene, which is contained within pcDNA I, were capable of growth. The transformed bacteria were then grown to confluence, and the plasmid DNAs isolated using standard techniques (e.g., see Ausebel et al., Current Protocols in Molecular Biology, John Wiley Sons, New York, 1989). These DNAs were then taken up in a DEAE-dextran solution, and used to transfect African Green Monkey kidney (COS) cells, which had been grown to 75% confluence in "sideflasks" (Nunc, Denmark).

Screening for COS cells containing plasmids capable of expressing functionally-intact ROS or OK cell parathyroid hormone/parathyroid hormone related-protein (PTH/PTHrP) receptor proteins was performed according to Gearing et al. (EMBO J. 8: 3676, 1989), with some minor modifications including DEAE-Dextran transfection in sideflasks. Forty-eight hours after transfection, the cells were tested for binding of $^{125}$I-labeled [Tyr$^{36}$]PTHrp (1–36) amide, using methods previously described (Yamamoto et al., Endocrinology 122: 1208, 1988), with the following exceptions: the time and temperature of the incubation were 2 h and room temperature, respectively. After rinsing, the cells were fixed with 1.25% glutaraldehyde, and rinsed with 1% gelatin. After snapping off the top of the sideflask, the remaining microscope slide was dipped into NTB-2 photographic emulsion (Eastman Kodak, Rochester, N.Y.). After 3–4 days of exposure at 4° C., the slides were developed, fixed, and stained with 0.03% toluene blue. Screening of each slide was performed under a light microscope (Olympus). One pool of plasmid-DNA from ROS cells, and two pools of plasmid-DNA from OK cells, (10,000 independent clones), each gave rise to 3–4 transfected COS cells expressing the PTH/PTHrP receptor. These pools were subsequently subdivided. The subpools were used to transfect COS cells, and single clones were identified that expressed receptor protein capable of binding the radioligand.

Isolation of cDNA and genomic DNA clones encoding the human PTH/PTHrP receptor: A human kidney oligo dT-primed cDNA library (1.7×10$^6$ independent clones) in lambda GT10 and a genomic library of human placental DNA (2.5×10$^6$ independent clones) in EMBL3 (Sp6/T7) (Clontech, Palo Alto, Calif.) were screened by the plaque hybridization technique (Sambrook et al., Molecular Cloning: A Laboratory Manual, 2nd Ed. pp. 108–113, Cold Spring Harbor Laboratory, Cold Spring Harbor, N.Y., 1989) with the $^{32}$P-labelled (random primed labelling kit Boehringer Mannheim, Germany) BamHI/NotI 1.8 kb restriction enzyme fragment encoding most of the coding sequence or the rat bone PTH/PTHrp receptor (FIGS. 3A–E). The nitrocellulose filters were incubated at 42° C. for 4 hrs in a prehybridization solution containing 50% formamide, 4×saline sodium citrate (SSC; $^1$×SSC: 300 mM NaCl, 30 mM NaCitrate, pH 7.0), 2× Denhardt's solution, 10% Dextran sulphate, 100 μg/ml salmon sperm DNA (final concentration). The hybridizations were carried out in the same solution at 42° C. for 18–24 h. Filters were washed with 2×SSC/0.1% SDS for 30 minutes at room temperature and then with $^1$×SSC/0.1% SDS for 30 minutes at 45° C. The films were exposed at −80° C. for 18–24 h using intensifying screens.

About 1,000,000 clones were screened from each library. Positive clones were plaque-purified and lambda phage DNA was isolated (Sambrook et al., supra). Cloned inserts were removed from phage DNA by digestion with restriction endonucleases HindIII and EcoRI (lambda GT10 library), or with XhoI and SstI (EMBL3 library), and were then subcloned into pcDNAI (Invitrogen, San Diego, Calif.) using the appropriate, dephosphorylated restriction sites. Sequencing of the CsCl$_2$-purified subclones was performed according to Sanger et al. (Biochem 74:5463, 1977) by the dideoxy termination method (Sequenase version 2 sequencing kit, United States Biochemical Corporation, Cleveland, Ohio).

Reverse transcription and polymerase chain reaction (PCR): 3 μg of poly (A)+ RNA from human kidney (Clontech, Palo Alto, Calif.) in 73.5 μl of H$_2$O was incubated at 100° C. for 30 seconds, quenched on ice, and then added to 20 μl of 5×RT buffer (1×RT buffer: 40 mM Tris-HCl, pH 8.2, 40 mM KCl, 6.6 mM MgCl$_2$, 10 mM dithiothreitol, and dNTPs at 0.5 mM each), 2 μl (4 units) RNasin (Promega Biotec, Madison, Wis.), 1 μl (80 pmo/μl) of the human cDNA primer H12 (5'-AGATGAGGCTGTGCAGGT-3'; SEQ ID NO.: 14) and 80 units of avian myeloblastosis virus reverse transcriptase (Life Sciences, St. Petersburg, Fla.). The reaction mixture was incubated for 40 minutes at 42° C. One-tenth of the first strand synthesis reaction mixture was then amplified by PCR in a final volume of 100 μl containing 3 mM MgSO$_4$, 200 μM dNTPs, 2 units of Vent polymerase (New England Biolab, Beverly, Mass.), and 2 μM each of the forward and the reverse primers (PCR conditions: denaturing for 1 min at 94° C., annealing for 1 min at 50° C., and extension at 72° C. for 3 minutes; 40 cycles).

Two independent PCRs were performed using two different forward primers: i) degenerate primer RK-1

```
(5'-GGAATTCCATGGGAGCGGCCCGGAT-3';  SEQ ID NO.: 15)
            G      CC
``` based on the 5' coding end of the two previously cloned PTH/PTHrP receptors (described above), and ii) primer RK-2 (5'-CGGGATCCCGCGGCCCTAGGCGGT-3'; SEQ ID NO.: 16) based on the 5' untranslated region of the human genomic clone HPG1. Both PCR reactions used the reverse primer H26 (5'AGTATAGCGTCCTTGACGA-3'; SEQ ID NO.: 17) representing nucleotides 713 to 731 of the coding region of the human PTH/PTHrP receptor (FIG. 4). PCR products were blunt-ended using Klenow enzyme and cloned into dephosphorylated pcDNAI cut with EcoRV.

Northern blot analysis: Total RNA was extracted from SaOS-2 cells and from human kidney by the guanidine thiocyanate method (Chirgwin et al., Biochem. 18:5294, 1979). For Northern blot analysis, ~10 μg of total RNA was subjected to electrophoresis on a 1.5%/37% formaldehyde gel and blotted onto nitrocellulose filters (Schleicher and Schuell, Keene, N.H.). The hybridization conditions were the same as those for screening the phage libraries (see above). The filters were washed at a final stringency of 0.5×SSC/0.1% SDS for 30 min at 60° C. and exposed for autoradiography.

Southern blot analysis: Human genomic DNA was prepared using the SDS/proteinase K method (Gross-Bellard et al., Eur. J. Biochem. 36:32, 1973). For Southern analysis, ~10 μg of DNA was digested with SstI, PvuII and XhoI; subjected to electrophoresis on a 0.8% agarose gel; and blotted onto nitrocellulose membranes (Schleicher and Schuell, Keene, N.H.). The hybridization conditions were the same as those for screening the phage libraries (see above). The filters were washed at a final stringency of 0.5×SSC/0.1% SDS for 30. min at 55° C. and exposed for autoradiography.

Functional Assays

Tests to characterize the functional properties of the cloned receptors expressed on COS cells included:

I) binding of PTH and PTHrP fragments and analogues,

II) stimulation of cyclic AMP accumulation by PTH and PTHrP fragments and analogues, III) increase of intracellular free calcium by PTH and PTHrP fragments and analogues, and IV) activation of inositol phosphate metabolism by PTH and PTHrP fragments and analogues. The methodologies are as follows:

Radioreceptor Assay

[$Nle^8,Nle^{18},Tyr^{34}$]bPTH-(1–34)amide (NlePTH), and [$Tyr^{36}$]PTHrP(1–36)amide(PTHrP) were iodinated with $Na^{125}I$ (carrier free, New England Nuclear, Boston, Mass.) as previously reported (Segre et al., J. Biol. Chem. 254: 6980, 1979), and purified by reverse-phase HPLC. In brief, the labeled peptide was dissolved in 0.1% trifluoracetic acid (TFA), applied to a $C_{18}$ Sep-pak cartridge (Waters Associates, Inc., Milford, Mass.) and eluted with a solution of 60% acetonitrile in 0.1% TFA. After lyophilization, the radioligand then was applied to $C_{18}$-µBondapak column (3.9 mm×30 cm. Waters Associates) and eluted over 30 min with a linear gradient of 30–50% acetonitrile-0.1% TFA at a flow rate of 2 ml/min. The radioligand eluted in two peaks; the first peak, which eluted at approximately 38% acetonitrile, was used in these studies because it gave higher total and specific bindings. The specific activity was 500±75 mCi/mg, which corresponds to an average iodine-peptide ratio of 1.

COS-7 cells were grown in 15 cm plates in DMEM, 10% heat-inactivated PBS, 10 mg/L gentamycin until 80–90% confluent. Twenty-four hours after transfection by the DEAE/Dextran method (Sambrook et al., supra), with 1–2 µg of plasmid DNA, the cells were trypsinized and replated in multiwell plastic dishes (16 or 35 mm diameter, Costar, Cambridge, Mass.) at a cell concentration of $5×10^4$ cells/$cm^2$). Cell number increased only slightly after transfection. After continuing culture for another 48 h, radiorecepter assays were performed. The culture medium was replaced with buffer containing 50 mM Tris-HCL (pH 7.7), 100 mM NaCl, 2 mM $CaCl_2$, 5 mM KCL, 0.5% heat-inactivated fetal bovine serum (GIBCO), and 5% heat-inactivated horse serum (KC Biological Inc., Lenexa, Kans.) immediately before studies were initiated. Unless otherwise indicated, studies were conducted with cells incubated in this buffer at 15° C. for 4 h with $4×10^5$ cpm/ml ($9.6×10^{-11}$ M) of $^{125}I$-labeled NlePTH or PTHrP.

Incubations were terminated by aspirating the buffer, and repeatedly (×3) washing the culture dishes, containing the adherent cells with chilled 0.9% NaCl solution, over a 15 sec period. Cell-bound radioactivity was recovered by the sequential addition (×3) of 1 N NaOH (200 µl) to each well. After 30 min at room temperature, the NaOH was transferred to a glass tube. A second and third extraction with 1 N NaOH (200 µl) were combined with the first, and the total radioactivity was counted in a γ-spectrometer (Packard Instruments, Downers Grove, Ill.). Tracer adherence to culture vessel without cells was negligible (<0.2% of total counts added), if vessels were preincubated with culture medium.

Determinations of cAMP Accumulation

Intracellular cAMP accumulation was measured as described previously (Abou-Samra et al., J. Biol. Chem. 262:1129, 1986). Cells in 24-well plates were rinsed with culture medium containing 0.1% BSA and 2 mM IBMX. The cells were then incubated with PTH or PTHrP for 15 min. at 37° C. The supernatant was removed and the cells immediately frozen by placing the whole plate in dry ice powder. Intracellular cAMP was extracted by thawing the cells in 1 ml of 50 mM HCl and analyzed by a specific radioimmunoassay using an anti-cAMP antibody (e.g., Sigma, St. Louis, Mo.). A cAMP analog (2'-O-monosuccinyl-adenosine 3':5'-cyclic monophosphate tyrosyl methyl ester, obtained from Sigma) which was used a tracer for cAMP was iodinated by the chloramine T method. Free iodine was removed by adsorbing the iodinated cAMP analog onto a C18 Sep-pak cartridge (Waters, Milford, Mass.). After washing with $dH_2O$, the iodinated cAMP analog was eluted from the Sep-pak Cartridge with 40% acetonitrille (ACN) and 0.1% trifluoroacetic acid (TFA). The iodinated cAMP analog was lyophilized, reconstituted in 1 ml 0.1% TFA, and injected into a C18 reverse phase HPLC column (Waters). The column was equilibrated with 10% ACN in 0.1% TFA, and eluted with gradient of 10–30% ACN in 0.1% TFA. This allows separation of the mono-iodinated cAMP analog from the non-iodinated cAMP analog. The tracer is stable for up to 4 months when stored at −20° C. The standard used for the assay, adenosine 3':5'-cyclic monophosphate, was purchased from Sigma. Samples (1–10 µl of HCl extracts) or standards (0.04–100 fmol/tube) were diluted in 50 mM Na-acetate (pH 5.5), and acetylated with 10 µl of mixture of triethylamine and acetic anhydride (2:1 vol:vol). After acetylation, cAMP antiserum (100 µl) was added from a stock solution (1:4000) made in PBS (pH 7.4), 5 mM EDTA and 1% normal rabbit serum. The tracer was diluted in PBS (pH 7.4) with 0.1% BSA, and added (20,000 cpm/tube). The assay was incubated at 4° C. overnight. The bound tracer was precipitated by adding 100 µl of goat anti-rabbit antiserum (1:20 in PBS) and 1 ml of 7% polyethyleneglycol (MW 5000–6000), centrifuging at 2000 rpm for 30 min. at 4° C. The supernatant was removed and the bound radioactivity was counted in a γ-counter (Micromedic). Standard curves were calculated using the four-parameter RIA program supplied by Micromedic. Typically, the assay sensitivity is 0.1 fmol/tube, and the standard concentration that displaces 50% of tracer is 5 fmol/tube.

In an alternative method for assaying cAMP accumulation, COS cells transfected with PTH/PTHrP receptor cDNA are harvested with a plastic policeman into a solution containing 10 mM Tris-HCl (pH 7.5), 0.2 mM MgCl, 0.5 mM ethyleneglycolbis (β-amino ethyl ether) N,N'-tetra-acetic acid (EGTA) (Sigma) and 1 mM dithiothreitol (Sigma). Cells are homogenated by 20 strokes or tightly-fitting Dounce homogenizer, and centrifuged at 13,000×g for 15 min at 4° C. (Eppendorf, type 5412, Brinkmann Instruments, Inc., Westburg, N.Y.). The pellet containing the plasma membranes is resuspended in the same buffer by several strokes with a Dounce homogenizer, and further diluted with the same buffer to a protein concentration of approximately 1.2 mg/ml, as determined by the method of Lowry et al. (Lowry et al., J. Biol. Chem 193: 265, 1951). Approximately 30 µg (25 µl) membrane are incubated with varying concentrations of hormone or vehicle alone for 10 min at 37° C. (final volume, 100 µl) in 50 mM Tris-HCl (pH 7.5), 0.8 mM ATP, $4×10^6$ cpm [$α-^{32}P$] ATP (New England Nuclear, Boston, Mass.), 9 mM theophylline, 4.2 mM $MgCl_2$, 26 mM KCl, 0.12% BSA, and an ATP-regenerating system containing 5 mM creatine phosphate (Schwartz/Mann Division, Becton-Dickenson & Co., Orangeburg, N.Y.) and 0.1 mg/ml creatine phosphokinase (Shwartz/Mann). Incubations are initiated by addition of the membrane suspension and terminated by addition of 100 μl of a solution containing 20 mM cAMP, approximately 50,000 cpm [$^3$H]cAMP, and 80 mM ATP. The reaction mixture is boiled, and the [$^{32}$P]cAMP generated is purified by sequential chromatography on ion-exchange columns (Dowex 50 W-X4, Biorad Lab, Richmond, Calif.) and alumina (Sigma). The [$^{32}$P]cAMP may be counted in a β-scintillation counter (Packard Instrument Co.), with correction for recovery of [$^3$H]cAMP.

Determination of Intracellular Free Calcium

Measurements of intracellular calcium levels in cells transfected with PTH/PTHrP receptor cDNAs were performed using Fura-2 AM (acetomethoxy ester of Fura-2, Molecular Probes Inc., Eugene, Oreg.) loaded cells. Details of the methodology are:

Coverslips plated with COS cells were incubated in Fura-2 AM loading buffer containing, in mM: HEPES (N-[2-Hydroxyethyl]piperazine-N'-[2-ethanesulfonic acid]), 20; $CaCl_2$, 1; KCl 5; NaCl, 145; $MgSO_4$, 0.5; $NaHCO_3$, 25; $K_2HPO_4$, 1.4; glucose, 10; and Fura-2 AM 91-(2-5'-carboxyoxazol-2'-yl)-6-aminobenzofuran-5oxy-(2'-amino-5'-methylphenoxy)ethane-N,N,N',N'-tetraaecetic acid acetomethoxy ester), 0.5; at 37° C. at pH7.4, aerated with 95% air and 5% $CO_2$ for 45 minutes. Cells loaded with Fura-2 AM were then washed with a modified Krebs-Heinseleit (KH) buffer containing, in mM: HEPES, 20; $CaCl_2$, 1; KCl, 5; NaCl, 145; $MgSO_4$, 0.5; $Na_2HPO_4$, 1; glucose, 5; pH7.4. To check that cleavage of the ester occurred, the excitation spectra after different times of Fura-2 AM incubation were measured. At 5 min. after the start of incubation, the excitation spectrum peaked at approximately 360 nm, reflecting incomplete hydrolysis of Fura-2 AM, whereas beyond 30 min. the excitation spectrum peaked at 345 nM, characteristic of Fura-2.

To measure fluorescence of individual cells, the cover slips were placed in a microscope tissue chamber (Biophysica Technologies, Inc., MD). The chamber consisted of a shallow, sloped compartment made of Teflon with a silicone rubber seal. The cover slips served as the bottom of the chamber. A heater/cooler ring was encased in the silicone rubber which sealed the coverslip in place. Temperatures were varied between 22° C. and 37° C. by applying 0–7.4 V to the heater. If the temperature is not specifically stated, the experiment was performed at 37° C. The chamber was mounted on the stage of an inverted microscope (Zeiss IM-35, Thornwood, N.Y.). Fura-2 fluorescence was excited with a 75 watt Xenon arc lamp placed at the focal point of a condenser (Photon Technologies International (PTI) Inc., NJ). Grating monochromators, alternated by a rotating chopper in which mirror vanes alternate with transmitting sectors, were used for selecting wavelengths. The monochromator outputs were combined to form a common optical path which exited the source housing through an adjustable iris. The light then passed through quartz lenses and a dichroic mirror through a 100× Nikon Fluor objective. A photon-counting PMT device detection was used to measure the light output. Data analysis was performed using PTI software run on an IBM-compatible AT/286 computer using the MS-DOS operating system. Data was retained and manipulated in a packed binary format.

Intracellular calcium concentrations were calculated according to the formula: $[Ca^{2+}]i=Kd(R-Rmin)/(Rmax-R)$ B, where R is the ratio of fluorescence of the cell at 340 and 380 nm; Rmax and Rmin represent the ratios of Fura-2 fluorescence intensity at 340 and 380 nm excitation wavelengths in the presence of a saturating amount of calcium and effectively zero calcium, respectively; B is the ratio of fluorescence of Fura-2 at 380 nm in zero calcium to that in saturating amounts of calcium; and $K_d$ is the dissociation constant of Fura-2 for calcium. To determine Rmax, at the end of an experiment ionomycin was added to the Fura-2 AM loaded cells to equilibrate $Ca^{2+}$ between the extracellular (1 mM) and intracellular environments. To calculate Rmin, 1 mM EGTA was then added to the bathing solution. Different dissociation constants were used at the different temperatures: 224 nM at 34–37° C. and 135 nM at 24–27° C.

Determination of Inositol Phosphate

The level of inositol phosphate metabolism was determined in COS cells transfected with PTH/PTHrP receptors using previously published methods (Bonventre, et al., J. Biol. Chem. 265: 4934, 1990).

Results

Molecular Characterization

Two independent clones (OK-H and OK-O), both of which were isolated from the OK cell cDNA library, had lengths of approximately 2 kilobases. The determined nucleotide sequence and predicted amino acid sequence of these clones are shown in FIGS. 1A–E (SEQ ID NO.:1) and FIGS. 2A–E (SEQ ID NO.:2) respectively. The R15B clone isolated from the ROS cell cDNA library had a length of approximately 4 kilobases. The determined nucleotide sequence and predicted amino acid sequence of the rat bone PTH/PTHrP receptor is depicted in FIGS. 3A–E (SEQ ID NO.:3).

The three cDNA clones appear to be full-length by the criteria of having codons encoding methionine residues that are predicted to be the likely candidates as initiator methionines. These methionine codons are followed by amino acid sequences (deduced from the DNA) with properties suggesting that they are "signal-peptide" sequences. All three receptor cDNAs have stop codons at locations that permit these receptors to "fit" a putative seven-membrane spanning model, a model typical for G-protein-linked receptors. Most importantly, all three cloned receptors bind ligands and, when activated, are capable of activating intracellular effectors. These properties suggest that all three of the isolated clones encode full-length cDNAs.

FIG. 4 demonstrates the high degree of homology between the amino acid sequences encoded by the cDNAs from OK-O and ROS 15B. There is an overall 87% homology and a 77.8% amino acid identity between these two receptors. This high level of identity over long stretches of amino acids demonstrates that the amino acid sequence of the PTH receptor is evolutionarily conserved to a high degree. This allows the data from both OK-O and R15B to be extrapolated to other species, including human.

FIG. 5 shows the deduced amino acid sequences of all three cloned cDNAs lined up according to sequence homology. The OK-H sequence is identical to OK-O except in the C-terminus tail, where the OK-O sequence totals 585 amino acids whereas the OK-H sequence stops at 515 amino acids. This difference is attributable to a single nucleotide (G) deleted in the OK-H sequence compared to the OK-O sequence, causing a frame shift and early stop codon in the former. It is not known whether OK-O and OK-H represent the products of two separate genes or of a laboratory artifact.

Some G-protein-coupled receptors are encoded by intronless genes (Kobilka et al., Nature 329:75, 1987); Kobilka et al., J. Biol. Chem. 262:7321, 1987; Heckert et al., Mol. Endocrinol. 6:70, 1992; Kobilka et al., Science 238:650, 1987; Bonner et al., Science 237:527, 1987; Sunahara et al., Nature 347:80, 1990). To isolate a human PTH/PTHrP receptor cDNA, both a human cDNA library and a human genomic library were screened with a probe (BamHI/NotI) representing most of the coding region of the rat bone PTH/PTHrP receptor (FIGS. 3A–E). Screening the human kidney cDNA library led to the isolation of the clone HK-1 (FIGS. 6A–G) [SEQ ID NO.: 4]. Since one of the two EcoRI cloning sites of lambda GT10 proved to be eliminated as a result of the library construction, the HindIII/EcoRI phage fragment containing the cDNA insert and ~250 bp of the 37 kb (left) lambda arm was subcloned into the corresponding restriction sites in pcDNAI. DNA sequencing revealed that the cloned cDNA contained ~1000 bp of the 3' coding region and ~200 bp of the 3' non-coding region including an A-rich 3' end. The coding region 5' to the XhoI site was subsequently used to re-screen the library and led to the isolation of the clone HK-2 which, after subcloning into pcDNAI, proved to contain ~1400 bp of the coding region. For the third screening or the library, the PvuII/PstI fragment of HK-2 was used; the isolated clone HK-3 proved to be identical to HK-2.

The genomic library screening (~$10^6$ pfu) resulted in the isolation of four independent clones. Comparison of Southern blot analyses of restriction enzyme digests of these clones with that of normal genomic DNA, revealed that one 15 kb genomic clone, HPG1 (also referred to as HG4A), contained a SstI/SstI fragment that had the same size as one hybridizing DNA species from normal human genomic DNA digested with SstI (see below). The hybridizing 2.3 kb SstI/SstI DNA fragment and an ~8 kb XhoI fragment which comprised the SstI/SstI fragment were both subcloned into pcDNAI. Further Southern blot analysis of the SstI/SstI DNA fragment revealed that an ~1000 bp BamHI/SstI fragment encoded a portion of the human PTH/PTHrP receptor which later proved to represent the exon encoding the putative signal peptide and the 5' non-translated region which is interrupted by an ~1000 bp intron (FIG. 7).

To isolate the remaining ~450 nucleotides of the coding region, poly (A)+ RNA from human kidney was reverse transcribed after priming with H12 (FIG. 7). After single strand synthesis, two independent PCRs were performed using two different forward primers: i) a degenerate primer RK-1 based on the 5' coding end of the two previously cloned PTH/PTHrP receptors, OK-O and R15B; and ii) primer RK-2 based on the 5' non-coding region of HPGl. H-26 was used as the reverse primer for both reactions. Southern blot and restriction map analyses confirmed the expected size of the amplified DNA encoding the human PTH/PTHrP receptor. The blunt-ended PCR products encoding the 5' end of the human PTH/PTHrP were cloned into pcDNAI using the dephosphorylated EcoRV sites. Sequence analysis of each PCR clone confirmed their 5' nucleotide difference due to the difference in forward primer sequence, but revealed otherwise identical sequences. Nucleotide sequencing of both strands of the human PTH/PTHrP receptor cDNA revealed an open reading frame encoding a 593-amino acid protein (FIGS. 6A–G, SEQ ID NO.:4).

The full-length human kidney PTH/PTHrP receptor cDNA, HKrk, was constructed using the BamHI/PvuII fragment of PCR clone #2 and HK-2. Using the full-length cDNA encoding the human PTH/PTHrP receptor, Northern blot analysis of total RNA (~10 µg/lane) from human kidney and SaOS-2 cells revealed one major hybridizing DNA species of ~2.5 kb (FIG. 19). The XhoI digest of normal human genomic DNA, when probed with the same full-length cDNA (FIG. 20), revealed one major hybridizing species of about 5.5 kb, and two DNA species of 4 and 8 kb which weakly hybridized. These data suggest that the human PTH/PTHrP receptor is the product of a single gene. This full-length clone was then transiently expressed in COS-7 cells for functional and biological characterization by the methods cited above.

Comparison of the human receptor with the opposum kidney PTH/PTHrP receptor and the rat bone PTH/PTHrP receptor, revealed 81% and 91% amino acid sequence identity, respectively, and consequently a very similar hydrophobicity plot (FIG. 8). All extracellular cysteines including the two cysteine residues in the presumed signal peptide are conserved, as are all potential, extracellular N-glycosylation sites. A number of the amino acids which were not identical between the human kidney and rat bone PTH/PTHr receptors were found to be conserved between the human and the opposum receptors. These conserved amino acids include an Arg to Leu at 51, an Arg to Trp at 58, an Arg to His at 262, an Asp to His at 358, an Ile to Thr at 422, and a Thr to Leu at 427.

Biological Characterization

Functional characterization of the biological properties of the opossum and rat PTH/PTHrP receptors was performed in transiently transfected COS calls by a radioreceptor assay-technique using both $^{125}$I-PTHrP and $^{125}$I-NlePTH as radioligands, and by bioassays that measure ligand-stimulated cAMP accumulation, increase in intracellular free calcium, and stimulation of inositol phosphate metabolism, by the methods cited above.

FIG. 9 demonstrates that COS cells expressing OK-H bind $^{125}$I-PTHrP. These data also demonstrate that binding of PTHrP is inhibited when intact PTH (1–34) or PTH analogues which are shortened at their amino terminus (i.e. the 3–34 and 7–34 analogues, which contain Nle substitutions for methionine at positions 8 and 18 and a tyrosine substitution for phenylalanine at position 34) are used as competitors for binding. Similarly, binding of $^{125}$I-NlePTH to COS cells expressing OK-H was inhibited when PTHrP or PTHrP fragments were used as competitors. These data indicate that PTH and PTHrP both bind to the receptor encoded by OK-H.

FIG. 10 demonstrates that COS cells expressing OK-H increase their concentration of intracellular free calcium when exposed to NlePTH, but to a smaller extent (mean=39 nm), or not at all, when compared to COS cells expressing OK-O or R15B receptors (FIG. 12 and FIG. 14) and stimulated with NlePTH. Unlike COS cells expressing OK-O or R15B, COS cells expressing OK-H do not show a detectable increase in metabolism of inositol phosphate when stimulated with NlePTH (FIG. 15).

FIG. 11 demonstrates that COS cells expressing OK-O bind $^{125}$I-PTHrP. These data also demonstrate that binding of PTHrP is inhibited when intact PTH (1–34) or PTH analogues which are shortened at their amino terminus (i.e. the 3–34 and 7–34 analogues, which contain Nle substitutions for methionine at positions 8 and 18 and a tyrosine substitution for phenylalanine at position 34) are used as competitors for binding. Similarly, binding of $^{125}$I-NlePTH to COS cells expressing OK-H was inhibited when PTHrP or PTHrP fragments were used as competitors. These data indicate that PTH and PTHrP both bind to the receptor encoded by OK-O.

FIG. 12 demonstrates that COS cells expressing OK-O increase their concentration of intracellular free calcium and their rate of inositol phosphate metabolism after stimulation with NlePTH and PTHrP (FIG. 15).

FIG. 13 demonstrates that COS cells expressing R15B bind $^{125}$I-PTHrP. These data also demonstrate that binding of PTHrP is inhibited when intact PTH (1–34) or PTH analogues which are shortened at their amino terminus (i.e. the 3–34 and 7–34 analogues, which contain Nle substitutions for methionine at positions 8 and 18 and a tyrosine substitution for phenylalanine at position 34) are used as competitors for binding. Similarly, binding of $^{125}$I-NlePTH to COS cells expressing OK-H was inhibited when PTHrP or PTHrP fragments were used as competitors. These data indicate that PTH and PTHrP both bind to the receptor encoded by R15B.

FIG. 14 demonstrates that COS cells expressing R15B increase their concentration of intracellular calcium to an extent similar to stimulated COS cells expressing OK-O.

FIGS. 15A and 15B demonstrate that COS cells expressing R15B or OK-O increase their rate of phosphatidyl inositol hydrolysis, as evidenced by the rapid increase in inositol trisphosphate ($IP_3$) (FIG. 15B) and inositol bisphosphate ($IP_2$) (FIG. 15A) accumulation after stimulation of the cells with NlePTH or PTHrP. Conversely, COS cells expressing OK-H did not show any detectable increase in inositol trisphosphate and inositol bisphosphate accumulation after stimulation with NlePTH or PTHrP. These data suggest that the PTH receptor encoded by R15B and OK-O is coupled to phospholipase C, presumably through $G_p$. Since the only difference between OK-O and OK-H is in the cytoplasmic C-terminal tail, these data strongly suggest that the C-terminus of the PTH receptor encoded by OK-O and R15B is involved in the activation of phospholipase C.

FIG. 16 demonstrates that COS cells expressing R15B and OK-H increase cAMP accumulation after stimulation with NlePTH. Similar results were obtained in COS cells expressing OK-O. No cAMP stimulation was detected in COS cells transfected with the cDM8 vector alone. These data suggest that PTH receptor coupling to adenylate cyclase does not require the full length C-terminal cytoplasmic tail of the receptor.

These data demonstrate that all three PTH/PTHrP receptors cloned from both OK and ROS cell cDNA libraries bind the amino-terminal ligands of both peptides equivalently. Activation of all these receptors by ligand stimulates adenylate cyclase (as measured by increased intracellular cAMP), presumably through activation of one class of guanine nucleotide binding proteins (G-proteins). G-proteins have a trimeric peptide structure in which one of the subunits, alpha, is distinct, and the other two, beta and gamma, are identical or highly homologous. One of these G-proteins ($G_s$) contains G-alpha-"stimulatory" (G-alpha-s) which is involved in the activation of adenylate cyclase.

Binding of ligand to OK-O and R15B, but not to OK-H, also increases intracellular free calcium and stimulates metabolism of inositol phosphate. These properties strongly suggest that activation of both OK-O and R15B receptors by ligand results in stimulation of a second intracellular effector, phospholipase C. The coupling mechanism between these activated receptors and phospholipase C is likely to be a G-protein which is distinct from $G_s$. In contrast, the properties of the activated OK-H receptor which is truncated at the carboxy terminus, suggest that it may not activate phospholipase C, or that it activates phospholipase C inefficiently.

The biochemical role of the carboxy-terminal tail of the PTH/PTHrP receptor was further investigated by the construction of a carboxy-terminally-truncated rat receptor, R480, by standard PCR technology using R15B as a template and an upstream primer containing a stop codon inserted at position 481. Briefly, the upstream primer was a synthetic oligonucleotide based on nucleotides 1494–1513 of the rat cDNA sequence (see FIGS. 3A-E; SEQ ID NO.: 3) to which a stop codon and an XbaI cloning site were added. Thirty PCR cycles were carried out, each cycle consisting of 1 min at 92° C. for denaturation, 1 min at 60° C. for annealing, and 1 min at 72° C. for extension. The product was cut with NsiI and XbaI and purified by gel electrophoresis. R15B was sequentially digested with XbaI and NsiI, and the purified PCR product was then ligated into the XbaI-NsiI cut R15B vector. The resulting plasmid, R480, was amplified in bacteria and sequenced.

R480 encodes 480 amino acids that are identical to those in the 591 amino acids receptor. This truncated cDNA was expressed in COS-7 cells (transient expression) and in CHO cells (stable expression). Both COS-7 and CHO cells expressing the truncated receptor, R480, and the wild type receptor, RB, bind PTH(1–34) with equivalent affinities. When activated, R480 stimulates cAMP accumulation in COS7 and CHO cells as efficiently as does the wild type receptor. In contrast to the wild type receptor, R480 did not mediate any increase in [$Ca^{2+}$]i when stimulated by PTH in either the COS-7 cells or the CHO cells. These data indicate that the molecular requirements for activation of phospholipase C and adenylate cyclase by PTH/PTHrP receptor are distinct from each other, and point to a major role of the carboxy-terminal tail of the PTH/PTHrP receptor in coupling to phospholipase C but not to adenylate cyclase. Of course, it is also possible that activated PTH/PTHrP receptors may activate additional G-proteins and/or intracelluar effector molecules.

Analysis of COS-7 cells transfected with the cloned human PTH/PTHrP receptor demonstrated that radiolabelled PTH(1–34) and PTHrP(1–36) (~200,000 cpm) bound to the expressed receptors with similar efficiency (specific binding: 10.1±3.7% and 7.6±6.0%, respectively) (FIGS. 17A and 17C) to that observed for COS-7 cells expressing R15B (specific binding: 8.1+3.5% and 7.1+4.1%, respectively) (FIGS. 17B and 17D). The expressed human PTH/PTHrP receptors bound PTH(1–34) with 2-fold higher apparent Kd than did the rat bone PTH/PTHrP receptor: ~5 nM versus ~10 nM (FIGS. 17A-17D). However, despite their high degree of amino acid homology, the two receptors showed significant differences in affinity for PTH(3–34) and PTH(7–34). PTHrP(1–36) displayed a 2- to 4-fold lower affinity for the human PTH/PTHrP receptor than for the rat receptor (~35 nM for HKrk versus ~10 nM for R15B) which appeared more pronounced when PTHrP(1–36) was used as radioligand. The affinities for PTH(3–34) and PTH(7–34) were 7- and 35-fold higher with the expressed HKrK than with R15B (~7 nM versus ~45 nM for PTH(3–34), respectively; ~60 nM versus ~2000 nM for PTH(7–34), respectively). In COS-7 cells expressing either receptor, both PTH(1–34) and PTHrP(1–36) stimulated the increase in intracellular free calcium and cAMP accumulation to the same extent (FIG. 18).

Relationship of PTH/PTHrP Receptors

The amino acid sequence of the human PTH/PTHrP receptor displays a very high degree of conservation compared to the bone PTH/PTHrP receptor from rat, a eutherian mammal, while its sequence identity with the PTH/PTHrP receptor of the opossum, a marsupial mammal, is less marked. Like the opossum kidney and the rat bone receptor, the human kidney receptor induces an increase in both intracellular cAMP and intracellular free calcium when challenged with either PTH or PTHrP. Despite the high degree of homology between the human PTH/PTHrP receptor and the opossum and rat homologs, the transiently expressed human receptor has some functional characteristics that are distinct from those of the rat bone receptor. These include a slightly higher affinity for PTH(1–34) and a significantly descreased affinity for PTHrP(1–36). Higher affinities were observed for PTH(3–34) and in particular for PTH(7–34), the affinity of which for the human receptor was about 35-fold higher in comparison to the rat bone receptor. These findings may have significant implications for the future development of PTH/PTHrP analogues, since they predict that species-specific tissues would be the appropriate tissues for testing the potency of antagonists (and agonists) in vitro.

Relationship of PTH/PTHrP Receptors to Other Receptors

The biochemical properties of PTH and PTHrP receptors suggest that they are members of the class of membrane receptor molecules known as G-protein-linked membrane receptors. The structural features of well-characterized G-protein receptors indicate that they all have at least seven regions of several consecutive hydrophobic amino acids, each of which regions is of sufficient length to span the plasma membrane.

One subfamily of G-protein-linked membrane receptors, termed the glycopeptide receptor subfamily, includes receptors that bind and are activated by glycopeptide hormones (thyroid-stimulating hormone, luteinizing hormone, follicle-stimulating hormone, and chorionic gonadotropin). All of these receptors are characterized by (1) extensive putative amino-terminal extracellular domains (greater than 300 amino acids) that are thought to contain some or all of the ligand-binding domains, and (2) considerable amino-acid homology, particularly in the seven putative transmembrane domains. A second subfamily, termed the adrenergic/muscarinic subfamily, includes receptors that are activated-by small ligands, such as the catecholoamines, neuromuscular transmitters, and retinol. These receptors are all characterized by relatively short (25–75 amino acids) putative amino-terminal extracellular domains, as well as considerable amino acid homology, particularly in the seven putative transmembrane domains. Activation of these receptors by their ligands appears to involve at least several of the multiple transmembrane domains, and does not appear to involve the amino-terminal portion of the receptors.

Several structural characteristics which can be deduced from the predicted amino acid sequence of the rat PTH/PTHrP receptor (FIGS. 3A–E; SEQ ID NO: 3) indicate that the PTH/PTHrP is a G-protein-linked receptor. The amino terminus shows characteristic features of a signal peptide, including a hydrophobic domain and the presence of three consecutive leucine residues. This amino acid stretch of 20–28 amino acids may serve as a leader sequence, similar to the amino terminus preceding the extracellular domains of other glycoprotein receptors. There is also a cluster of seven hydrophobic segments which represent putative membrane-spanning domains (FIG. 19).

The predicted amino acid sequences of the opossum kidney, rat bone and human kidney PTH/PTHrp receptors indicate that they do not fit comfortably into either of these G-protein linked receptor subfamilies. Overall homology of the rat and human PTH/PTHrP receptors with the glycopeptide receptor and adrenergic/muscarinic subfamilies is approximately 10 to 20%, with a somewhat higher degree of homology within the transmembrane domains. The latter is to be expected because of the limited menu of hydrophobic amino acids that could occur in those regions. Twenty percent homology is far less than that found among the receptors generally accepted to be members of each of these subfamilies. Additionally, there are no portions of these sequences that have what could be characterized as intense homology (i.e., exactly matching amino acid sequences), even over limited regions.

Recent comparison with the newly characterized secretin and calcitonin receptors (Ishihara et al., EMBO J 10:1635, 1991; Lin et al., Science 254:1022, 1991) has revealed between 30 and 40% identity between these receptors and the PTH/PTHrP receptor. Although the PTH/PTHrP receptor is more than 100 amino acids longer than the calcitonin receptor, there is an ~32% identify between the amino acid sequences of the opossum kidney PTH/PTHrP receptor (SEQ ID NO.:2) and porcine kidney calcitonin receptor (GenBank accession no. M74420). A stretch of 17 out of 18 amino acids in the putative transmembrane domain VII are identical. Also, two out of four N-linked glycoslyation sites and the position of seven out of eight potentially extracellular cysteines are conserved. Major differences between the two receptors appear to lie in their $NH_2$-terminal and COOH-terminal domains. Comparison of amino acid sequences of the rat secretin receptor (GenBank accession no. X59132) and the human PTH/PTHrP receptor indicates that there is a 43% identity between these two receptors, with a stretch of 21 out of 25 amino acids of the putative transmembrane domain VII being identical. The similarity between the PTH/PTHrP, calcitonin and secretin receptors suggests that they represent a new family of seven transmembrane-spanning G protein-coupled receptors that activate adenylate cyclase. Given the amino acid sequences of these receptors, those skilled in art would be able to compare these sequences for regions of identity which would be useful in the design of nucleic acid probes which could then be used for the identification and isolation of other receptors which would belong to this family.

Deposit of Clones

Under the terms of the Budapest Treaty on the International Recognition of the Deposit of Microorganisms for the Purpose of Patent Procedure, the cDNA expression plasmids R15B, OK-O, and OK-H; the phage HPG1; and a plasmid (termed 8A6) containing part of the human clone have been deposited with the American Type Culture Collection (ATCC), where they bear the respective accession numbers ATCC No. 68571, 68572, 68573, 40998 and 68570. Applicants' assignee, The General Hospital Corporation, represents that the ATCC is a depository affording permanence of the deposits and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicants, assignee acknowledges its responsibility to replace the deposits should the depository be unable to furnish a sample when requested due to the condition of the deposit.

Polypeptides

Polypeptides according to the invention include the opossum and rat and human parathyroid hormone receptors as shown in FIGS. 1A–E, 2A–E, and 6A–G, respectively, and any other naturally-occurring receptor which can be produced by methods analogous to those used to clone and express these receptors, or by methods utilizing as a probe all or part of one or the sequences described herein. In addition, any analog or fragment of a PTH receptor capable of binding to a parathyroid hormone or a parathyroid hormone-related protein is within the invention.

Specific receptor analogs of interest include full-length or partial receptor proteins having an amino acid sequence which differs only by conservative amino acid substitutions: for example, substitution of one amino acid for another of the same class (e.g., valine for glycine; arginine for lysine, etc.), or by one or more non-conservative amino-acid substitutions, deletions, or insertions located at positions which do not destroy the receptor's ability to bind to parathyroid hormone or parathyroid hormone-related protein.

Specific receptor fragments of particular interest include, but are not limited to, portions of the receptor deduced to be extracellular from the primary amino acid sequence, using a hydrophobicity/hydrophilicity calculation such as the Chou-Fasman method (see, e.g., Chou and Fasman, Ann. Rev. Biochem. 47:251, 1978). Hydrophilic domains, particularly ones surrounded by hydrophobic stretches (e.g., transmembrane domains) of at least 10 amino acids, present themselves as strong candidates for extracellular domains. FIG. 21 illustrates a predicted arrangement of extracellular, intracellular, and transmembrane domains of one PTH receptor.

Examples of specific PTH receptor fragments include those with the following amino acid sequences (shown as standard single-letter symbols), derived from the deduced amino acid sequence of the R15B clone:
Extracellular Domains:
RP-1: TNETREREVFDRLGMIYTVG (SEQ ID NO.: 5)
RP-2: VLYSGFTLDEAERLTEEEL (SEQ ID NO.: 6)
RP-3: VTFFLYFLATNYYWILVEG (SEQ ID NO.: 7)
RP-4: Y-RATLANTGCWDLSSGHKKWIIQVP (SEQ ID NO.: 8)
RP-5: PYTEVSGTLWQIQMHYEM (SEQ ID NO.: 9)
RP-6: DDVFTKEEQIFLLHRAQA (SEQ ID NO.: 10)
Intracellular Domains:
RPi-7: FRRLHCTRNY (SEQ ID NO.: 11)
RPi-8: EKKYLWGFTL (SEQ ID NO.: 12)
RPi-9: VLATKLRETNAGRCDTRQQYRKLLK (SEQ ID NO.: 13)
These fragments were synthesized and purified by HPLC according to the method of Keutmann et al., (Endocrinology 117: 1230, 1984).
Expression of Polypeptides Polypeptides according to the invention may be produced by expression from a recombinant nucleic acid having a sequence encoding part or all of a cell receptor of the invention, using any appropriate expression system: e.g., transformation of a suitable host cell (either prokaryotic or eukaryotic) with the recombinant nucleic acid in a suitable expression vehicle (e.g., pcDNAI). The precise host cell used is not critical to the invention; however, in the case wherein the polypeptides of the invention include all or part of the PTH/PTHrP receptor, the following host cells are preferred: COS cells, LLC-PK1 cells, OK cells, AtT20 cells, and CHO cells. The method of transfection and the choice of expression vehicle will depend on the host system selected. Mammalian cell transfection methods are described, e.g., in Ausubel et al. (Current Protocols in Molecular Biology, John Wiley & Sons, New York, 1989); expression vehicles may be chosen from those discussed, e.g., in Cloning Vectors: A Laboratory Manual (P. H. Pouwels et al., 1985, Supp. 1987).

Stably transfected cells are produced via integration of receptor DNA into the host cell chromosomes. Suitable DNAs are inserted into pcDNA, pcDNAI-Neo, or another suitable plasmid, and then cells are transfected with this plasmid with or without cotransfection with psV-2-Neo, or psV-2-DHFR by standard electroporation, calcium phosphate, and/or DEAE/Dextran techniques. Selection of transfected cells is performed using progressively increasing levels of G418 (Geneticin, GIBCO), and if necessary, methotrexate.

DNA sequences encoding the polypeptides of the invention can also be expressed in a prokaryotic host cell. DNA encoding a cell receptor or receptor fragment is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. For example, *E. coli* may be transformed using derivatives of pBR322, a plasmid constructed by Bolivar et al. (Gene 2: 95, 1977) using fragments derived from three naturally-occurring plasmids, two isolated from species of *Salmonella*, and one isolated from *E. coli*. pBR322 contains genes from ampicillin and tetracycline resistance, and thus provides multiple selectable markers which can be either retained or destroyed in constructing the desired expression vector. Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., Nature 198: 1056, 1977) and the tryptophan (Trp) promoter systems (Goeddel et al., Nucl. Acids Res. 8: 4057, 1980) as well as the lambda-derived $P_L$ promoter and N-gene ribosome binding site (Simatake et al., Nature 292:128, 1981).

The nature of the cell receptor proteins of the invention is such that, upon expression within a cell, it is moved to the cellular membrane and partially through the membrane, so that part of it remains embedded in the membrane, part extends outside the cell, and part remains within the cell. Transformed cells bearing such embedded cell receptors may themselves be employed in the methods of the invention, or the receptor protein may be extracted from the membranes and purified.

Expression of peptide fragments lacking the hydrophobic portions of the protein responsible for anchoring the intact protein in the cellular membrane would not be expected to become embedded in the membrane; whether they remain within the cell or are secreted into the extracellular medium depends upon whether or not a mechanism promoting secretion (e.g., a signal peptide) is included. If secreted, the polypeptide of the invention can be harvested from the medium; if not, the cells must be broken open and the desired polypeptide isolated from the entire contents of the cells. Specific examples of polypeptides which might be expressed include, without limitation:

1) Amino-terminal portion comprising amino acids 1–192, including the putative leader sequence, of the rat bone PTH/PTHrP receptor as shown in FIG. 3.

2) Amino-terminal portion comprising amino acids 27–192, excluding the putative leader sequence, of the rat bone PTH/PTHrP receptor as shown in FIG. 3.

3) The full-length PTH/PTHrP receptor from rat bone, as shown in FIG. 3.

4) RP-1 (as described above).

5) RP-2 (as described above).

The polypeptide of the invention can be readily purified using affinity chromatography. Antibodies to these polypeptides, or the receptor specific ligands, (e.g., the hormones PTH and PTHrP for the PTH/PTHrP receptor) may be covalently coupled to a solid phase support such as Sepharose 4 CNBr-activated sepharose (Pharmacia), and used to separate the polypeptide of the invention from any contaminating substances. Typically 1 mg of ligand or antibody will be incubated with CNBr-activated sepharose at 4° C. for 17–20 h (with shaking). The sepharose is rinsed with 1 M Tris HCL (pH8) to block excess active sites. The sepharose-PTH, sepharose-PTHrP, or sepharose-antibody is then incubated with the crude polypeptide in phosphate-buffered saline (pH 7.4) at 4° C. for 2 h (with shaking). The sepharose is then typically packed in a column, thoroughly washed with PBS (typically 10 times the column volume), and eluted with dilute HCl in $H_2O$ (pH 1.85). The eluate may then be concentrated by lyophylization and its purity checked, for example, by reverse phase HPLC.

Anti-Cell Receptor Antibodies

Cell receptor or receptor fragments of the invention may be used to generate antibodies by any conventional method well known to those skilled in the art, including those which generate polyclonal antibodies and those which generate monoclonal antibodies. For example, the deduced amino acid sequence of the PTH receptor reveals a protein structure that appears to have several transmembrane (i.e., hydrophobic) domains interspersed with presumably extracellular and intracellular regions (see FIG. 21) analogous to those found in other G protein-linked receptors. This information can be used to guide the selection of regions of the receptor protein which would be likely to be exposed on the cell surface, and thus would be presented to antibodies in vivo. A short peptide representing one or more of such regions may be synthesized (e.g., chemically or by recombinant DNA techniques) and used to immunize an animal (e.g., a rabbit or a mouse) to generate polyclonal or monoclonal antibodies. For example, certain of the peptides of the PTH/PTHrP receptor listed above (RP-1, RP-5 and RP-6) have been chemically synthesized using standard techniques and used to generate polyclonal antibodies in rabbits by the following procedure:

A preparation of a given peptide emulsified with complete Freund's Adjuvant is injected intradermally into rabbits. Booster injections are emulsified in or complete adjuvant and injected at monthly intervals.

Antibody titer is assessed using either of two methods. First, serial dilutions of the antiserum in it normal rabbit serum are incubated with $^{125}I$-labelled PTH/PTHrP receptor fragment by standard methods (e.g., see Segre et al., supra) for 24 h at 4° C. The bound $^{125}I$-PTH/PTHrP receptor fragments are separated from unbound by addition of 100 µl of second antibody (anti-rabbit IgG, Sigma) diluted 1:20 and 1 ml of 5% polyethylene glycol, followed by centrifugation at 2000 rpm for 30 min. at 4° C. The supernatant is removed and the pellet analyzed for radioactivity in a γ-counter. In the second method, cell lines expressing either native (e.g., ROS 17/2.8, OK, SaOS-02 cells) or recombinant (COS cells or CHO cells transfected with R15B, OK-O or OK-H) PTH/PTHrP receptors are incubated with serially diluted antibody at 4° C., 20° C. or 37° C. for 1–4 h. The cells are rinsed with PBS (x3) and incubated for 2 h at 4° C. with $^{125}I$-labelled (NEN, Dupont) or FITC-labelled (Sigma) second antibodies. After rinsing (x3 with PBS), the cells were either lysed with 0.1 M NaOH and counted in γ-counter (if $^{125}I$-labelled second antibody was used) or fixed with 1% paraformaldehyde and examined by fluorescent microscopy (if FITC-labelled second antibody was used).

Another method for producing antibodies utilizes as antigen the intact cell receptor protein of the invention expressed on the surface of cells (e.g., mammalian cells, such as COS cells, transfected with DNA encoding the receptor). Such cells are prepared by standard techniques, e.g., by the DEAE-dextran transfection method, using a vector encoding and capable of directing high-level expression of the cell receptor. Such cells may be used to generate polyclonal or monoclonal antibodies. For example, monoclonal antibodies specific for the PTH/PTHrP receptor may be produced by the following procedure:

Intact COS cells expressing high levels of rat recombinant PTH receptors on the cell surface are injected intraperitoneally (IP) into Balb-c mice (Charles River Laboratories, Willmington, Mass.). The mice are boosted every 4 weeks by IP injection, and are hyperimmunized by an intravenous (IV) booster 3 days before fusion. Spleen cells from the mice are isolated and are fused by standard methods to myeloma cells. Hybridomas are selected in standard hypoxanthine/aminopterin/thymine (HAT) medium, according to standard methods. Hybridomas secreting antibodies which recognize the PTH receptor are initially identified by screening with cell lines which naturally express abundant copies of the PTH-receptor per cell (such as ROS17/2.8 or OK cells), using standard immunological techniques. Those hybridomas which produce antibodies capable of binding to the PTH receptor are cultured and subcloned. Secondary screening with radioreceptor and cAMP stimulation assays can then be performed to further characterize the monoclonal antibodies (see below).

Screening for PTH Receptor Antagonists and Agonists

The polypeptides and antibodies of the invention and other compounds may be screened for PTH-competition and for antagonistic or agonistic properties using the assays described herein.

In one example, those antibodies that recognize the PTH receptor on the intact cells are screened for their ability to compete with PTH or PTHrP for binding to a PTH/PTHrP receptor. Cells expressing PTH receptor on the cell surface are incubated with the $^{125}I$-PTH analog, $^{125}I$-NlePTH or $^{125}I$-PTHrP in the presence or absence of the polyclonal or monoclonal antibody to be tested, for 4 h at 15° C. The antibody used may be from crude antiserum, cell medium, or ascites, or in purified form. After incubation, the cells are rinsed with binding buffer (e.g., physiological saline), lysed, and quantitatively analyzed do for radioactivity using a gamma-counter. Antibodies that reduce binding of the PTH analog to the PTH receptor are classified as competitive; those which do not are noncompetitive.

Compounds, including antibodies and polypeptides, may be screened for their agonistic or antagonistic properties using the cAMP accumulation, intracellular calcium, and/or inositol phosphate assays described above. Cells expressing PTH receptor on the cell surface are incubated with PTH, PTH-receptor antibody, or a combination of both, for 5–60 minutes at 37° C., in the presence of 2 mM IBMX (3-isobutyl-1-methyl-xanthine, Sigma, St. Louis, Mo.). Cyclic AMP accumulation is measured by specific radio-immunoassay, as described above. A compound that competes with PTH for binding to the PTH receptor, and that inhibits the effect of PTH on cAMP accumulation, is considered a competitive PTH antagonist. Conversely, a compound that does not compete for PTH binding to the PTH receptor, but which still prevents PTH activation of cAMP accumulation (presumably by blocking the receptor activation site) is considered a non-competitive antagonist. A compound that competes with PTH for binding to the PTH receptor, and which stimulates cAMP accumulation in the presence or absence of PTH, is a competitive agonist. A compound that does not compete with PTH for binding to the PTH receptor but which is still capable of stimulating cAMP accumulation in the presence or absence of PTH, or which stimulates a higher accumulation than that observed by PTH alone, would be considered a non-competitive agonist.

Use

The polypeptides, antibodies, and other compounds of the invention are useful for the diagnosis, classification, prognosis, and/or treatment of disorders which may be characterized as related to the interaction between a cell receptor of the invention and its specific ligand. For example, some forms of hypercalcemia and hypocalcemia are related to the interaction between PTH and PTHrP and the PTH/PTHrP receptor(s). Hypercalcemia is an condition in which there is an abnormal elevation in serum calcium level; it is often associated with other diseases, including hyperparathyroidism, osteoporosis, carcinomas of the breast, lung and prostrate, epidermoid cancers of the head and neck of the esophagus, multiple myeloma, and hypernephroma. Hypocalcemia, a condition in which the serum calcium level is abnormally low, may result from a deficiency of effective PTH, e.g., following thyroid surgery.

In a first example, the compounds of the invention are used to manufacture diagnostic agents which are used as diagnostic tools to diagnose hypercalcemia and to distinguish between hypercalcemic conditions, i.e., to differentiate hypercalcemia mediated by PTH or PTHrP (e.g., hyperparathyroidism and humoral hypercalcemia of malignancy), from hypercalcemia associated with diseases which do not involve these factors (e.g., local osteolytic hypercalcemia mediated by the presence of metastatic tumor cells in direct contact with bone, and certain rare types of malignancy-related hypercalcemias mediated by an increase of humoral factors, such as osteoclast activating factor (interleukin), lymphotoxin, calcitriol, type E prostaglandins, and vitamin D-like sterols).

In one method of diagnosis, serum total and/or ionized calcium levels are measured by standard techniques before and after the administration of the PTH or PTHrP antagonists of the invention. PTH or PTHrP related hypercalcemias would be detectable as a decrease in serum calcium levels following administration of the antagonist of the invention. In contrast, for hypercalcemic conditions mediated by factors other than PTH or PTHrP, the serum calcium levels would remain unchanged even after administration of the antagonist.

Another diagnostic application of the invention permits measurement of the level of PTH or PTHrP in a biological sample in order to diagnose PTH or PTHrP related tumors, e.g., tumors which are associated with humoral hypercalcemia of malignancy, and for monitoring the levels of PTH or PTHrP during cancer therapy. This method involves assaying binding of the recombinant parathyroid hormone receptor of the invention to PTH or PTHrP present in a tissue sample, using the binding assay described herein. The level of binding may be determined directly (e.g., by using radioactively labelled PTH receptor, and assaying the radioactivity bound to endogenous PTH). Alternatively, binding of PTH receptor to the sample (e.g., a tissue section) may be followed by staining of the tissue sections with an antibody specific for the PTH receptor, using standard immunological techniques (Chin et al., Hybridoma 5:339, 1986).

In a third diagnostic approach, one could stably transfect cell lines (by the methods described in Ausubel et al., *Current Protocols in Molecular Biology*, Wiley Publishers, New York, 1987) with a PTH receptor gene linked to an appropriate promoter (e.g., the metallothionine promoter). Alternatively, the PTH/PTHrP receptor could be expressed from a eukaryotic vector, i.e., pcDNAI, and cotransfected with a mutant DHFR gene that will allow further gene amplification via methotrexate selection (Simonsen et al., Proc. Natl. Acad. Sci., 80:2495–2499, 1983). Such high-level expression of the gene produces an immortal cell line which is oversensitive to PTH or PTHrP. Such cells provide a particularly useful tool for detecting serum blood levels of PTH or PTHrP. Such a cell line may be used for diagnosis of conditions involving elevated PTH or PTHrP levels (e.g., those described above) or for conditions involving unusually low levels of PTH or PTHrP (e.g., those described above). Such a cell line is also useful for monitoring the regression or increase of PTH or PTHrP levels during therapy for hypercalcemia or hypocalcemia, respectively.

A patient who is suspected of being hypercalcemic may be treated using the compounds of the invention. Rapid intervention is important because symptoms may appear abruptly and, unless reversed, can be fatal. In one application, serum calcium levels are stabilized by an immediate course of treatment which includes antagonists of PTH or PTHrP. Such antagonists include the compounds of the invention which have been determined (by the assays described herein) to interfere with PTH receptor-mediated cell activation. To administer the antagonist, the appropriate antibody or peptide (is used in the manufacture of a medicament, generally by being formulated in an appropriate carrier such as physiological saline, and administered intravenously, at a dosage that provides adequate competition for PTH or PTHrP binding to the PTH receptor (e.g., a dosage sufficient to lower the serum calcium level to below 10 mg/dl). Typical dosage would be 1 ng to 10 mg of the antibody or peptide per kg body weight per day. Treatment may be repeated as necessary for long term maintenance of acceptable calcium levels (i.e., levels <10.1 mg/dl). This may be necessary for acute treatment of an underlying disease condition triggering hypercalcemia; or it may used, e.g., for chronic treatment of conditions such as osteoporosis.

In another application, the compounds of the invention which have been characterized, according to the methods of the invention, to be agonists are used therapeutically to treat hypocalcemia: e.g., that resulting from the partial or complete surgical removal of the parathyroid glands. Agonists may be formulated in a suitable carrier (e.g., physiological saline) and are preferably administered intravenously in a dosage that causes a rise in serum calcium to an acceptable level (i.e., approximately 8 mg/dl). A useful dosage range would be 1 ng to 10 mg of the agonist per kg body weight per day. Treatment may be repeated as necessary to maintain suitable serum calcium levels; long term treatment may be necessary for patients who have undergone parathyroid gland removal.

The nucleic acids of the invention may also be used therapeutically. Oligonucleotides which are antisense to PTH receptor mRNA (or nucleic acid constructs which express RNA that is antisense to PTH receptor mRNA) may be utilized as an anticancer therapy. This approach is useful, e.g., for hypercalcemias resulting from a genomic rearrangement or amplification which increases the amount or activity of PTH receptor, PTH or PTHrP. The method would involve introduction of the antisense oligonucleotide into the tumor cells in vivo. The antisense strand hybridizes with endogenous PTH receptor mRNA, interfering with translation of the protein, thereby reducing production of PTH receptor in such cells, and reducing PTH/PTHrP-associated neoplastic growth. Methods for antisense design and introduction into host cells are described, for example, in Weinberg et al., U.S. Pat. No. 4,740,463, herein incorporated by reference.

The biochemical characterization of the OK-H, OK-O and R15B PTH/PTHrP receptors of the invention demonstrate that the two transduction pathways now known to be triggered by the interaction of PTH with its receptor are distinct and may be separated. The predicted amino acid sequences of these receptors indicate that OK-H, which does not appear to activate inositol phosphate metabolism to any detectable degree, is 70 amino acids shorter at the carboxy-terminus than OK-O or R15B. By using the sequences of the invention and the information disclosed herein, one could clone and then alter (e.g. by site-directed mutagenesis) PTH/PTHrP receptor genes from any species to generate PTH/PTHrP receptors which do not activate phospholipase C. This could potentially allow the separation of different PTH-mediated actions, including bone resorption and bone formation, and could of great importance for the treatment of various bone disorders such as osteoporosis.

Nucleic acids of the invention which encode a PTH receptor may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of PTH receptor in selected tissues (e.g., the osteo calcin promoter for bone). Such promoters are used to direct tissue-specific expression of the PTH receptor in the transgenic animal. The form of PTH receptor utilized can be one which encodes a PTH receptor similar to that of the animal species used, or it can encode the PTH receptor homolog of a different species. In one particular example, transgenic chickens are engineered to express the PTH receptor from a promoter which directs high-level expression in chicken oviducts. Such an animal is expected to produce eggs with higher calcium content, and thus harder shells.

Other Embodiments

Other embodiments are within the following claims. For example, the nucleic acid of the invention includes genes or cDNAs or RNAs originally isolated from any vertebrate species, including birds or mammals such as marsupials, rodents, or humans. The high degree of homology demonstrated for the PTH receptors from such diverse species as opossum, rat, and human indicates that the methods of isolating PTH receptors disclosed herein will be broadly applicable to the isolation of related cell receptors from a wide variety of species.

SEQUENCE LISTING

<160> NUMBER OF SEQ ID NOS: 21

<210> SEQ ID NO 1
<211> LENGTH: 1862
<212> TYPE: DNA
<213> ORGANISM: Didelphoidea
<220> FEATURE:
<221> NAME/KEY: CDS
<222> LOCATION: (98)...(1642)

<400> SEQUENCE: 1

```
tgggcacagc caccctgttg gtagtccagg ggccagccca ctgagctggc atatcagctg      60
gtggccccgt tggactcggc cctagggaac ggcggcg atg gga gcg ccc cgg atc     115
                                            Met Gly Ala Pro Arg Ile
                                              1               5 tcg cac agc ctt gcc ttg ctc ctc tgc tgc tcc gtg ctc agc tcc gtc     163
Ser His Ser Leu Ala Leu Leu Leu Cys Cys Ser Val Leu Ser Ser Val
             10                  15                  20 tac gca ctg gtg gat gcc gat gat gtc ata acg aag gag gag cag atc     211
Tyr Ala Leu Val Asp Ala Asp Asp Val Ile Thr Lys Glu Glu Gln Ile
         25                  30                  35 att ctt ctg cgc aat gcc cag gcc cag tgt gag cag cgc ctg aaa gag     259
Ile Leu Leu Arg Asn Ala Gln Ala Gln Cys Glu Gln Arg Leu Lys Glu
     40                  45                  50 gtc ctc agg gtc cct gaa ctt gct gaa tct gcc aaa gac tgg atg tca     307
Val Leu Arg Val Pro Glu Leu Ala Glu Ser Ala Lys Asp Trp Met Ser
 55                  60                  65                  70 agg tct gca aag aca aag aag gag aaa cct gca gaa aag ctt tat ccc     355
```

|  |  |  |  |  |  |  |  |  |  |  |  |  |  |  |
|---|---|---|---|---|---|---|---|---|---|---|---|---|---|---|
| Arg | Ser | Ala | Lys | Thr | Lys | Lys | Glu | Lys | Pro | Ala | Glu | Lys | Leu | Tyr | Pro |
|  |  |  |  | 75 |  |  |  | 80 |  |  |  |  | 85 |  |

| cag | gca | gag | gag | tcc | agg | gaa | gtt | tct | gac | agg | agc | cgg | ctg | cag | gat | 403 |
|---|---|---|---|---|---|---|---|---|---|---|---|---|---|---|---|---|
| Gln | Ala | Glu | Glu | Ser | Arg | Glu | Val | Ser | Asp | Arg | Ser | Arg | Leu | Gln | Asp |  |
|  |  |  | 90 |  |  |  |  | 95 |  |  |  |  | 100 |  |  |  |

| ggc | ttc | tgc | cta | cct | gag | tgg | gac | aac | att | gtg | tgc | tgg | cct | gct | gga | 451 |
|---|---|---|---|---|---|---|---|---|---|---|---|---|---|---|---|---|
| Gly | Phe | Cys | Leu | Pro | Glu | Trp | Asp | Asn | Ile | Val | Cys | Trp | Pro | Ala | Gly |  |
|  |  | 105 |  |  |  |  | 110 |  |  |  |  | 115 |  |  |  |  |

| gtg | ccc | ggc | aag | gtg | gtg | gcc | gtg | ccc | tgc | ccc | gac | tac | ttc | tac | gac | 499 |
|---|---|---|---|---|---|---|---|---|---|---|---|---|---|---|---|---|
| Val | Pro | Gly | Lys | Val | Val | Ala | Val | Pro | Cys | Pro | Asp | Tyr | Phe | Tyr | Asp |  |
|  | 120 |  |  |  | 125 |  |  |  |  | 130 |  |  |  |  |  |  |

| ttc | aac | cac | aaa | ggc | cga | gcc | tat | cgg | cgc | tgt | gac | agc | aat | ggc | agc | 547 |
|---|---|---|---|---|---|---|---|---|---|---|---|---|---|---|---|---|
| Phe | Asn | His | Lys | Gly | Arg | Ala | Tyr | Arg | Arg | Cys | Asp | Ser | Asn | Gly | Ser |  |
| 135 |  |  |  | 140 |  |  |  |  | 145 |  |  |  |  | 150 |  |  |

| tgg | gag | ctg | gtg | cct | ggg | aac | aac | cgg | aca | tgg | gcg | aat | tac | agc | gaa | 595 |
|---|---|---|---|---|---|---|---|---|---|---|---|---|---|---|---|---|
| Trp | Glu | Leu | Val | Pro | Gly | Asn | Asn | Arg | Thr | Trp | Ala | Asn | Tyr | Ser | Glu |  |
|  |  |  |  | 155 |  |  |  |  | 160 |  |  |  |  | 165 |  |  |

| tgt | gtc | aag | ttt | ctg | acc | aac | gag | acc | cgg | gaa | cgg | gaa | gtc | ttt | gat | 643 |
|---|---|---|---|---|---|---|---|---|---|---|---|---|---|---|---|---|
| Cys | Val | Lys | Phe | Leu | Thr | Asn | Glu | Thr | Arg | Glu | Arg | Glu | Val | Phe | Asp |  |
|  |  |  | 170 |  |  |  |  | 175 |  |  |  |  | 180 |  |  |  |

| cgc | ctc | gga | atg | atc | tac | act | gtg | ggc | tac | tcc | atc | tct | ctg | ggc | tcc | 691 |
|---|---|---|---|---|---|---|---|---|---|---|---|---|---|---|---|---|
| Arg | Leu | Gly | Met | Ile | Tyr | Thr | Val | Gly | Tyr | Ser | Ile | Ser | Leu | Gly | Ser |  |
|  |  | 185 |  |  |  |  | 190 |  |  |  |  | 195 |  |  |  |  |

| ctc | act | gtg | gct | gtg | ctg | att | ctg | ggt | tac | ttt | agg | agg | tta | cat | tgc | 739 |
|---|---|---|---|---|---|---|---|---|---|---|---|---|---|---|---|---|
| Leu | Thr | Val | Ala | Val | Leu | Ile | Leu | Gly | Tyr | Phe | Arg | Arg | Leu | His | Cys |  |
|  | 200 |  |  |  | 205 |  |  |  |  | 210 |  |  |  |  |  |  |

| acc | cga | aac | tac | att | cac | atg | cat | ctc | ttc | gtg | tcc | ttt | atg | ctc | cgg | 787 |
|---|---|---|---|---|---|---|---|---|---|---|---|---|---|---|---|---|
| Thr | Arg | Asn | Tyr | Ile | His | Met | His | Leu | Phe | Val | Ser | Phe | Met | Leu | Arg |  |
| 215 |  |  |  | 220 |  |  |  |  | 225 |  |  |  |  | 230 |  |  |

| gct | gta | agc | atc | ttc | atc | aag | gat | gct | gtg | ctc | tac | tcg | ggg | gtt | tcc | 835 |
|---|---|---|---|---|---|---|---|---|---|---|---|---|---|---|---|---|
| Ala | Val | Ser | Ile | Phe | Ile | Lys | Asp | Ala | Val | Leu | Tyr | Ser | Gly | Val | Ser |  |
|  |  |  |  | 235 |  |  |  |  | 240 |  |  |  |  | 245 |  |  |

| aca | gat | gaa | atc | gag | cgc | atc | acc | gag | gag | gag | ctg | agg | gcc | ttc | aca | 883 |
|---|---|---|---|---|---|---|---|---|---|---|---|---|---|---|---|---|
| Thr | Asp | Glu | Ile | Glu | Arg | Ile | Thr | Glu | Glu | Glu | Leu | Arg | Ala | Phe | Thr |  |
|  |  |  | 250 |  |  |  |  | 255 |  |  |  |  | 260 |  |  |  |

| gag | cct | ccc | cct | gct | gac | aag | gcg | ggt | ttt | gtg | ggc | tgc | aga | gtg | gcg | 931 |
|---|---|---|---|---|---|---|---|---|---|---|---|---|---|---|---|---|
| Glu | Pro | Pro | Pro | Ala | Asp | Lys | Ala | Gly | Phe | Val | Gly | Cys | Arg | Val | Ala |  |
|  |  | 265 |  |  |  |  | 270 |  |  |  |  | 275 |  |  |  |  |

| gta | acc | gtc | ttc | ctt | tac | ttc | ctg | acc | acc | aac | tac | tac | tgg | atc | ctg | 979 |
|---|---|---|---|---|---|---|---|---|---|---|---|---|---|---|---|---|
| Val | Thr | Val | Phe | Leu | Tyr | Phe | Leu | Thr | Thr | Asn | Tyr | Tyr | Trp | Ile | Leu |  |
|  | 280 |  |  |  | 285 |  |  |  |  | 290 |  |  |  |  |  |  |

| gtg | gaa | ggc | ctc | tac | ctt | cac | agc | ctc | atc | ttc | atg | gct | ttt | ttc | tct | 1027 |
|---|---|---|---|---|---|---|---|---|---|---|---|---|---|---|---|---|
| Val | Glu | Gly | Leu | Tyr | Leu | His | Ser | Leu | Ile | Phe | Met | Ala | Phe | Phe | Ser |  |
| 295 |  |  |  | 300 |  |  |  |  | 305 |  |  |  |  | 310 |  |  |

| gag | aaa | aag | tat | ctc | tgg | ggt | ttc | aca | tta | ttt | ggc | tgg | ggc | ctc | cct | 1075 |
|---|---|---|---|---|---|---|---|---|---|---|---|---|---|---|---|---|
| Glu | Lys | Lys | Tyr | Leu | Trp | Gly | Phe | Thr | Leu | Phe | Gly | Trp | Gly | Leu | Pro |  |
|  |  |  |  | 315 |  |  |  |  | 320 |  |  |  |  | 325 |  |  |

| gcc | gtg | ttt | gtc | gct | gtg | tgg | gtg | acc | gtg | agg | gct | aca | ctg | gcc | aac | 1123 |
|---|---|---|---|---|---|---|---|---|---|---|---|---|---|---|---|---|
| Ala | Val | Phe | Val | Ala | Val | Trp | Val | Thr | Val | Arg | Ala | Thr | Leu | Ala | Asn |  |
|  |  | 330 |  |  |  |  | 335 |  |  |  |  | 340 |  |  |  |  |

| act | gag | tgc | tgg | gac | ctg | agt | tcg | ggg | aat | aag | aaa | tgg | atc | ata | cag | 1171 |
|---|---|---|---|---|---|---|---|---|---|---|---|---|---|---|---|---|
| Thr | Glu | Cys | Trp | Asp | Leu | Ser | Ser | Gly | Asn | Lys | Lys | Trp | Ile | Ile | Gln |  |
|  |  | 345 |  |  |  |  | 350 |  |  |  |  | 355 |  |  |  |  |

| gtg | ccc | atc | ctg | gca | gct | att | gtg | gtg | aac | ttt | att | ctt | ttt | atc | aat | 1219 |
|---|---|---|---|---|---|---|---|---|---|---|---|---|---|---|---|---|
| Val | Pro | Ile | Leu | Ala | Ala | Ile | Val | Val | Asn | Phe | Ile | Leu | Phe | Ile | Asn |  |
|  | 360 |  |  |  | 365 |  |  |  |  | 370 |  |  |  |  |  |  |

| ata | atc | aga | gtc | ctg | gct | act | aaa | ctc | cgg | gag | acc | aat | gca | ggg | aga | 1267 |
|---|---|---|---|---|---|---|---|---|---|---|---|---|---|---|---|---|
| Ile | Ile | Arg | Val | Leu | Ala | Thr | Lys | Leu | Arg | Glu | Thr | Asn | Ala | Gly | Arg |  |
| 375 |  |  |  | 380 |  |  |  |  | 385 |  |  |  |  | 390 |  |  |

```
tgt gac acg agg caa cag tat aga aag ctg ctg aag tcc acg cta gtc      1315
Cys Asp Thr Arg Gln Gln Tyr Arg Lys Leu Leu Lys Ser Thr Leu Val
                395                 400                 405 ctc atg ccg cta ttt ggg gtg cac tac atc gtc ttc atg gcc acg ccg      1363
Leu Met Pro Leu Phe Gly Val His Tyr Ile Val Phe Met Ala Thr Pro
            410                 415                 420 tac aca gaa gta tca ggg att ctt tgg caa gtc caa atg cac tat gaa      1411
Tyr Thr Glu Val Ser Gly Ile Leu Trp Gln Val Gln Met His Tyr Glu
        425                 430                 435 atg ctc ttc aat tca ttc cag gga ttt ttc gtt gcc att ata tac tgt      1459
Met Leu Phe Asn Ser Phe Gln Gly Phe Phe Val Ala Ile Ile Tyr Cys
    440                 445                 450 ttc tgc aat gga gag gta caa gca gag atc aag aag tca tgg agc cga      1507
Phe Cys Asn Gly Glu Val Gln Ala Glu Ile Lys Lys Ser Trp Ser Arg
455                 460                 465                 470 tgg acc ctg gcc ttg gac ttc aag cgg aag gcc cgg agt ggc agc agt      1555
Trp Thr Leu Ala Leu Asp Phe Lys Arg Lys Ala Arg Ser Gly Ser Ser
                475                 480                 485 acc tac agc tat ggc ccc atg gtg tca cat aca agt gtc acc aat gtg      1603
Thr Tyr Ser Tyr Gly Pro Met Val Ser His Thr Ser Val Thr Asn Val
            490                 495                 500 gga cct cga ggg ggc tgg cct tgt ccc tca gcc ctc gac tagctcctgg       1652
Gly Pro Arg Gly Gly Trp Pro Cys Pro Ser Ala Leu Asp
        505                 510                 515 ggctggagcc agtgccaatg ccatcacca gttgcctggc tatgtgaagc atggttccat     1712
ttctgagaac tcattgcctt catctggccc agagcctggc accaaagatg acgggtatct    1772
caatggctct ggactttatg agccaatggt tggggaacag ccccctccac tcctggagga    1832
ggagagagag acagtcatgt gacccatatc                                     1862

<210> SEQ ID NO 2
<211> LENGTH: 1863
<212> TYPE: DNA
<213> ORGANISM: Didelphoidea
<220> FEATURE:
<221> NAME/KEY: CDS
<222> LOCATION: (98)...(1852)

<400> SEQUENCE: 2
tgggcacagc caccctgttg gtagtccagg ggccagccca ctgagctggc atatcagctg     60
gtggccccgt tggactcggc cctagggaac ggcggcg atg gga gcg ccc cgg atc     115
                                         Met Gly Ala Pro Arg Ile
                                           1               5 tcg cac agc ctt gcc ttg ctc ctc tgc tgc tcc gtg ctc agc tcc gtc      163
Ser His Ser Leu Ala Leu Leu Leu Cys Cys Ser Val Leu Ser Ser Val
        10                  15                  20 tac gca ctg gtg gat gcc gat gat gtc ata acg aag gag gag cag atc      211
Tyr Ala Leu Val Asp Ala Asp Asp Val Ile Thr Lys Glu Glu Gln Ile
    25                  30                  35 att ctt ctg cgc aat gcc cag gcc cag tgt gag cag cgc ctg aaa gag      259
Ile Leu Leu Arg Asn Ala Gln Ala Gln Cys Glu Gln Arg Leu Lys Glu
40                  45                  50 gtc ctc agg gtc cct gaa ctt gct gaa tct gcc aaa gac tgg atg tca      307
Val Leu Arg Val Pro Glu Leu Ala Glu Ser Ala Lys Asp Trp Met Ser
55                  60                  65                  70 agg tct gca aag aca aag aag gag aaa cct gca gaa aag ctt tat ccc      355
Arg Ser Ala Lys Thr Lys Lys Glu Lys Pro Ala Glu Lys Leu Tyr Pro
                75                  80                  85 cag gca gag gag tcc agg gaa gtt tct gac agg agc cgg ctg cag gat      403
Gln Ala Glu Glu Ser Arg Glu Val Ser Asp Arg Ser Arg Leu Gln Asp
```

-continued

|  |  |  |  |
|---|---|---|---|
| | 90 | 95 | 100 |
| ggc ttc tgc cta cct gag tgg gac aac att gtg tgc tgg cct gct gga<br>Gly Phe Cys Leu Pro Glu Trp Asp Asn Ile Val Cys Trp Pro Ala Gly<br>105                    110                  115 | | | 451 |
| gtg ccc ggc aag gtg gtg gcc gtg ccc tgc ccc gac tac ttc tac gac<br>Val Pro Gly Lys Val Val Ala Val Pro Cys Pro Asp Tyr Phe Tyr Asp<br>    120                  125                  130 | | | 499 |
| ttc aac cac aaa ggc cga gcc tat cgg cgc tgt gac agc aat ggc agc<br>Phe Asn His Lys Gly Arg Ala Tyr Arg Arg Cys Asp Ser Asn Gly Ser<br>135                    140                  145                  150 | | | 547 |
| tgg gag ctg gtg cct ggg aac aac cgg aca tgg gcg aat tac agc gaa<br>Trp Glu Leu Val Pro Gly Asn Asn Arg Thr Trp Ala Asn Tyr Ser Glu<br>                  155                  160                  165 | | | 595 |
| tgt gtc aag ttt ctg acc aac gag acc cgg gaa cgg gaa gtc ttt gat<br>Cys Val Lys Phe Leu Thr Asn Glu Thr Arg Glu Arg Glu Val Phe Asp<br>170                    175                  180 | | | 643 |
| cgc ctc gga atg atc tac act gtg ggc tac tcc atc tct ctg ggc tcc<br>Arg Leu Gly Met Ile Tyr Thr Val Gly Tyr Ser Ile Ser Leu Gly Ser<br>                  185                  190                  195 | | | 691 |
| ctc act gtg gct gtg ctg att ctg ggt tac ttt agg agg tta cat tgc<br>Leu Thr Val Ala Val Leu Ile Leu Gly Tyr Phe Arg Arg Leu His Cys<br>200                    205                  210 | | | 739 |
| acc cga aac tac att cac atg cat ctc ttc gtg tcc ttt atg ctc cgg<br>Thr Arg Asn Tyr Ile His Met His Leu Phe Val Ser Phe Met Leu Arg<br>215                    220                  225                  230 | | | 787 |
| gct gta agc atc ttc atc aag gat gct gtg ctc tac tcg ggg gtt tcc<br>Ala Val Ser Ile Phe Ile Lys Asp Ala Val Leu Tyr Ser Gly Val Ser<br>                  235                  240                  245 | | | 835 |
| aca gat gaa atc gag cgc atc acc gag gag gag ctg agg gcc ttc aca<br>Thr Asp Glu Ile Glu Arg Ile Thr Glu Glu Glu Leu Arg Ala Phe Thr<br>250                    255                  260 | | | 883 |
| gag cct ccc cct gct gac aag gcg ggt ttt gtg ggc tgc aga gtg gcg<br>Glu Pro Pro Pro Ala Asp Lys Ala Gly Phe Val Gly Cys Arg Val Ala<br>265                    270                  275 | | | 931 |
| gta acc gtc ttc ctt tac ttc ctg acc acc aac tac tac tgg atc ctg<br>Val Thr Val Phe Leu Tyr Phe Leu Thr Thr Asn Tyr Tyr Trp Ile Leu<br>280                    285                  290 | | | 979 |
| gtg gaa ggc ctc tac ctt cac agc ctc atc ttc atg gct ttc ttc tct<br>Val Glu Gly Leu Tyr Leu His Ser Leu Ile Phe Met Ala Phe Phe Ser<br>295                    300                  305                  310 | | | 1027 |
| gag aaa aag tat ctc tgg ggt ttc aca tta ttt ggc tgg ggc ctc cct<br>Glu Lys Lys Tyr Leu Trp Gly Phe Thr Leu Phe Gly Trp Gly Leu Pro<br>                  315                  320                  325 | | | 1075 |
| gcc gtg ttt gtc gct gtg tgg gtg acc gtg agg gct aca ctg gcc aac<br>Ala Val Phe Val Ala Val Trp Val Thr Val Arg Ala Thr Leu Ala Asn<br>    330                  335                  340 | | | 1123 |
| act gag tgc tgg gac ctg agt tcg ggg aat aag aaa tgg atc ata cag<br>Thr Glu Cys Trp Asp Leu Ser Ser Gly Asn Lys Lys Trp Ile Ile Gln<br>345                    350                  355 | | | 1171 |
| gtg ccc atc ctg gca gct att gtg gtg aac ttt att ctt ttt atc aat<br>Val Pro Ile Leu Ala Ala Ile Val Val Asn Phe Ile Leu Phe Ile Asn<br>360                    365                  370 | | | 1219 |
| ata atc aga gtc ctg gct act aaa ctc cgg gag acc aat gca ggg aga<br>Ile Ile Arg Val Leu Ala Thr Lys Leu Arg Glu Thr Asn Ala Gly Arg<br>375                    380                  385                  390 | | | 1267 |
| tgt gac acg agg caa cag tat aga aag ctg ctg aag tcc acg cta gtc<br>Cys Asp Thr Arg Gln Gln Tyr Arg Lys Leu Leu Lys Ser Thr Leu Val<br>                  395                  400                  405 | | | 1315 |
| ctc atg ccg cta ttt ggg gtg cac tac atc gtc ttc atg gcc acg ccg | | | 1363 |

-continued

```
Leu Met Pro Leu Phe Gly Val His Tyr Ile Val Phe Met Ala Thr Pro
        410                 415                 420 tac aca gaa gta tca ggg att ctt tgg caa gtc caa atg cac tat gaa      1411
Tyr Thr Glu Val Ser Gly Ile Leu Trp Gln Val Gln Met His Tyr Glu
            425                 430                 435 atg ctc ttc aat tca ttc cag gga ttt ttc gtt gcc att ata tac tgt      1459
Met Leu Phe Asn Ser Phe Gln Gly Phe Phe Val Ala Ile Ile Tyr Cys
        440                 445                 450 ttc tgc aat gga gag gta caa gca gag atc aag aag tca tgg agc cga      1507
Phe Cys Asn Gly Glu Val Gln Ala Glu Ile Lys Lys Ser Trp Ser Arg
455                 460                 465                 470 tgg acc ctg gcc ttg gac ttc aag cgg aag gcc cgg agt ggc agc agt      1555
Trp Thr Leu Ala Leu Asp Phe Lys Arg Lys Ala Arg Ser Gly Ser Ser
                475                 480                 485 acc tac agc tat ggc ccc atg gtg tca cat aca agt gtc acc aat gtg      1603
Thr Tyr Ser Tyr Gly Pro Met Val Ser His Thr Ser Val Thr Asn Val
            490                 495                 500 gga cct cga ggg ggg ctg gcc ttg tcc ctc agc cct cga cta gct cct      1651
Gly Pro Arg Gly Gly Leu Ala Leu Ser Leu Ser Pro Arg Leu Ala Pro
        505                 510                 515 ggg gct gga gcc agt gcc aat ggc cat cac cag ttg cct ggc tat gtg      1699
Gly Ala Gly Ala Ser Ala Asn Gly His His Gln Leu Pro Gly Tyr Val
    520                 525                 530 aag cat ggt tcc att tct gag aac tca ttg cct tca tct ggc cca gag      1747
Lys His Gly Ser Ile Ser Glu Asn Ser Leu Pro Ser Ser Gly Pro Glu
535                 540                 545                 550 cct ggc acc aaa gat gac ggg tat ctc aat ggc tct gga ctt tat gag      1795
Pro Gly Thr Lys Asp Asp Gly Tyr Leu Asn Gly Ser Gly Leu Tyr Glu
                555                 560                 565 cca atg gtt ggg gaa cag ccc cct cca ctc ctg gag gag gag aga gag      1843
Pro Met Val Gly Glu Gln Pro Pro Pro Leu Leu Glu Glu Glu Arg Glu
            570                 575                 580 aca gtc atg tgacccatat c                                             1863
Thr Val Met
        585

<210> SEQ ID NO 3
<211> LENGTH: 2051
<212> TYPE: DNA
<213> ORGANISM: Rattus rattus
<220> FEATURE:
<221> NAME/KEY: CDS
<222> LOCATION: (73)...(1845)

<400> SEQUENCE: 3
ggcgggggcc gcggcggcga gctcggaggc cggcggcggc tgccccgagg gacgcggccc        60
taggcggtgg cg atg ggg gcc gcc cgg atc gca ccc agc ctg gcg ctc cta       111
              Met Gly Ala Ala Arg Ile Ala Pro Ser Leu Ala Leu Leu
              1               5                   10 ctc tgc tgc cca gtg ctc agc tcc gca tat gcg ctg gtg gat gcg gac       159
Leu Cys Cys Pro Val Leu Ser Ser Ala Tyr Ala Leu Val Asp Ala Asp
    15                  20                  25 gat gtc ttt acc aaa gag gaa cag att ttc ctg ctg cac cgt gcc cag       207
Asp Val Phe Thr Lys Glu Glu Gln Ile Phe Leu Leu His Arg Ala Gln
30                  35                  40                  45 gcg caa tgt gac aag ctg ctc aag gaa gtt ctg cac aca gca gcc aac       255
Ala Gln Cys Asp Lys Leu Leu Lys Glu Val Leu His Thr Ala Ala Asn
                50                  55                  60 ata atg gag tca gac aag ggc tgg aca cca gca tct acg tca ggg aag       303
Ile Met Glu Ser Asp Lys Gly Trp Thr Pro Ala Ser Thr Ser Gly Lys
            65                  70                  75
```

-continued

| | |
|---|---|
| ccc agg aaa gag aag gca tcg gga aag ttc tac cct gag tct aaa gag<br>Pro Arg Lys Glu Lys Ala Ser Gly Lys Phe Tyr Pro Glu Ser Lys Glu<br>      80                        85                        90 | 351 |
| aac aag gac gtg ccc acc ggc agc agg cgc aga ggg cgt ccc tgt ctg<br>Asn Lys Asp Val Pro Thr Gly Ser Arg Arg Arg Gly Arg Pro Cys Leu<br>      95                        100                    105 | 399 |
| ccc gag tgg gac aac atc gtt tgc tgg cca tta ggg gca cca ggt gaa<br>Pro Glu Trp Asp Asn Ile Val Cys Trp Pro Leu Gly Ala Pro Gly Glu<br>110                      115                    120                    125 | 447 |
| gtg gtg gca gta cct tgt ccc gat tac att tat gac ttc aat cac aaa<br>Val Val Ala Val Pro Cys Pro Asp Tyr Ile Tyr Asp Phe Asn His Lys<br>                130                    135                    140 | 495 |
| ggc cat gcc tac aga cgc tgt gac cgc aat ggc agc tgg gag gtg gtt<br>Gly His Ala Tyr Arg Arg Cys Asp Arg Asn Gly Ser Trp Glu Val Val<br>            145                    150                    155 | 543 |
| cca ggg cac aac cgg acg tgg gcc aac tac agc gag tgc ctc aag ttc<br>Pro Gly His Asn Arg Thr Trp Ala Asn Tyr Ser Glu Cys Leu Lys Phe<br>        160                    165                    170 | 591 |
| atg acc aat gag acg cgg gaa cgg gag gta ttt gac cgc cta ggc atg<br>Met Thr Asn Glu Thr Arg Glu Arg Glu Val Phe Asp Arg Leu Gly Met<br>175                      180                    185 | 639 |
| atc tac acc gtg gga tac tcc atg tct ctc gcc tcc ctc acg gtg gct<br>Ile Tyr Thr Val Gly Tyr Ser Met Ser Leu Ala Ser Leu Thr Val Ala<br>190                      195                    200                    205 | 687 |
| gtg ctc atc ctg gcc tat ttt agg cgg ctg cac tgc acg cgc aac tac<br>Val Leu Ile Leu Ala Tyr Phe Arg Arg Leu His Cys Thr Arg Asn Tyr<br>                210                    215                    220 | 735 |
| atc cac atg cac atg ttc ctg tcg ttt atg ctg cgc gcc gcg agc atc<br>Ile His Met His Met Phe Leu Ser Phe Met Leu Arg Ala Ala Ser Ile<br>            225                    230                    235 | 783 |
| ttc gtg aag gac gct gtg ctc tac tct ggc ttc acg ctg gat gag gcc<br>Phe Val Lys Asp Ala Val Leu Tyr Ser Gly Phe Thr Leu Asp Glu Ala<br>        240                    245                    250 | 831 |
| gag cgc ctc aca gag gaa gag ttg cac atc atc gcg cag gtg cca cct<br>Glu Arg Leu Thr Glu Glu Glu Leu His Ile Ile Ala Gln Val Pro Pro<br>255                      260                    265 | 879 |
| ccg ccg gcc gct gcc gcc gta ggc tac gct ggc tgc cgc gtg gcg gtg<br>Pro Pro Ala Ala Ala Ala Val Gly Tyr Ala Gly Cys Arg Val Ala Val<br>270                      275                    280                    285 | 927 |
| acc ttc ttc ctc tac ttc ctg gct acc aac tac tac tgg att ctg gtg<br>Thr Phe Phe Leu Tyr Phe Leu Ala Thr Asn Tyr Tyr Trp Ile Leu Val<br>                290                    295                    300 | 975 |
| gag ggg ctg tac ttg cac agc ctc atc ttc atg gcc ttt ttc tca gag<br>Glu Gly Leu Tyr Leu His Ser Leu Ile Phe Met Ala Phe Phe Ser Glu<br>            305                    310                    315 | 1023 |
| aag aag tac ctg tgg ggc ttc acc atc ttt ggc tgg ggt cta ccg gct<br>Lys Lys Tyr Leu Trp Gly Phe Thr Ile Phe Gly Trp Gly Leu Pro Ala<br>        320                    325                    330 | 1071 |
| gtc ttc gtg gct gtg tgg gtc ggt gtc aga gca acc ttg gcc aac act<br>Val Phe Val Ala Val Trp Val Gly Val Arg Ala Thr Leu Ala Asn Thr<br>335                      340                    345 | 1119 |
| ggg tgc tgg gat ctg agc tcc ggg cac aag aag tgg atc atc cag gtg<br>Gly Cys Trp Asp Leu Ser Ser Gly His Lys Lys Trp Ile Ile Gln Val<br>350                      355                    360                    365 | 1167 |
| ccc atc ctg gca tct gtt gtg ctc aac ttc atc ctt ttt atc aac atc<br>Pro Ile Leu Ala Ser Val Val Leu Asn Phe Ile Leu Phe Ile Asn Ile<br>                370                    375                    380 | 1215 |
| atc cgg gtg ctt gcc act aag ctt cgg gag acc aat gcg ggc cgg tgt<br>Ile Arg Val Leu Ala Thr Lys Leu Arg Glu Thr Asn Ala Gly Arg Cys | 1263 |

```
                385                 390                 395
gac acc agg cag cag tac cgg aag ctg ctc agg tcc acg ttg gtg ctc    1311
Asp Thr Arg Gln Gln Tyr Arg Lys Leu Leu Arg Ser Thr Leu Val Leu
            400                 405                 410 gtg ccg ctc ttt ggt gtc cac tac acc gtc ttc atg gcc ttg ccg tac    1359
Val Pro Leu Phe Gly Val His Tyr Thr Val Phe Met Ala Leu Pro Tyr
        415                 420                 425 acc gag gtc tca ggg aca ttg tgg cag atc cag atg cat tat gag atg    1407
Thr Glu Val Ser Gly Thr Leu Trp Gln Ile Gln Met His Tyr Glu Met
430                 435                 440                 445 ctc ttc aac tcc ttc cag gga ttt ttt gtt gcc atc ata tac tgt ttc    1455
Leu Phe Asn Ser Phe Gln Gly Phe Phe Val Ala Ile Ile Tyr Cys Phe
                450                 455                 460 tgc aat ggt gag gtg cag gca gag att agg aag tca tgg agc cgc tgg    1503
Cys Asn Gly Glu Val Gln Ala Glu Ile Arg Lys Ser Trp Ser Arg Trp
            465                 470                 475 aca ctg gcg ttg gac ttc aag cgc aaa gca cga agt ggg agt agc agc    1551
Thr Leu Ala Leu Asp Phe Lys Arg Lys Ala Arg Ser Gly Ser Ser Ser
        480                 485                 490 tac agc tat ggc cca atg gtg tct cac acg agt gtg acc aat gtg ggc    1599
Tyr Ser Tyr Gly Pro Met Val Ser His Thr Ser Val Thr Asn Val Gly
495                 500                 505 ccc cgt gca gga ctc agc ctc ccc ctc agc ccc cgc ctg cct cct gcc    1647
Pro Arg Ala Gly Leu Ser Leu Pro Leu Ser Pro Arg Leu Pro Pro Ala
510                 515                 520                 525 act acc aat ggc cac tcc cag ctg cct ggc cat gcc aag cca ggg gct    1695
Thr Thr Asn Gly His Ser Gln Leu Pro Gly His Ala Lys Pro Gly Ala
                530                 535                 540 cca gcc act gag act gaa acc cta cca gtc act atg gcg gtt ccc aag    1743
Pro Ala Thr Glu Thr Glu Thr Leu Pro Val Thr Met Ala Val Pro Lys
            545                 550                 555 gac gat gga ttc ctt aac ggc tcc tgc tca ggc ctg gat gag gag gcc    1791
Asp Asp Gly Phe Leu Asn Gly Ser Cys Ser Gly Leu Asp Glu Glu Ala
        560                 565                 570 tcc ggg tct gcg cgg ccg cct cca ttg ttg cag gaa gga tgg gaa aca    1839
Ser Gly Ser Ala Arg Pro Pro Pro Leu Leu Gln Glu Gly Trp Glu Thr
575                 580                 585 gtc atg tgactgggca ctaggggct agactgctgg cctgggcaca tggacagatg       1895
Val Met
590 gaccaagaag ccagtgtttg gctggttgtc tattcgggat ctggaccagg aagataacaa    1955 aaggaaaatg gaagtggacg aagcagagaa gaaggaagag gttttgcagg aattaaatat    2015 gtttcctcag ttggatgatg aggacacaag gaaggc                              2051

<210> SEQ ID NO 4
<211> LENGTH: 2010
<212> TYPE: DNA
<213> ORGANISM: Homo sapiens
<220> FEATURE:
<221> NAME/KEY: CDS
<222> LOCATION: (28)...(1806)

<400> SEQUENCE: 4
gggatcccgc ggccctaggc ggtggcg atg ggg acc gcc cgg atc gca ccc ggc    54
                            Met Gly Thr Ala Arg Ile Ala Pro Gly
                              1               5 ctg gcg ctc ctg ctc tgc tgc ccc gtg ctc agc tcc gcg tac gcg ctg    102
Leu Ala Leu Leu Leu Cys Cys Pro Val Leu Ser Ser Ala Tyr Ala Leu
 10                  15                  20                  25
```

-continued

| | |
|---|---|
| gtg gat gca gat gac gtc atg act aaa gag gaa cag atc ttc ctg ctg<br>Val Asp Ala Asp Asp Val Met Thr Lys Glu Glu Gln Ile Phe Leu Leu<br>              30                            35                      40 | 150 |
| cac cgt gct cag gcc cag tgc gaa aaa cgg ctc aag gag gtc ctg cag<br>His Arg Ala Gln Ala Gln Cys Glu Lys Arg Leu Lys Glu Val Leu Gln<br>45                            50                            55 | 198 |
| agg cca gcc agc ata atg gaa tca gac aag gga tgg aca tct gcg tcc<br>Arg Pro Ala Ser Ile Met Glu Ser Asp Lys Gly Trp Thr Ser Ala Ser<br>        60                        65                            70 | 246 |
| aca tca ggg aag ccc agg aaa gat aag gca tct ggg aag ctc tac cct<br>Thr Ser Gly Lys Pro Arg Lys Asp Lys Ala Ser Gly Lys Leu Tyr Pro<br>75                            80                            85 | 294 |
| gag tct gag gag gac aag gag gca ccc act ggc agc agg tac cga ggg<br>Glu Ser Glu Glu Asp Lys Glu Ala Pro Thr Gly Ser Arg Tyr Arg Gly<br>90                            95                         100                    105 | 342 |
| cgc ccc tgt ctg ccg gaa tgg gac cac atc ctg tgc tgg ccg ctg ggg<br>Arg Pro Cys Leu Pro Glu Trp Asp His Ile Leu Cys Trp Pro Leu Gly<br>                        110                            115                        120 | 390 |
| gca cca ggt gag gtg gtg gct gtg ccc tgt ccg gac tac att tat gac<br>Ala Pro Gly Glu Val Val Ala Val Pro Cys Pro Asp Tyr Ile Tyr Asp<br>                  125                              130                        135 | 438 |
| ttc aat cac aaa ggc cat gcc tac cga cgc tgt gac cgc aat ggc agc<br>Phe Asn His Lys Gly His Ala Tyr Arg Arg Cys Asp Arg Asn Gly Ser<br>        140                        145                            150 | 486 |
| tgg gag ctg gtg cct ggg cac aac agg acg tgg gcc aac tac agc gag<br>Trp Glu Leu Val Pro Gly His Asn Arg Thr Trp Ala Asn Tyr Ser Glu<br>155                          160                        165 | 534 |
| tgt gtc aaa ttt ctc acc aat gag act cgt gaa cgg gag gtg ttt gac<br>Cys Val Lys Phe Leu Thr Asn Glu Thr Arg Glu Arg Glu Val Phe Asp<br>170                          175                        180                    185 | 582 |
| cgc ctg ggc atg att tac acc gtg ggc tac tcc gtg tcc ctg gcg tcc<br>Arg Leu Gly Met Ile Tyr Thr Val Gly Tyr Ser Val Ser Leu Ala Ser<br>                    190                            195                        200 | 630 |
| ctc acc gta gct gtg ctc atc ctg gcc tac ttt agg cgg ctg cac tgc<br>Leu Thr Val Ala Val Leu Ile Leu Ala Tyr Phe Arg Arg Leu His Cys<br>                  205                            210                        215 | 678 |
| acg cgc aac tac atc cac atg cac ctg ttc ctg tcc ttc atg ctg cgc<br>Thr Arg Asn Tyr Ile His Met His Leu Phe Leu Ser Phe Met Leu Arg<br>        220                        225                            230 | 726 |
| gcc gtg agc atc ttc gtc aag gac gct gtg ctc tac tct ggc gcc acg<br>Ala Val Ser Ile Phe Val Lys Asp Ala Val Leu Tyr Ser Gly Ala Thr<br>235                          240                        245 | 774 |
| ctt gat gag gct gag cgc ctc acc gag gag gag ctg cgc gcc atc gcc<br>Leu Asp Glu Ala Glu Arg Leu Thr Glu Glu Glu Leu Arg Ala Ile Ala<br>250                          255                        260                    265 | 822 |
| cag gcg ccc ccg ccg cct gcc acc gcc gct gcc ggc tac gcg ggc tgc<br>Gln Ala Pro Pro Pro Ala Thr Ala Ala Ala Gly Tyr Ala Gly Cys<br>                  270                            275                        280 | 870 |
| agg gtg gct gtg acc ttc ttc ctt tac ttc ctg gcc acc aac tac tac<br>Arg Val Ala Val Thr Phe Phe Leu Tyr Phe Leu Ala Thr Asn Tyr Tyr<br>                  285                            290                        295 | 918 |
| tgg att ctg gtg gag ggg ctg tac ctg cac agc ctc atc ttc atg gcc<br>Trp Ile Leu Val Glu Gly Leu Tyr Leu His Ser Leu Ile Phe Met Ala<br>        300                        305                            310 | 966 |
| ttc ttc tca gag aag aag tac ctg tgg ggc ttc aca gtc ttc ggc tgg | 1014 |

-continued

| | | | | | | | | | | | | | | | |
|---|---|---|---|---|---|---|---|---|---|---|---|---|---|---|---|
| Phe | Phe | Ser | Glu | Lys | Lys | Tyr | Leu | Trp | Gly | Phe | Thr | Val | Phe | Gly | Trp |
| | 315 | | | | 320 | | | | 325 | | | | | | |

```
ggt ctg ccc gct gtc ttc gtg gct gtg tgg gtc agt gtc aga gct acc      1062
Gly Leu Pro Ala Val Phe Val Ala Val Trp Val Ser Val Arg Ala Thr
330                 335                 340                 345 ctg gcc aac acc ggg tgc tgg gac ttg agc tcc ggg aac aaa aag tgg      1110
Leu Ala Asn Thr Gly Cys Trp Asp Leu Ser Ser Gly Asn Lys Lys Trp
                350                 355                 360 atc atc cag gtg ccc atc ctg gcc tcc att gtg ctc aac ttc atc ctc      1158
Ile Ile Gln Val Pro Ile Leu Ala Ser Ile Val Leu Asn Phe Ile Leu
            365                 370                 375 ttc atc aat atc gtc cgg gtg ctc gcc acc aag cag cgg gag acc aac      1206
Phe Ile Asn Ile Val Arg Val Leu Ala Thr Lys Gln Arg Glu Thr Asn
        380                 385                 390 gcc ggc cgg tgt gac aca cgg cag cag tac cgg aag ctg ctc aaa tcc      1254
Ala Gly Arg Cys Asp Thr Arg Gln Gln Tyr Arg Lys Leu Leu Lys Ser
    395                 400                 405 acg ctg gtg ctc atg ccc ctc ttt ggc gtc cac tac att gtc ttc atg      1302
Thr Leu Val Leu Met Pro Leu Phe Gly Val His Tyr Ile Val Phe Met
410                 415                 420                 425 gcc aca cca tac acc gag gtc tca ggg acg ctc tgg caa gtc cag atg      1350
Ala Thr Pro Tyr Thr Glu Val Ser Gly Thr Leu Trp Gln Val Gln Met
                430                 435                 440 cac tat gag atg ctc ttc aac tcc ttc cag gga ttt ttt gtc gca atc      1398
His Tyr Glu Met Leu Phe Asn Ser Phe Gln Gly Phe Phe Val Ala Ile
            445                 450                 455 ata tac tgt ttc tgc aat ggc gag gta caa gct gag atc aag aaa tct      1446
Ile Tyr Cys Phe Cys Asn Gly Glu Val Gln Ala Glu Ile Lys Lys Ser
        460                 465                 470 tgg agc cgc tgg aca ctg gca ctg gac ttc aag cga aag gca cgc agc      1494
Trp Ser Arg Trp Thr Leu Ala Leu Asp Phe Lys Arg Lys Ala Arg Ser
    475                 480                 485 ggg agc agc agc tat agc tac ggc ccc atg gtg tcc cac aca agt gtg      1542
Gly Ser Ser Ser Tyr Ser Tyr Gly Pro Met Val Ser His Thr Ser Val
490                 495                 500                 505 acc aat gtc ggc ccc cgt gtg gga ctc ggc ctg ccc ctc agc ccc cgc      1590
Thr Asn Val Gly Pro Arg Val Gly Leu Gly Leu Pro Leu Ser Pro Arg
                510                 515                 520 cta ctg ccc act gcc acc acc aac ggc cac cct cag ctg cct ggc cat      1638
Leu Leu Pro Thr Ala Thr Thr Asn Gly His Pro Gln Leu Pro Gly His
            525                 530                 535 gcc aag cca ggg acc cca gcc ctg gag acc ctc gag acc aca cca cct      1686
Ala Lys Pro Gly Thr Pro Ala Leu Glu Thr Leu Glu Thr Thr Pro Pro
        540                 545                 550 gcc atg gct gct ccc aag gac gat ggg ttc ctc aac ggc tcc tgc tca      1734
Ala Met Ala Ala Pro Lys Asp Asp Gly Phe Leu Asn Gly Ser Cys Ser
    555                 560                 565 ggc ctg gac gag gag gcc tct ggg cct gag cgg cca cct gcc ctg cta      1782
Gly Leu Asp Glu Glu Ala Ser Gly Pro Glu Arg Pro Pro Ala Leu Leu
570                 575                 580                 585 cag gaa gag tgg gag aca gtc atg tgaccaggcg ctggggctg gacctgctga     1836
Gln Glu Glu Trp Glu Thr Val Met
                590 catagtggat ggacagatgg accaaaagat gggtggttga atgatttccc actcagggcc   1896
```

-continued

```
tggggccaag aggaaaaaac agggaaaaa agaaaaaaaa aagaaaaaag gaaaaaaaaa    1956
aaaaaaaaaa aaaaaaaaaa aaaaaaaaaa aaaaaaaaaa aaaaaaaaaa aaaa        2010
```

```
<210> SEQ ID NO 5
<211> LENGTH: 20
<212> TYPE: PRT
<213> ORGANISM: Artificial Sequence
<220> FEATURE:
<223> OTHER INFORMATION: binding; 1st to last; peptide fragment

<400> SEQUENCE: 5

Thr Asn Glu Thr Arg Glu Arg Glu Val Phe Asp Arg Leu Gly Met Ile
 1               5                  10                  15

Tyr Thr Val Gly
         20

<210> SEQ ID NO 6
<211> LENGTH: 19
<212> TYPE: PRT
<213> ORGANISM: Artificial Sequence
<220> FEATURE:
<223> OTHER INFORMATION: binding; 1st to last; peptide fragment

<400> SEQUENCE: 6

Tyr Leu Tyr Ser Gly Phe Thr Leu Asp Glu Ala Glu Arg Leu Thr Glu
 1               5                  10                  15

Glu Glu Leu

<210> SEQ ID NO 7
<211> LENGTH: 19
<212> TYPE: PRT
<213> ORGANISM: Artificial Sequence
<220> FEATURE:
<223> OTHER INFORMATION: binding; 1st to last; peptide fragment

<400> SEQUENCE: 7

Val Thr Phe Phe Leu Tyr Phe Leu Ala Thr Asn Tyr Tyr Trp Ile Leu
 1               5                  10                  15

Val Glu Gly

<210> SEQ ID NO 8
<211> LENGTH: 26
<212> TYPE: PRT
<213> ORGANISM: Artificial Sequence
<220> FEATURE:
<223> OTHER INFORMATION: binding; 1st to last; peptide fragment
<220> FEATURE:
<221> NAME/KEY: VARIANT
<222> LOCATION: (1)...(26)
<223> OTHER INFORMATION: Xaa = Any Amino Acid

<400> SEQUENCE: 8

Tyr Xaa Arg Ala Thr Leu Ala Asn Thr Gly Cys Trp Asp Leu Ser Ser
 1               5                  10                  15

Gly His Lys Lys Trp Ile Ile Gln Val Pro
         20                  25

<210> SEQ ID NO 9
<211> LENGTH: 18
<212> TYPE: PRT
<213> ORGANISM: Artificial Sequence
<220> FEATURE:
<223> OTHER INFORMATION: binding; 1st to last; peptide fragment

<400> SEQUENCE: 9
```

-continued

Pro Tyr Thr Glu Tyr Ser Gly Thr Leu Trp Gln Ile Gln Met His Tyr
1               5                  10                  15

Glu Met

<210> SEQ ID NO 10
<211> LENGTH: 18
<212> TYPE: PRT
<213> ORGANISM: Artificial Sequence
<220> FEATURE:
<223> OTHER INFORMATION: binding; 1st to last; peptide fragment

<400> SEQUENCE: 10

Asp Asp Val Phe Thr Lys Glu Glu Gln Ile Phe Leu Leu His Arg Ala
1               5                  10                  15

Gln Ala

<210> SEQ ID NO 11
<211> LENGTH: 10
<212> TYPE: PRT
<213> ORGANISM: Artificial Sequence
<220> FEATURE:
<223> OTHER INFORMATION: binding; 1st to last; peptide fragment

<400> SEQUENCE: 11

Phe Phe Arg Leu His Cys Thr Arg Asn Tyr
1               5                  10

<210> SEQ ID NO 12
<211> LENGTH: 10
<212> TYPE: PRT
<213> ORGANISM: Artificial Sequence
<220> FEATURE:
<223> OTHER INFORMATION: binding; 1st to last; peptide fragment

<400> SEQUENCE: 12

Glu Lys Lys Tyr Leu Trp Gly Phe Thr Leu
1               5                  10

<210> SEQ ID NO 13
<211> LENGTH: 25
<212> TYPE: PRT
<213> ORGANISM: Artificial Sequence
<220> FEATURE:
<223> OTHER INFORMATION: binding; 1st to last; peptide fragment

<400> SEQUENCE: 13

Val Leu Ala Thr Lys Leu Arg Glu Thr Asn Ala Gly Arg Cys Asp Thr
1               5                  10                  15

Arg Gln Gln Tyr Arg Lys Leu Leu Lys
                20                  25

<210> SEQ ID NO 14
<211> LENGTH: 18
<212> TYPE: DNA
<213> ORGANISM: Artificial Sequence
<220> FEATURE:
<223> OTHER INFORMATION: 1st to last; primer

<400> SEQUENCE: 14
agatgaggct gtgcaggt                                                 18

<210> SEQ ID NO 15
<211> LENGTH: 25
<212> TYPE: DNA

-continued

```
<213> ORGANISM: Artificial Sequence
<220> FEATURE:
<223> OTHER INFORMATION: 1st to last; primer

<400> SEQUENCE: 15
ggaattccat gggagcggcc cggat                                           25

<210> SEQ ID NO 16
<211> LENGTH: 24
<212> TYPE: DNA
<213> ORGANISM: Artificial Sequence
<220> FEATURE:
<223> OTHER INFORMATION: 1st to last; primer

<400> SEQUENCE: 16
cgggatcccg cggccctagg cggt                                            24

<210> SEQ ID NO 17
<211> LENGTH: 19
<212> TYPE: DNA
<213> ORGANISM: Artificial Sequence
<220> FEATURE:
<223> OTHER INFORMATION: 1st to last; primer

<400> SEQUENCE: 17
agtatagcgt ccttgacga                                                  19

<210> SEQ ID NO 18
<211> LENGTH: 515
<212> TYPE: PRT
<213> ORGANISM: Didelphoidea

<400> SEQUENCE: 18
```

Met Gly Ala Pro Arg Ile Ser His Ser Leu Ala Leu Leu Cys Cys
 1               5                  10                  15

Ser Val Leu Ser Ser Val Tyr Ala Leu Val Asp Ala Asp Val Ile
                20                  25                  30

Thr Lys Glu Glu Gln Ile Ile Leu Leu Arg Asn Ala Gln Ala Gln Cys
            35                  40                  45

Glu Gln Arg Leu Lys Glu Val Leu Arg Val Pro Glu Leu Ala Glu Ser
        50                  55                  60

Ala Lys Asp Trp Met Ser Arg Ser Ala Lys Thr Lys Lys Glu Lys Pro
65                  70                  75                  80

Ala Glu Lys Leu Tyr Pro Gln Ala Glu Glu Ser Arg Glu Val Ser Asp
                85                  90                  95

Arg Ser Arg Leu Gln Asp Gly Phe Cys Leu Pro Glu Trp Asp Asn Ile
            100                 105                 110

Val Cys Trp Pro Ala Gly Val Pro Gly Lys Val Val Ala Val Pro Cys
        115                 120                 125

Pro Asp Tyr Phe Tyr Asp Phe Asn His Lys Gly Arg Ala Tyr Arg Arg
    130                 135                 140

Cys Asp Ser Asn Gly Ser Trp Glu Leu Val Pro Gly Asn Asn Arg Thr
145                 150                 155                 160

Trp Ala Asn Tyr Ser Glu Cys Val Lys Phe Leu Thr Asn Glu Thr Arg
                165                 170                 175

Glu Arg Glu Val Phe Asp Arg Leu Gly Met Ile Tyr Thr Val Gly Tyr
            180                 185                 190

Ser Ile Ser Leu Gly Ser Leu Thr Val Ala Val Leu Ile Leu Gly Tyr
        195                 200                 205

```
Phe Arg Arg Leu His Cys Thr Arg Asn Tyr Ile His Met His Leu Phe
    210                 215                 220

Val Ser Phe Met Leu Arg Ala Val Ser Ile Phe Ile Lys Asp Ala Val
225                 230                 235                 240

Leu Tyr Ser Gly Val Ser Thr Asp Glu Ile Glu Arg Ile Thr Glu Glu
                    245                 250                 255

Glu Leu Arg Ala Phe Thr Glu Pro Pro Ala Asp Lys Ala Gly Phe
            260                 265                 270

Val Gly Cys Arg Val Ala Val Thr Val Phe Leu Tyr Phe Leu Thr Thr
                275                 280                 285

Asn Tyr Tyr Trp Ile Leu Val Glu Gly Leu Tyr Leu His Ser Leu Ile
    290                 295                 300

Phe Met Ala Phe Phe Ser Glu Lys Lys Tyr Leu Trp Gly Phe Thr Leu
305                 310                 315                 320

Phe Gly Trp Gly Leu Pro Ala Val Phe Val Ala Val Trp Val Thr Val
                    325                 330                 335

Arg Ala Thr Leu Ala Asn Thr Glu Cys Trp Asp Leu Ser Ser Gly Asn
                340                 345                 350

Lys Lys Trp Ile Ile Gln Val Pro Ile Leu Ala Ala Ile Val Val Asn
            355                 360                 365

Phe Ile Leu Phe Ile Asn Ile Ile Arg Val Leu Ala Thr Lys Leu Arg
370                 375                 380

Glu Thr Asn Ala Gly Arg Cys Asp Thr Arg Gln Gln Tyr Arg Lys Leu
385                 390                 395                 400

Leu Lys Ser Thr Leu Val Leu Met Pro Leu Phe Gly Val His Tyr Ile
                    405                 410                 415

Val Phe Met Ala Thr Pro Tyr Thr Glu Val Ser Gly Ile Leu Trp Gln
                420                 425                 430

Val Gln Met His Tyr Glu Met Leu Phe Asn Ser Phe Gln Gly Phe Phe
            435                 440                 445

Val Ala Ile Ile Tyr Cys Phe Cys Asn Gly Glu Val Gln Ala Glu Ile
450                 455                 460

Lys Lys Ser Trp Ser Arg Trp Thr Leu Ala Leu Asp Phe Lys Arg Lys
465                 470                 475                 480

Ala Arg Ser Gly Ser Ser Thr Tyr Ser Tyr Gly Pro Met Val Ser His
                    485                 490                 495

Thr Ser Val Thr Asn Val Gly Pro Arg Gly Gly Trp Pro Cys Pro Ser
                500                 505                 510

Ala Leu Asp
    515

<210> SEQ ID NO 19
<211> LENGTH: 585
<212> TYPE: PRT
<213> ORGANISM: Didelphoidea

<400> SEQUENCE: 19

Met Gly Ala Pro Arg Ile Ser His Ser Leu Ala Leu Leu Leu Cys Cys
1               5                   10                  15

Ser Val Leu Ser Ser Val Tyr Ala Leu Val Asp Ala Asp Asp Val Ile
                20                  25                  30

Thr Lys Glu Glu Gln Ile Ile Leu Leu Arg Asn Ala Gln Ala Gln Cys
            35                  40                  45

Glu Gln Arg Leu Lys Glu Val Leu Arg Val Pro Glu Leu Ala Glu Ser
    50                  55                  60
```

```
Ala Lys Asp Trp Met Ser Arg Ser Ala Lys Thr Lys Glu Lys Pro
 65                  70                  75                  80

Ala Glu Lys Leu Tyr Pro Gln Ala Glu Glu Ser Arg Glu Val Ser Asp
                 85                  90                  95

Arg Ser Arg Leu Gln Asp Gly Phe Cys Leu Pro Glu Trp Asp Asn Ile
                100                 105                 110

Val Cys Trp Pro Ala Gly Val Pro Gly Lys Val Val Ala Val Pro Cys
                115                 120                 125

Pro Asp Tyr Phe Tyr Asp Phe Asn His Lys Gly Arg Ala Tyr Arg Arg
            130                 135                 140

Cys Asp Ser Asn Gly Ser Trp Glu Leu Val Pro Gly Asn Asn Arg Thr
145                 150                 155                 160

Trp Ala Asn Tyr Ser Glu Cys Val Lys Phe Leu Thr Asn Glu Thr Arg
                165                 170                 175

Glu Arg Glu Val Phe Asp Arg Leu Gly Met Ile Tyr Thr Val Gly Tyr
                180                 185                 190

Ser Ile Ser Leu Gly Ser Leu Thr Val Ala Val Leu Ile Leu Gly Tyr
            195                 200                 205

Phe Arg Arg Leu His Cys Thr Arg Asn Tyr Ile His Met His Leu Phe
210                 215                 220

Val Ser Phe Met Leu Arg Ala Val Ser Ile Phe Ile Lys Asp Ala Val
225                 230                 235                 240

Leu Tyr Ser Gly Val Ser Thr Asp Glu Ile Glu Arg Ile Thr Glu Glu
                245                 250                 255

Glu Leu Arg Ala Phe Thr Glu Pro Pro Ala Asp Lys Ala Gly Phe
                260                 265                 270

Val Gly Cys Arg Val Ala Val Thr Val Phe Leu Tyr Phe Leu Thr Thr
            275                 280                 285

Asn Tyr Tyr Trp Ile Leu Val Glu Gly Leu Tyr Leu His Ser Leu Ile
            290                 295                 300

Phe Met Ala Phe Phe Ser Glu Lys Lys Tyr Leu Trp Gly Phe Thr Leu
305                 310                 315                 320

Phe Gly Trp Gly Leu Pro Ala Val Phe Val Ala Val Trp Val Thr Val
                325                 330                 335

Arg Ala Thr Leu Ala Asn Thr Glu Cys Trp Asp Leu Ser Ser Gly Asn
                340                 345                 350

Lys Lys Trp Ile Ile Gln Val Pro Ile Leu Ala Ala Ile Val Val Asn
                355                 360                 365

Phe Ile Leu Phe Ile Asn Ile Ile Arg Val Leu Ala Thr Lys Leu Arg
            370                 375                 380

Glu Thr Asn Ala Gly Arg Cys Asp Thr Arg Gln Gln Tyr Arg Lys Leu
385                 390                 395                 400

Leu Lys Ser Thr Leu Val Leu Met Pro Leu Phe Gly Val His Tyr Ile
                405                 410                 415

Val Phe Met Ala Thr Pro Tyr Thr Glu Val Ser Gly Ile Leu Trp Gln
                420                 425                 430

Val Gln Met His Tyr Glu Met Leu Phe Asn Ser Phe Gln Gly Phe Phe
            435                 440                 445

Val Ala Ile Ile Tyr Cys Phe Cys Asn Gly Glu Val Gln Ala Glu Ile
            450                 455                 460

Lys Lys Ser Trp Ser Arg Trp Thr Leu Ala Leu Asp Phe Lys Arg Lys
465                 470                 475                 480
```

-continued

```
Ala Arg Ser Gly Ser Ser Thr Tyr Ser Tyr Gly Pro Met Val Ser His
            485                 490                 495

Thr Ser Val Thr Asn Val Gly Pro Arg Gly Leu Ala Leu Ser Leu
            500                 505                 510

Ser Pro Arg Leu Ala Pro Gly Ala Gly Ala Ser Ala Asn Gly His His
            515                 520                 525

Gln Leu Pro Gly Tyr Val Lys His Gly Ser Ile Ser Glu Asn Ser Leu
    530                 535                 540

Pro Ser Ser Gly Pro Glu Pro Gly Thr Lys Asp Asp Gly Tyr Leu Asn
545                 550                 555                 560

Gly Ser Gly Leu Tyr Glu Pro Met Val Gly Glu Gln Pro Pro Leu
                565                 570                 575

Leu Glu Glu Glu Arg Glu Thr Val Met
            580                 585

<210> SEQ ID NO 20
<211> LENGTH: 591
<212> TYPE: PRT
<213> ORGANISM: Rattus rattus

<400> SEQUENCE: 20

Met Gly Ala Ala Arg Ile Ala Pro Ser Leu Ala Leu Leu Leu Cys Cys
  1               5                  10                  15

Pro Val Leu Ser Ser Ala Tyr Ala Leu Val Asp Ala Asp Asp Val Phe
                 20                  25                  30

Thr Lys Glu Glu Gln Ile Phe Leu Leu His Arg Ala Gln Ala Gln Cys
             35                  40                  45

Asp Lys Leu Leu Lys Glu Val Leu His Thr Ala Ala Asn Ile Met Glu
     50                  55                  60

Ser Asp Lys Gly Trp Thr Pro Ala Ser Thr Ser Gly Lys Pro Arg Lys
 65                  70                  75                  80

Glu Lys Ala Ser Gly Lys Phe Tyr Pro Glu Ser Lys Glu Asn Lys Asp
                 85                  90                  95

Val Pro Thr Gly Ser Arg Arg Gly Arg Pro Cys Leu Pro Glu Trp
            100                 105                 110

Asp Asn Ile Val Cys Trp Pro Leu Gly Ala Pro Gly Glu Val Val Ala
            115                 120                 125

Val Pro Cys Pro Asp Tyr Ile Tyr Asp Phe Asn His Lys Gly His Ala
    130                 135                 140

Tyr Arg Arg Cys Asp Arg Asn Gly Ser Trp Glu Val Val Pro Gly His
145                 150                 155                 160

Asn Arg Thr Trp Ala Asn Tyr Ser Glu Cys Leu Lys Phe Met Thr Asn
                165                 170                 175

Glu Thr Arg Glu Arg Glu Val Phe Asp Arg Leu Gly Met Ile Tyr Thr
            180                 185                 190

Val Gly Tyr Ser Met Ser Leu Ala Ser Leu Thr Val Ala Val Leu Ile
        195                 200                 205

Leu Ala Tyr Phe Arg Arg Leu His Cys Thr Arg Asn Tyr Ile His Met
    210                 215                 220

His Met Phe Leu Ser Phe Met Leu Arg Ala Ala Ser Ile Phe Val Lys
225                 230                 235                 240

Asp Ala Val Leu Tyr Ser Gly Phe Thr Leu Asp Glu Ala Glu Arg Leu
                245                 250                 255

Thr Glu Glu Glu Leu His Ile Ile Ala Gln Val Pro Pro Pro Pro Ala
            260                 265                 270
```

-continued

```
Ala Ala Ala Val Gly Tyr Ala Gly Cys Arg Val Ala Val Thr Phe Phe
            275                 280                 285

Leu Tyr Phe Leu Ala Thr Asn Tyr Tyr Trp Ile Leu Val Glu Gly Leu
        290                 295                 300

Tyr Leu His Ser Leu Ile Phe Met Ala Phe Phe Ser Glu Lys Lys Tyr
305                 310                 315                 320

Leu Trp Gly Phe Thr Ile Phe Gly Trp Gly Leu Pro Ala Val Phe Val
                325                 330                 335

Ala Val Trp Val Gly Val Arg Ala Thr Leu Ala Asn Thr Gly Cys Trp
            340                 345                 350

Asp Leu Ser Ser Gly His Lys Lys Trp Ile Ile Gln Val Pro Ile Leu
        355                 360                 365

Ala Ser Val Val Leu Asn Phe Ile Leu Phe Ile Asn Ile Ile Arg Val
    370                 375                 380

Leu Ala Thr Lys Leu Arg Glu Thr Asn Ala Gly Arg Cys Asp Thr Arg
385                 390                 395                 400

Gln Gln Tyr Arg Lys Leu Leu Arg Ser Thr Leu Val Leu Val Pro Leu
                405                 410                 415

Phe Gly Val His Tyr Thr Val Phe Met Ala Leu Pro Tyr Thr Glu Val
            420                 425                 430

Ser Gly Thr Leu Trp Gln Ile Gln Met His Tyr Glu Met Leu Phe Asn
        435                 440                 445

Ser Phe Gln Gly Phe Phe Val Ala Ile Ile Tyr Cys Phe Cys Asn Gly
    450                 455                 460

Glu Val Gln Ala Glu Ile Arg Lys Ser Trp Ser Arg Trp Thr Leu Ala
465                 470                 475                 480

Leu Asp Phe Lys Arg Lys Ala Arg Ser Gly Ser Ser Tyr Ser Tyr
                485                 490                 495

Gly Pro Met Val Ser His Thr Ser Val Thr Asn Val Gly Pro Arg Ala
            500                 505                 510

Gly Leu Ser Leu Pro Leu Ser Pro Arg Leu Pro Pro Ala Thr Thr Asn
        515                 520                 525

Gly His Ser Gln Leu Pro Gly His Ala Lys Pro Gly Ala Pro Ala Thr
    530                 535                 540

Glu Thr Glu Thr Leu Pro Val Thr Met Ala Val Pro Lys Asp Asp Gly
545                 550                 555                 560

Phe Leu Asn Gly Ser Cys Ser Gly Leu Asp Glu Glu Ala Ser Gly Ser
                565                 570                 575

Ala Arg Pro Pro Pro Leu Leu Gln Glu Gly Trp Glu Thr Val Met
            580                 585                 590
```

<210> SEQ ID NO 21
<211> LENGTH: 593
<212> TYPE: PRT
<213> ORGANISM: Homo sapiens

<400> SEQUENCE: 21

```
Met Gly Thr Ala Arg Ile Ala Pro Gly Leu Ala Leu Leu Leu Cys Cys
 1               5                  10                  15

Pro Val Leu Ser Ser Ala Tyr Ala Leu Val Asp Ala Asp Asp Val Met
            20                  25                  30

Thr Lys Glu Glu Gln Ile Phe Leu Leu His Arg Ala Gln Ala Gln Cys
        35                  40                  45

Glu Lys Arg Leu Lys Glu Val Leu Gln Arg Pro Ala Ser Ile Met Glu
```

```
            50                  55                  60
Ser Asp Lys Gly Trp Thr Ser Ala Ser Thr Ser Gly Lys Pro Arg Lys
 65                  70                  75                  80

Asp Lys Ala Ser Gly Lys Leu Tyr Pro Glu Ser Glu Asp Lys Glu
                 85                  90                  95

Ala Pro Thr Gly Ser Arg Tyr Arg Gly Arg Pro Cys Leu Pro Glu Trp
                100                 105                 110

Asp His Ile Leu Cys Trp Pro Leu Gly Ala Pro Gly Glu Val Val Ala
                115                 120                 125

Val Pro Cys Pro Asp Tyr Ile Tyr Asp Phe Asn His Lys Gly His Ala
130                 135                 140

Tyr Arg Arg Cys Asp Arg Asn Gly Ser Trp Glu Leu Val Pro Gly His
145                 150                 155                 160

Asn Arg Thr Trp Ala Asn Tyr Ser Glu Cys Val Lys Phe Leu Thr Asn
                165                 170                 175

Glu Thr Arg Glu Arg Glu Val Phe Asp Arg Leu Gly Met Ile Tyr Thr
                180                 185                 190

Val Gly Tyr Ser Val Ser Leu Ala Ser Leu Thr Val Ala Val Leu Ile
                195                 200                 205

Leu Ala Tyr Phe Arg Arg Leu His Cys Thr Arg Asn Tyr Ile His Met
210                 215                 220

His Leu Phe Leu Ser Phe Met Leu Arg Ala Val Ser Ile Phe Val Lys
225                 230                 235                 240

Asp Ala Val Leu Tyr Ser Gly Ala Thr Leu Asp Glu Ala Glu Arg Leu
                245                 250                 255

Thr Glu Glu Leu Arg Ala Ile Ala Gln Ala Pro Pro Pro Ala
                260                 265                 270

Thr Ala Ala Gly Tyr Ala Gly Cys Arg Val Ala Val Thr Phe Phe
                275                 280                 285

Leu Tyr Phe Leu Ala Thr Asn Tyr Tyr Trp Ile Leu Val Glu Gly Leu
290                 295                 300

Tyr Leu His Ser Leu Ile Phe Met Ala Phe Phe Ser Glu Lys Lys Tyr
305                 310                 315                 320

Leu Trp Gly Phe Thr Val Phe Gly Trp Gly Leu Pro Ala Val Phe Val
                325                 330                 335

Ala Val Trp Val Ser Val Arg Ala Thr Leu Ala Asn Thr Gly Cys Trp
                340                 345                 350

Asp Leu Ser Ser Gly Asn Lys Lys Trp Ile Ile Gln Val Pro Ile Leu
                355                 360                 365

Ala Ser Ile Val Leu Asn Phe Ile Leu Phe Ile Asn Ile Val Arg Val
370                 375                 380

Leu Ala Thr Lys Gln Arg Glu Thr Asn Ala Gly Arg Cys Asp Thr Arg
385                 390                 395                 400

Gln Gln Tyr Arg Lys Leu Leu Lys Ser Thr Leu Val Leu Met Pro Leu
                405                 410                 415

Phe Gly Val His Tyr Ile Val Phe Met Ala Thr Pro Tyr Thr Glu Val
                420                 425                 430

Ser Gly Thr Leu Trp Gln Val Gln Met His Tyr Glu Met Leu Phe Asn
                435                 440                 445

Ser Phe Gln Gly Phe Phe Val Ala Ile Ile Tyr Cys Phe Cys Asn Gly
                450                 455                 460

Glu Val Gln Ala Glu Ile Lys Lys Ser Trp Ser Arg Trp Thr Leu Ala
465                 470                 475                 480
```

-continued

```
Leu Asp Phe Lys Arg Lys Ala Arg Ser Gly Ser Ser Ser Tyr Ser Tyr
             485             490                 495

Gly Pro Met Val Ser His Thr Ser Val Thr Asn Val Gly Pro Arg Val
             500             505                 510

Gly Leu Gly Leu Pro Leu Ser Pro Arg Leu Leu Pro Thr Ala Thr Thr
             515             520                 525

Asn Gly His Pro Gln Leu Pro Gly His Ala Lys Pro Gly Thr Pro Ala
             530             535                 540

Leu Glu Thr Leu Glu Thr Thr Pro Pro Ala Met Ala Ala Pro Lys Asp
545                  550                 555                 560

Asp Gly Phe Leu Asn Gly Ser Cys Ser Gly Leu Asp Glu Glu Ala Ser
                     565             570                 575

Gly Pro Glu Arg Pro Pro Ala Leu Leu Gln Glu Glu Trp Glu Thr Val
                 580             585                 590

Met
```

What is claimed is:

1. A method for identifying a compound that inhibits binding of a parathyroid hormone to a parathyroid hormone receptor by competitively binding to the parathyroid hormone receptor, the method comprising:
   (a) providing a recombinant polypeptide that: (i) comprises an amino acid sequence that is at least 30% identical to SEQ ID NO:20, and (ii) binds to parathyroid hormone;
   (b) contacting the polypeptide with a parathyroid hormone, or a parathyroid hormone receptor-binding fragment thereof, in the presence of a candidate compound; and
   (c) comparing the level of binding of the polypeptide to the parathyroid hormone or fragment thereof in the presence of the candidate compound with the level of binding of the polypeptide to the parathyroid hormone or fragment thereof in the absence of the candidate compound, wherein a lower level of binding in the presence of the candidate compound than in its absence indicates that the candidate compound competes with parathyroid hormone for binding to the receptor.

2. The method of claim 1, wherein the amino acid sequence is identical to the sequence of a fragment of a parathyroid hormone receptor.

3. The method of claim 1, wherein the amino acid sequence is identical to the sequence of a fragment of a human parathyroid hormone receptor.

4. The method of claim 1, wherein the amino acid sequence is identical to SEQ ID NO:21.

5. A method for identifying a compound that inhibits the binding of parathyroid hormone to a parathyroid hormone receptor, the method comprising:
   (a) providing a recombinant polypeptide that: (i) consists of an amino acid sequence that is at least 30% identical to SEQ ID NO:20 and (ii) binds parathyroid hormone or a fragment thereof;
   (b) contacting the polypeptide with parathyroid hormone, or a parathyroid hormone receptor-binding fragment thereof, and a test compound; and
   (c) determining whether binding of the parathyroid hormone or fragment thereof to the polypeptide is decreased in the presence of the test compound, wherein a decrease in binding indicates that the test compound inhibits the binding of parathyroid hormone to the parathyroid hormone receptor.

6. The method of claim 5, wherein the amino acid sequence of is identical to SEQ ID NO:21.

7. A method for identifying a compound that inhibits the binding of parathyroid hormone to a parathyroid hormone receptor, the method comprising:
   (a) providing a recombinant parathyroid hormone receptor or a parathyroid hormone-binding fragment thereof, wherein the amino acid sequence of the parathyroid hormone receptor is at least 30% identical to SEQ ID NO: 20;
   (b) contacting the parathyroid hormone receptor or fragment thereof with parathyroid hormone or a parathyroid receptor-binding fragment thereof, and a test compound; and
   (c) determining whether binding of the parathyroid hormone or fragment thereof to the parathyroid hormone receptor or fragment thereof is decreased in the presence of the test compound, wherein a decrease in binding indicates that the test compound inhibits the binding of parathyroid hormone to the parathyroid hormone receptor.

8. The method of claim 1, wherein the amino acid sequence is identical to SEQ ID NO:21 with at least one conservative amino acid substitution.

9. A method for identifying a compound that inhibits binding of a parathyroid hormone to a parathyroid hormone receptor by competitively binding to the parathyroid hormone receptor, the method comprising:
   (a) providing a recombinant polypeptide that: (i) comprises a fragment of a parathyroid hormone receptor having an amino acid sequence that is at least 30% identical to SEQ ID NO: 20, and (ii) binds to parathyroid hormone;
   (b) contacting the polypeptide with a parathyroid hormone, or a parathyroid hormone receptor-binding fragment thereof, in the presence of a candidate compound; and
   (c) comparing the level of binding of the polypeptide to the parathyroid hormone or fragment thereof in the presence of the candidate compound with the level of binding of the polypeptide to the parathyroid hormone or fragment thereof in the absence of the candidate compound, wherein a lower level of binding in the presence of the candidate compound than in its absence indicates that the candidate compound competes with parathyroid hormone for binding to the receptor.

10. The method of claim 1, wherein the amino acid sequence comprises one or more of SEQ ID NOs:5–13.

11. The method of claim 1, wherein the amino acid sequence is identical to a fragment of an opossum parathyroid hormone receptor.

12. The method of claim 1, wherein the amino acid sequence is identical to a fragment of a rat parathyroid hormone receptor.

13. The method of claim 1, wherein the amino acid sequence is identical to SEQ ID NO:18.

14. The method of claim 1, wherein the amino acid sequence is identical to SEQ ID NO:19.

15. The method of claim 1, wherein the amino acid sequence is identical to SEQ ID NO:20.

16. The method of claim 1, wherein the amino acid sequence is at least 50% identical to SEQ ID NO:20.

17. The method of claim 1, wherein the amino acid sequence is at least 60% identical to SEQ ID NO:20.

18. The method of claim 1, wherein the amino acid sequence is at least 75% identical to SEQ ID NO:20.

19. The method of claim 5, wherein the amino acid sequence is identical to the sequence of a fragment of a parathyroid hormone receptor.

20. The method of claim 5, wherein the amino acid sequence is identical to the sequence of a fragment of a human parathyroid hormone receptor.

21. The method of claim 5, wherein the amino acid sequence is identical to SEQ ID NO:21 with at least one conservative amino acid substitution.

22. The method of claim 5, wherein the amino acid sequence comprises one or more of SEQ ID NOs:5–13.

23. The method of claim 5, wherein the amino acid sequence is identical to a fragment of an opossum parathyroid hormone receptor.

24. The method of claim 5, wherein the amino acid sequence is identical to a fragment of a rat parathyroid hormone receptor.

25. The method of claim 5, wherein the amino acid sequence is identical to SEQ ID NO:18.

26. The method of claim 5, wherein the amino acid sequence is identical to SEQ ID NO:19.

27. The method of claim 5, wherein the amino acid sequence is identical to SEQ ID NO:20.

28. The method of claim 5, wherein the amino acid sequence is at least 50% identical to SEQ ID NO:20.

29. The method of claim 5, wherein the amino acid sequence is at least 60% identical to SEQ ID NO:20.

30. The method of claim 5, wherein the amino acid sequence is at least 75% identical to SEQ ID NO:20.

31. The method of claim 7, wherein the amino acid sequence is identical to SEQ ID NO:21.

32. The method of claim 7, wherein the amino acid sequence is identical to the sequence of a fragment of a human parathyroid hormone receptor.

33. The method of claim 7, wherein the amino acid sequence is identical to SEQ ID NO:21 with at least one conservative amino acid substitution.

34. The method of claim 7, wherein the amino acid sequence comprises part or all of any one of SEQ ID NOs:5–13.

35. The method of claim 7, wherein the amino acid sequence is identical to a fragment of an opossum parathyroid hormone receptor.

36. The method of claim 7, wherein the amino acid sequence is identical to a fragment of a rat parathyroid hormone receptor.

37. The method of claim 7, wherein the amino acid sequence is identical to SEQ ID NO:18.

38. The method of claim 7, wherein the amino acid sequence is identical to SEQ ID NO:19.

39. The method of claim 7, wherein the amino acid sequence is identical to SEQ ID NO:20.

40. The method of claim 7, wherein the amino acid sequence comprises part or all of any one of SEQ ID NOs:5–13.

41. The method of claim 7, wherein the amino acid sequence is at least 50% identical to SEQ ID NO:20.

42. The method of claim 7, wherein the amino acid sequence is at least 60% identical to SEQ ID NO:20.

43. The method of claim 7, wherein the amino acid sequence is at least 75% identical to SEQ ID NO:20.

44. The method of claim 9, wherein the amino acid sequence is identical to SEQ ID NO:21.

45. The method of claim 9, wherein the amino acid sequence is identical to the sequence of a fragment of a human parathyroid hormone receptor.

46. The method of claim 9, wherein the amino acid sequence is identical to SEQ ID NO:21 with at least one conservative amino acid substitution.

47. The method of claim 9, wherein the amino acid sequence comprises one or more of SEQ ID NOs:5–13.

48. The method of claim 9, wherein the amino acid sequence is identical to a fragment of an opossum parathyroid hormone receptor.

49. The method of claim 9, wherein the amino acid sequence is identical to a fragment of a rat parathyroid hormone receptor.

50. The method of claim 9, wherein the amino acid sequence is identical to SEQ ID NO:18.

51. The method of claim 9, wherein the amino acid sequence is identical to SEQ ID NO:19.

52. The method of claim 9, wherein the amino acid sequence is identical to SEQ ID NO:20.

53. The method of claim 9, wherein the amino acid sequence is at least 50% identical to SEQ ID NO:20.

54. The method of claim 9, wherein the amino acid sequence is at least 60% identical to SEQ ID NO:20.

55. The method of claim 9, wherein the amino acid sequence is at least 75% identical to SEQ ID NO:20.

* * * * *